United States Patent
Groves et al.

(10) Patent No.: US 11,059,802 B2
(45) Date of Patent: Jul. 13, 2021

(54) CARBONIC ANHYDRASE TARGETING AGENTS AND METHODS OF USING SAME

(71) Applicant: VisEn Medical, Inc., Waltham, MA (US)

(72) Inventors: Kevin Groves, Arlington, MA (US); Bagna Bao, Sharon, MA (US)

(73) Assignee: VisEn Medical, Inc., Waltham, MA (US)

( * ) Notice: Subject to any disclaimer, the term of this patent is extended or adjusted under 35 U.S.C. 154(b) by 0 days.

(21) Appl. No.: 16/286,901

(22) Filed: Feb. 27, 2019

(65) Prior Publication Data

US 2019/0300501 A1 Oct. 3, 2019

Related U.S. Application Data

(62) Division of application No. 13/467,694, filed on May 9, 2012, now Pat. No. 10,221,159.

(60) Provisional application No. 61/483,979, filed on May 9, 2011.

(51) Int. Cl.
| | |
|---|---|
| *C07D 401/06* | (2006.01) |
| *C07D 401/14* | (2006.01) |
| *C07D 417/14* | (2006.01) |
| *A61K 49/00* | (2006.01) |
| *G01N 33/58* | (2006.01) |
| *C09B 23/08* | (2006.01) |
| *G01N 21/64* | (2006.01) |
| *C07D 209/14* | (2006.01) |
| *C07D 209/60* | (2006.01) |
| *C09B 23/01* | (2006.01) |
| *A61K 31/433* | (2006.01) |
| *A61K 31/4439* | (2006.01) |
| *A61K 31/444* | (2006.01) |
| *A61K 31/506* | (2006.01) |

(52) U.S. Cl.
CPC .......... *C07D 401/06* (2013.01); *A61K 31/433* (2013.01); *A61K 31/444* (2013.01); *A61K 31/4439* (2013.01); *A61K 31/506* (2013.01); *A61K 49/0002* (2013.01); *A61K 49/0032* (2013.01); *A61K 49/0052* (2013.01); *C07D 209/14* (2013.01); *C07D 209/60* (2013.01); *C07D 401/14* (2013.01); *C07D 417/14* (2013.01); *C09B 23/0008* (2013.01); *C09B 23/0033* (2013.01); *C09B 23/083* (2013.01); *C09B 23/086* (2013.01); *G01N 21/6458* (2013.01); *G01N 33/582* (2013.01); *G01N 2333/988* (2013.01); *Y02A 50/30* (2018.01)

(58) Field of Classification Search
CPC .. A61K 31/00; A61K 31/433; A61K 31/4439; A61K 31/444; A61K 31/506; A61K 49/00; A61K 49/0002; A61K 49/0032; A61K 31/403; A61K 31/404; A61K 31/795; A61K 49/0054; A61K 49/0052; C07D 401/06; C07D 209/14; C07D 209/60; C07D 401/14; C07D 417/14; C07D 209/08; C09B 23/0033; C09B 23/0008; C09B 23/083; C09B 23/086; G01N 21/6458; G01N 33/582; G01N 2333/988; Y02A 50/414; Y02A 50/423; Y02A 50/411; Y02A 50/30; A61P 9/00; A61P 37/00; A61P 35/00; A61P 29/00; C08G 65/00

USPC ...... 424/1.11, 1.65, 1.81, 1.85, 9.1, 9.2, 9.6; 534/7, 10–16

See application file for complete search history.

(56) References Cited

U.S. PATENT DOCUMENTS

| | | | |
|---|---|---|---|
| 4,647,447 | A | 3/1987 | Gries et al. |
| 4,981,977 | A | 1/1991 | Southwick et al. |
| 5,268,486 | A | 12/1993 | Waggoner et al. |
| 5,486,616 | A | 1/1996 | Waggoner et al. |
| 5,569,587 | A | 10/1996 | Waggoner |
| 5,569,766 | A | 10/1996 | Waggoner et al. |
| 5,593,658 | A | 1/1997 | Bogdanov et al. |
| 5,627,027 | A | 5/1997 | Waggoner |
| 5,808,044 | A | 9/1998 | Brush et al. |
| 5,877,310 | A | 3/1999 | Reddington et al. |
| 6,002,003 | A | 12/1999 | Shen et al. |
| 6,004,536 | A | 12/1999 | Leung et al. |
| 6,008,373 | A | 12/1999 | Waggoner et al. |
| 6,043,025 | A | 3/2000 | Minden et al. |
| 6,083,485 | A | 7/2000 | Licha et al. |
| 6,083,486 | A | 7/2000 | Weissleder et al. |
| 6,127,134 | A | 10/2000 | Minden et al. |
| 6,130,094 | A | 10/2000 | Waggoner et al. |
| 6,133,445 | A | 10/2000 | Waggoner et al. |
| 6,136,612 | A | 10/2000 | Della Ciana et al. |
| 6,258,340 | B1 | 7/2001 | Licha et al. |
| 6,448,008 | B1 | 9/2002 | Caputo et al. |
| 6,534,041 | B1 | 3/2003 | Licha et al. |
| 6,592,847 | B1 | 7/2003 | Weissleder et al. |
| 6,615,063 | B1 | 9/2003 | Ntziachristos et al. |

(Continued)

FOREIGN PATENT DOCUMENTS

| | | |
|---|---|---|
| EP | 1065250 A1 | 1/2001 |
| WO | WO-97/40104 A1 | 10/1997 |

(Continued)

OTHER PUBLICATIONS

Ahlskog et al., "In Vivo Targeting of Tumor-Associated Carbonic Anhydrases Using Acetazolamide Derivatives," Bioorganic & Medicinal Chemistry Letters, vol. 19, pp. 4851-4856 (2009).

(Continued)

*Primary Examiner* — D. L. Jones
(74) *Attorney, Agent, or Firm* — Goodwin Procter LLP

(57) ABSTRACT

The invention provides agents that target carbonic anhydrase, which can be used as imaging agents or therapeutic agents. The agents can be used to image tumor hypoxia as well as other physiological processes in a subject.

32 Claims, 7 Drawing Sheets
(6 of 7 Drawing Sheet(s) Filed in Color)

(56) References Cited

U.S. PATENT DOCUMENTS

| | | | |
|---|---|---|---|
| 6,740,755 | B2 | 5/2004 | Caputo et al. |
| 6,747,159 | B2 | 6/2004 | Caputo et al. |
| 6,794,509 | B1 | 9/2004 | Nishigaki et al. |
| 6,869,593 | B2 | 3/2005 | Frangioni |
| 6,913,743 | B2 | 7/2005 | Licha et al. |
| 6,926,885 | B2 | 8/2005 | Licha et al. |
| 7,025,949 | B2 | 4/2006 | Licha et al. |
| 7,374,746 | B2 | 5/2008 | Frangioni |
| 7,439,319 | B2 | 10/2008 | Smith et al. |
| 7,445,767 | B2 | 11/2008 | Licha et al. |
| 7,647,091 | B2 | 1/2010 | Ntziachristos et al. |
| 7,655,217 | B2 | 2/2010 | Licha et al. |
| 7,833,737 | B2 | 11/2010 | Supuran et al. |
| 7,947,256 | B2 | 5/2011 | Rajopadhye et al. |
| 7,962,200 | B2 | 6/2011 | Ntziachristos et al. |
| 8,170,651 | B2 | 5/2012 | Ripoll Lorenzo et al. |
| 8,173,819 | B2 | 5/2012 | Rajopadhye et al. |
| 8,221,721 | B2 | 7/2012 | Narayanan |
| 8,420,055 | B2 | 4/2013 | Gaw et al. |
| 8,455,651 | B2 | 6/2013 | Rajopadhye et al. |
| 8,486,373 | B2 | 7/2013 | Weissleder et al. |
| 8,685,370 | B2 | 4/2014 | Rajopadhye et al. |
| 8,771,646 | B2 | 7/2014 | Rajopadhye et al. |
| 8,815,214 | B2 | 8/2014 | Rajopadhye et al. |
| 8,864,821 | B2 | 10/2014 | Jaffer et al. |
| 9,365,721 | B2 | 6/2016 | Narayanan |
| 9,371,362 | B2 | 6/2016 | Ho |
| 9,375,493 | B2 | 6/2016 | Ho |
| 9,427,481 | B2 | 8/2016 | Rajopadhye et al. |
| 9,463,171 | B2 | 10/2016 | Supuran et al. |
| 9,574,085 | B2 | 2/2017 | Narayanan et al. |
| 9,649,389 | B2 | 5/2017 | Groves et al. |
| 9,897,604 | B2 | 2/2018 | Narayanan |
| 9,913,917 | B2 | 3/2018 | Groves et al. |
| 9,999,687 | B2 | 6/2018 | Rajopadhye et al. |
| 10,092,188 | B2 | 10/2018 | Jaffer et al. |
| 10,221,159 | B2 * | 3/2019 | Groves ................ A61K 31/506 |
| 2002/0156288 | A1 | 10/2002 | Caputo et al. |
| 2003/0124194 | A1 | 7/2003 | Gaw et al. |
| 2005/0106106 | A1 | 5/2005 | Licha et al. |
| 2005/0169843 | A1 | 8/2005 | Weissleder et al. |
| 2005/0169844 | A1 | 8/2005 | Licha et al. |
| 2005/0171434 | A1 | 8/2005 | Madden et al. |
| 2008/0102036 | A1 | 5/2008 | Poss et al. |
| 2008/0138291 | A1 | 6/2008 | Supuran et al. |
| 2008/0226562 | A1 | 9/2008 | Groves et al. |
| 2008/0286207 | A1 | 11/2008 | Narayanan |
| 2008/0317676 | A1 | 12/2008 | Rajopadhye et al. |
| 2009/0130024 | A1 | 5/2009 | Narayanan et al. |
| 2010/0074847 | A1 | 3/2010 | Madden et al. |
| 2010/0078576 | A1 | 4/2010 | Ntziachristos et al. |
| 2010/0166659 | A1 | 7/2010 | Licha et al. |
| 2010/0172841 | A1 | 7/2010 | Peterson et al. |
| 2010/0189657 | A1 | 7/2010 | Weissleder et al. |
| 2010/0323389 | A1 | 12/2010 | Xu et al. |
| 2011/0049384 | A1 | 3/2011 | Yared et al. |
| 2011/0060211 | A1 | 3/2011 | Lorenzo et al. |
| 2011/0071388 | A1 | 3/2011 | Yared et al. |
| 2011/0087111 | A1 | 4/2011 | Ntziachristos |
| 2011/0152501 | A1 | 6/2011 | Weissleder et al. |
| 2011/0165075 | A1 | 7/2011 | Rajopadhye et al. |
| 2011/0171136 | A1 | 7/2011 | Poss et al. |
| 2011/0184277 | A1 | 7/2011 | Ripoll Lorenzo et al. |
| 2011/0256065 | A1 | 10/2011 | Frangioni |
| 2012/0321563 | A1 | 12/2012 | Groves et al. |
| 2013/0137873 | A1 | 5/2013 | Narayanan |
| 2014/0050662 | A1 | 2/2014 | Ho |
| 2014/0314677 | A1 | 10/2014 | Groves et al. |
| 2014/0348746 | A1 | 11/2014 | Narayanan |
| 2015/0018517 | A1 | 1/2015 | Rajopadhye et al. |
| 2015/0133773 | A1 | 5/2015 | Jaffer et al. |

FOREIGN PATENT DOCUMENTS

| | | |
|---|---|---|
| WO | WO-99/51702 A1 | 10/1999 |
| WO | WO-01/21624 A1 | 3/2001 |
| WO | WO-2003/079015 A1 | 9/2003 |
| WO | WO-2003/102558 A1 | 12/2003 |
| WO | WO-2006/137009 A2 | 12/2006 |
| WO | WO-2006/137092 A1 | 12/2006 |
| WO | WO-2007/028037 A1 | 3/2007 |
| WO | WO-2007/028118 A2 | 3/2007 |
| WO | WO-2008/100817 A2 | 8/2008 |
| WO | WO-2008/124703 A2 | 10/2008 |
| WO | WO-2009/114776 A2 | 9/2009 |
| WO | WO-2010/065906 A2 | 6/2010 |
| WO | WO-2010/121163 A2 | 10/2010 |
| WO | WO-2010/147666 A1 | 12/2010 |

OTHER PUBLICATIONS

Akurathi et al., "Synthesis and Biological Evaluation of a 99mTc-labelled Sulfonamide Conjugate for in Vivo Visualization of Carbonic Anhydrase IX Expression in Tumor Hypoxia," Nuclear Medicine and Biology, vol. 37, pp. 557-564 (2010).

Alfano et al., "Advances in Optical Imaging of Biomedical Media," Annals New York Academy of Sciences, vol. 820, pp. 248-270 (1997).

Brubaker et al., "Localization of Carbonic Anhydrase in Living Osteoclasts with Bodipy 558/568-modified Acetazolamide, a Thiadiazole Carbonic Anhydrase Inhibitor," The Journal of Histochemistry & Cytochemistry, vol. 47, pp. 545-550 (1999).

Cecchi et al., "Carbonic Anhydrase Inhibitors. Design of Fluorescent Sulfonamides as Probes of Tumor-Associated Carbonic Anhydrase IX That Inhibit Isozyme IX-Mediated Acidification of Hypoxic Tumors," Journal of Medicinal Chemistry, vol. 48, pp. 4834-4841 (2005).

Chrastina et al., "Biodistribution and Pharmacokinetics of 125I-labeled Monoclonal Antibody M75 Specific for Carbonic Anhydrase IX, an Intrinsic Marker of Hypoxia, in Nude Mice Xenografted with Human Colorectal Carcinoma," International Journal of Cancer, vol. 105, pp. 873-881 (2003).

Citrin et al., "Optical Imaging of Mice in Oncologic Research," Expert Rev. Anticancer Ther., vol. 4, pp. 857-864 (2004).

Clayden, J. et al., Organic Chemistry, Oxford University Press: New York, 2001, p. 1249-51.

Dubois et al., "Imaging of CA IX with Fluorescent Labelled Sulfonamides Distinguishes Hypoxic and (Re)-oxygenated Cells in a Xenograft Tumour Model," Radiotherapy and Oncology Journal of the European Society for Radiotherapy and Oncology, vol. 92, pp. 423-428 (2009).

Dubois et al., "Imaging the Hypoxia Surrogate Marker CA IX Requires Expression and Catalytic Activity for Binding Fluorescent Sulfonamide Inhibitors," Radiotherapy and Oncology Journal of the European Society for Radiotherapy and Oncology, vol. 83, pp. 367-373 (2007).

Graves et al., "Fluorescence Molecular Imaging of Small Animal Tumor Models," Current Molecular Medicine, vol. 4, pp. 419-430 (2004).

International Search Report for International Application No. PCT/US2012/037166 dated Dec. 11, 2012.

Koo et al., "Non-Invasive in Vivo Imaging in Small Animal Research," Cellular Oncology, vol. 28, pp. 127-139 (2006).

Ntziachristos et al., "Fluorescence Imaging with Near-Infrared Light: New Technology Advances that Enable in Vivo Molecular Imaging," Eur. Radiol., vol. 13, pp. 195-208 (2003).

Ntziachristos, "Fluorescence Molecular Imaging," The Annual Review of Biomedical Engineering, vol. 8, pp. 1-33 (2006).

Ozmen et al., "Infrared Fluorescence Sensing of Submicromolar Calcium: Pushing the Limits of Photoinduced Electron Transfer," Tetrahedron Letters 41, pp. 9185-9188 (2000).

Rami et al., "Synthesis of Rhodamine B-benzenesulfonamide Conjugates and their Inhibitory Acitivity Against Human Alpha- and Bacterial/fungal Beta-Carbonic Anhydrases," Bioorganic & Medicinal Chemistry Letters, vol. 21, pp. 5210-5213 (2011).

(56) References Cited

OTHER PUBLICATIONS

Rami, M. et al., Carbonic anhydrase inhibitors: Gd(III) complexes of DOTA- and TETA-sulfonamide conjugates targeting the tumor associated carbonic anhydrase isozymes IX and XII, New Journal of Chemistry, 2010, 34, 2139-2144.
Rao et al., "Fluorescence Imaging in Vivo: Recent Advances," Current Opinion in Biotechnology, vol. 18, pp. 17-25 (2007).
Smith M.B.et al., March's Advanced Organic Chemistry, Fifth Edition, A Wiley-Interscience Publication: New Jersey, 1992, p. 274-275.
Tafreshi et al., "Non-Invasive Detection of Breast Cancer Lymph Node Metastasis using Carbonic Anhydrases IX and XII Targeted Imaging Probes," Clinical Cancer Research, (Author Manuscript) pp. 1-41 (2011).
Weissleder, "A Clearer Vision for in Vivo Imaging," Nature Biotechnology, vol. 19, pp. 316-317 (2001).
Written Opinion of the International Search Authority for International Application No. PCT/US2012/037166 dated Dec. 11, 2012 (6 pages).

* cited by examiner

CARBONIC ANHYDRASE TARGETING AGENTS AND METHODS OF USING SAME

CROSS-REFERENCE TO RELATED APPLICATIONS

This application is a divisional of U.S. patent application Ser. No. 13/467,694, filed May 9, 2012, which claims the benefit of and priority to U.S. Provisional Patent Application No. 61/483,979, filed May 9, 2011, the contents of each of which are hereby incorporated by reference.

FIELD OF THE INVENTION

The invention provides agents that target carbonic anhydrase, which can be used as imaging agents or therapeutic agents. The agents can be used to image tumor hypoxia as well as other physiological processes in a subject.

BACKGROUND

Current approaches for assessing molecular endpoints in certain diseases usually require tissue and blood sampling, surgery, and in the case of experimental animals, sacrifice at different time points. Despite improvements in noninvasive imaging, more sensitive and specific imaging agents and methods are urgently needed. Imaging techniques capable of visualizing specific molecular targets and/or entire pathways would significantly enhance our ability to diagnose and assess treatment efficacy of therapeutic interventions for many different disease states. Most current imaging techniques report primarily on anatomical or physiological information (e.g., magnetic resonance imaging (MRI), computed tomography (CT), and ultrasound). Newer modalities such as optical imaging and new molecular imaging probes have the potential to revolutionize the way disease is detected, treated, and monitored.

In particular, optical imaging offers several advantages that make it a powerful molecular imaging approach, both in the research and clinical settings. Specifically, optical imaging can be fast, safe, cost effective and highly sensitive. Scan times are on the order of seconds to minutes, there is no need for ionizing radiation, and the imaging systems can be relatively simple to use. In addition, optical probes can be designed as dynamic molecular imaging agents that may alter their reporting profiles in vivo to provide molecular and functional information in real time. In order to achieve maximum penetration and sensitivity in vivo, the choice for most optical imaging in biological systems is within the red and near-infrared (NIR) spectral region (600-900 nm), although other wavelengths in the visible region can also be used. In the NIR wavelength range, absorption by physiologically abundant absorbers such as hemoglobin or water, as well as tissue autofluorescence, is minimized.

Hypoxia, or hypoxiation, is a pathological condition in which the body as a whole (generalized hypoxia) or a region of the body (tissue hypoxia) is deprived of adequate oxygen supply. Variations in arterial oxygen concentrations can be part of the normal physiology, for example, during strenuous physical exercise. A mismatch between oxygen supply and its demand at the cellular level may result in a hypoxic condition.

Tumor hypoxia is the situation where tumor cells have been deprived of oxygen. As a tumor grows, it rapidly outgrows its blood supply, leaving portions of the tumor with regions where the oxygen concentration is significantly lower than in healthy tissues. It can also be a result of the high degree of cell proliferation undergone in tumor tissue, causing a higher cell density, and thus taxing the local oxygen supply.

The carbonic anhydrases (or carbonate dehydratases) form a family of enzymes that catalyze the rapid interconversion of carbon dioxide and water to bicarbonate and protons (or vice-versa), a reversible reaction that occurs rather slowly in the absence of a catalyst. One of the functions of the enzyme in animals is to interconvert carbon dioxide and bicarbonate to maintain acid-base balance in blood and other tissues, and to help transport carbon dioxide out of tissues.

Carbonic anhydrases (CAs) are a large family of zinc metalloenzymes that participate in a variety of biological processes, including respiration, calcification, acid-base balance, bone resorption, and the formation of aqueous humor, cerebrospinal fluid, saliva, and gastric acid. They show extensive diversity in tissue distribution and in their subcellular localization. CA IX is a transmembrane protein that has been shown to be significantly upregulated under hypoxic conditions and plays a critical role, along with the intracellular carbonic anhydrase II, in hypoxia associated extracellular acidifcation. It is expressed in all clear-cell renal cell carcinoma, but is not detected in normal kidney or most other normal tissues. It may be involved in cell proliferation and transformation. Importantly, tumor hypoxia and subsequent expression of CA IX are associated with poor prognosis and treatment outcomes in numerous cancer types. The ability to more accurately and efficiently detect and quantify carbonic anhydrase-associated hypoxia will aid in the understanding of biological phenomena such as cellular proliferation and cancer, as well as in the determination of the most appropriate treatment regimens.

SUMMARY OF THE INVENTION

The invention provides fluorescent imaging agents that bind to carbonic anhydrase, in particular carbonic anhydrase IX (CA IX), and can be used in a variety of in vitro and in vivo applications, including but not limited to the identification of hypoxic cells such as would be found in hypoxic tumors. The invention also provides CA IX agents/ligands that are fluorescent in the far-red or near-infrared region that are of particular utility for in vivo imaging of carbonic anhydrase in live animals. In addition, the invention further provides agents that, independently, contain a far-red or near-infrared fluorophore that has been modified by a plurality of chemical modifying groups that can be used for optimization of in vitro and in vivo properties of the agent.

In one aspect, the carbonic anhydrase targeting agent comprises: a carbonic anhydrase binding moiety comprising a sulfonamide moiety optionally substituted with an aliphatic, aromatic or heteroaromatic moiety; and a fluorescent reporter chemically linked, optionally through a linker (L) moiety to the carbonic anhydrase moiety wherein the fluorescent moiety optionally further comprises a plurality of chemical modifying groups.

In another aspect, the invention comprises: (a) a carbonic anhydrase binding (CAB) moiety comprising a sulfonamide group and an aromatic or heteroaromatic moiety; (b) a far-red or near-infrared fluorophore (F) chemically linked, optionally through a linker (L) to the CAB moiety; and (c) a plurality of chemical modifiers (M), each independently and optionally linked to the fluorophore through a linker (L).

The chemical modifying moieties (M) can include, for example, two to eight individual modifying groups, each chemically linked to the fluorophore. Agents can comprise CAB, a fluorophore, and a plurality of modifying groups.

In certain embodiments, the carbonic anhydrase targeting agent is represented by formula (I), or a salt thereof:

$$\text{(I)}$$

wherein:
CAB is a carbonic anhydrase binding moiety comprising a sulfonamide and an aliphatic, aromatic or heteroaromatic moiety;
Q is a substituted or unsubstituted aryl, substituted or unsubstituted heteroaryl, $C_1$-$C_{18}$ alkyl, alkenyl, alkynyl, alkoxy, or thioalkyl group; or Q is absent;
$L_1$, $L_2$, and $L_3$ each represent independently for each occurrence a bond or a linker moiety;
W represents a benzo-condensed, a naphtho-condensed or a pyrido-condensed ring;
X is, independently for each occurrence, $C(CH_2Y_1)(CH_2Y_2)$, O, S, or Se;
$Y_1$ and $Y_2$ are independently hydrogen or a $C_1$-$C_{20}$ aliphatic group, each of which is optionally substituted with $L_3$-M;
M, independently for each occurrence, is hydrogen or a chemical modifying moiety.

In certain embodiments, the carbonic anhydrase targeting agent is represented by formula (II), or a salt thereof:

$$\text{(II)}$$

wherein:
CAB is a carbonic anhydrase binding moiety comprising a sulfonamide and an aliphatic,
aromatic or heteroaromatic moiety;
Q is a substituted or unsubstituted aryl, substituted or unsubstituted heteroaryl, $C_1$-$C_{18}$ alkyl, alkenyl, alkynyl, alkoxy, or thioalkyl group; or Q is absent;
$L_1$, $L_2$, and $L_3$ each represent independently for each occurrence a bond or a linker moiety;
R is, independently for each occurrence, hydrogen, substituted or unsubstituted aryl, substituted or unsubstituted heteroaryl, $C_1$-$C_{18}$ alkyl, alkenyl, alkynyl, alkoxy, or thioalkyl group, each of which is optionally substituted with $L_3$-M;
n is 1, 2, or 3;
W represents a benzo-condensed, a naphtho-condensed or a pyrido-condensed ring;
X is, independently for each occurrence, $C(CH_2Y_1)(CH_2Y_2)$, O, S, or Se;
$Y_1$ and $Y_2$ are independently hydrogen or a $C_1$-$C_{20}$ aliphatic group, each of which is optionally substituted with $L_3$-M; and
M, independently for each occurrence, is hydrogen or a chemical modifying moiety.

In certain embodiments, the carbonic anhydrase targeting agent comprises a compound of formula (III) or a salt thereof:

$$\text{F-L-CAB,} \qquad \text{(III)}$$

wherein
F is a near infrared fluorochrome;
L is an optional linker; and
CAB is a carbonic anhydrase binding moiety comprising a sulfonamide and an aliphatic, aromatic or heteroaromatic moiety.

In certain embodiments, the chemical modifying moiety, M is selected from hydrogen, alcohol, sulfonic acid, sulfonate, sulfonamide, sulfoxide, sulfone, carboxylate, ketone, phosphonate, phosphate; iminodiacetate, ethylenediamine tetraacetic acid, diethylenetriamine pentaacetic acid, tetraazacyclododecane tetraacetic acid, an amino acid, polyamino acid, oligo- or polyethylene glycol, amine, quaternary ammonium ion, glucosamine, galactosamine, or mannosamine. In other embodiments, the chemical modifying moiety, M is a carboxylate, phosphonate, phosphate, or iminodiacetate. In other embodiments, the chemical modifying moiety, M is a sulfonate.

In certain embodiments, certain M modifications of the compounds of the present invention result in fluorescent CA imaging agents that have higher selectivity for CA IX (relative to a CA other than CA IX (such as CA II)) than the CAB binding group not linked to the chemically modified fluorophore.

In certain embodiments, certain M modifications of the compounds of the present invention result in fluorescent CA imaging agents that do not nonspecifically cross cell membranes, thus enabling even greater selectivity for cell surface CAs over cytoplasmic CAs, such as CA II.

In certain embodiments, certain M modifications of the compounds of the present invention result in fluorescent CA imaging agents that have low nonspecific accumulation in animal tissues that are CA IX negative, thus enabling high contrast with respect to adjacent tissues that are CA IX positive.

In certain embodiments, the chemical modifying moiety, M, modifies the carbonic anhydrase targeting agent with a net negative charge ranging from −3 to −12 at neutral pH.

In certain embodiments, the chemical modifying moiety, M, reduces the nonspecific cell membrane permeability of the carbonic anhydrase targeting agent. Furthermore, in other embodiments, the chemical modifying moiety, M, reduces the nonspecific tissue accumulation of the carbonic anhydrase targeting agent when administered to a live animal.

In certain embodiments, the bond or linker moiety, L, comprises a moiety selected from the group consisting of glycine, alanine, β-alanine, —NH—$(CH_2)_n$—C(=O)— where n=1-8, 4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, and diamine-amino acids, such as homolysine, lysine, ornithine, diaminobutyric acid and diaminopropionic acid, succinic acid, glutaric acid, suberic acid, or adipic acid.

In certain embodiments, the carbonic anhydrase targeting moiety (CAB) in formula I, II or III is one of the following:

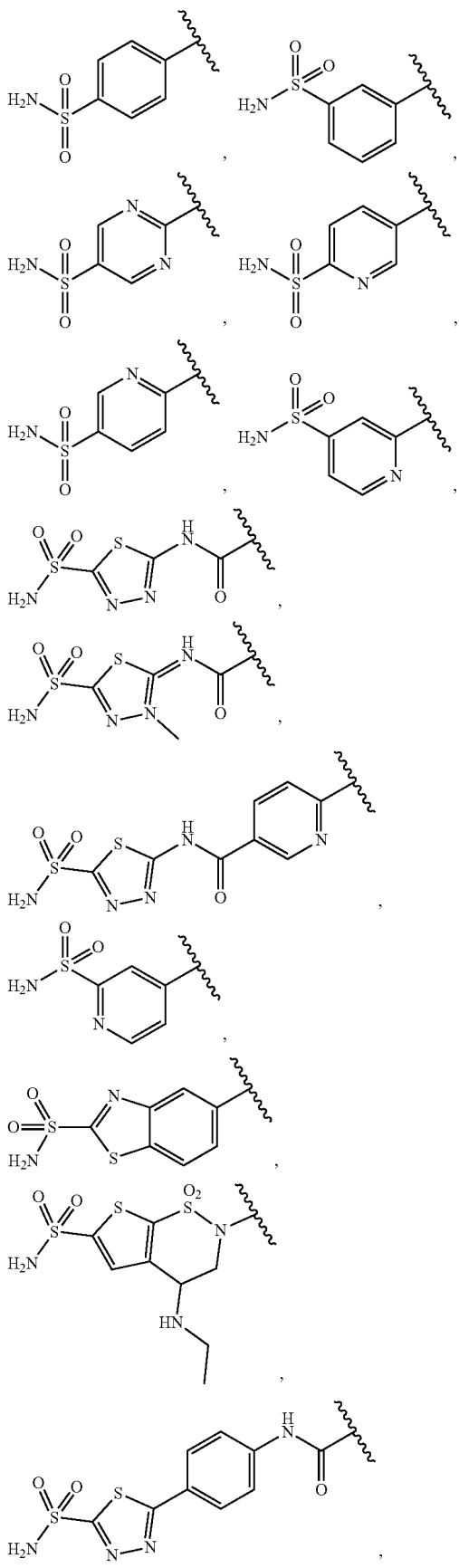

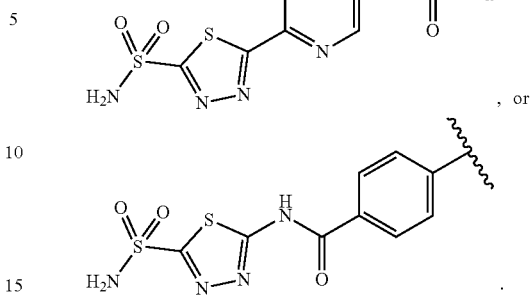

In certain embodiments, the carbonic anhydrase imaging agent is selected from the group consisting of:

3-ethyl-2-((1E,3Z,5E)-5-(3-ethyl-1,1-dimethyl-6,8-disulfo-1H-benzo[e]indol-2(3H)-ylidene)-3-(5-((4-sulfamoylbenzyl)carbamoyl)pyridin-2-yl)penta-1,3-dien-1-yl)-1,1-dimethyl-6,8-disulfo-1H-benzo[e]indol-3-ium;

3-(2-((1E,3Z,5E)-5-(1,1-dimethyl-6,8-disulfo-3-(3-sulfopropyl)-1H-benzo[e]indol-2(3H)-ylidene)-3-(5-((4-sulfamoylbenzyl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3E,5E)-5-(1,1-dimethyl-6,8-disulfo-3-(3-sulfopropyl)-1H-benzo[e]indol-2(3H)-ylidene)penta-1,3-dien-1-yl)-1,1-dimethyl-6-(N-methyl-N-(4-oxo-4-((4-sulfamoylbenzyl)amino)butyl)sulfamoyl)-1H-benzo[e]indol-3-ium-3-yl)propane-1-sulfonate;

3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-((4-sulfamoylbenzyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3Z,5E)-5-(1,1-dimethyl-6,8-disulfo-3-(3-sulfopropyl)-1H-benzo[e]indol-2(3H)-ylidene)-3-(5-((3-oxo-1-(4-sulfamoylphenyl)-6,9,12,15,18,21,24,27,30,33,36,39,42,45,48,51,54,57,60,63,66,69,72,75-tetracosaoxa-2-azaheptaheptacontan-77-yl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3E,5E)-5-(1,1-dimethyl-6,8-disulfo-3-(3-sulfopropyl)-1H-benzo[e]indol-2(3H)-ylidene)penta-1,3-dien-1-yl)-1,1-dimethyl-6-(N-methyl-N-(4-oxo-4-((4-((5-sulfamoyl-1,3,4-thiadiazol-2-yl)carbamoyl)benzyl)amino)butyl)sulfamoyl)-1H-benzo[e]indol-3-ium-3-yl)propane-1-sulfonate;

3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-((4-((5-sulfamoyl-1,3,4-thiadiazol-2-yl)carbamoyl)benzyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-ethyl-2-((1E,3Z,5E)-5-(3-ethyl-1,1-dimethyl-6,8-disulfo-1H-benzo[e]indol-2(3H)-ylidene)-3-(5-((4-((5-sulfamoyl-1,3,4-thiadiazol-2-yl)carbamoyl)benzyl)carbamoyl)pyridin-2-yl)penta-1,3-dien-1-yl)-1,1-dimethyl-8-sulfo-1H-benzo[e]indol-3-ium-6-sulfonate;

3-(2-((1E,3Z,5E)-5-(1,1-dimethyl-6,8-disulfo-3-(3-sulfopropyl)-1H-benzo[e]indol-2(3H)-ylidene)-3-(5-((4-((5-sulfamoyl-1,3,4-thiadiazol-2-yl)carbamoyl)benzyl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3Z,5E)-5-(1,1-dimethyl-6,8-disulfo-3-(3-sulfo-propyl)-1H-benzo[e]indol-2(3H)-ylidene)-3-(5-((3-oxo-1-(4-((5-sulfamoyl-1,3,4-thiadiazol-2-yl)carbamoyl)phenyl)-6,9,12,15,18,21,24,27,30,33,36,39,42,45,48,51,54,57,60,63,66,69,72,75-tetracosaoxa-2-azaheptaheptacontan-77-yl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3Z,5E)-5-(1,1-dimethyl-6,8-disulfo-3-(3-sulfo-propyl)-1H-benzo[e]indol-2(3H)-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-1,1-dimethyl-6,8-disulfo-1H-benzo[e]indol-3-ium-3-yl)propane-1-sulfonate; and 3-(2-((1E,3Z,5E)-5-(3,3-dimethyl-5-sulfo-1-(3-sulfopropyl)indolin-2-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-3,3-dimethyl-5-sulfo-3H-indol-1-ium-1-yl)propane-1-sulfonate; and pharmaceutically acceptable salts thereof.

Another aspect of the invention provides pharmaceutical composition suitable for administration to a subject, the pharmaceutical composition comprising a carbonic anhydrase targeting agent and a pharmaceutically acceptable excipient.

In certain embodiments, the invention provides a method of in vivo imaging, the method comprising: (a) administering to a subject a carbonic anhydrase targeting agent; (b) allowing the agent to distribute within the subject; and (c) detecting a signal emitted by the carbonic anhydrase targeting agent. In certain embodiments, steps (a)-(c) are repeated at predetermined time intervals thereby to permit evaluation of the emitted signals of the carbonic anhydrase targeting agent in the subject over time.

In certain embodiments, the invention provides a method of in vivo optical imaging, the method comprising: (a) administering to a subject a carbonic anhydrase targeting agent, wherein the agent comprises a fluorophore or fluorochrome; (b) allowing the agent to distribute within the subject; (c) exposing the subject to light of a wavelength absorbable by the fluorochrome; and (d) detecting a signal emitted by the agent. Furthermore, in other embodiments, steps (a)-(d) are repeated at predetermined time intervals thereby to permit evaluation of the emitted signals of the carbonic anhydrase agents in the subject over time.

In certain embodiments, the subject is an animal or a human.

In certain embodiments, the signal emitted by the agent is used to construct an image, for example, a tomographic image.

In certain embodiments, during step (a) two or more imaging probes whose signal properties are distinguishable from one another are administered to a subject, wherein at least one of the imaging probes is a carbonic anhydrase targeting agent. In other embodiments, in step (a), cells labeled with the carbonic anhydrase targeting agent are administered to the subject. In other embodiments, the signal emitted by the carbonic anhydrase targeting agent is used to monitor trafficking and localization of the cells.

In other embodiments, the illuminating and detecting steps are performed using an endoscope, catheter, tomographic system, hand-held optical imaging system, or an intraoperative microscope.

In certain embodiments, the presence, absence, or level of emitted signal is indicative of a disease state. In other embodiments, the method is used to detect and/or monitor a disease. In other embodiments, the disease is selected from the group consisting of bone disease, cancer, cardiovascular disease, atherosclerosis, restinosis, cardiac ischemia, myocardial reperfusion injury, environmental disease, dermatological disease, immunologic disease, inherited disease, infectious disease, inflammatory disease, metabolic disease, neurodegenerative disease, ophthalmic disease, and respiratory disease.

In certain embodiments, the invention is a method of imaging hypoxia in a subject, the method comprising the steps of: (a) administering a carbonic anhydrase targeting agent to a subject; and (b) detecting the presence of the agent thereby to produce an image representative of deficient oxygen in the subject's tissues. In certain embodiments, carbonic anhydrase agent signal in a tumor is representative of a hypoxic tumor.

In certain embodiments, the invention is a method of treating a disease in a subject comprising administering to a subject, either systemically or locally, a carbonic anhydrase targeting agent, wherein the agent comprises a radiolabel that localizes in the disease area and delivers an effective dose of radiation.

In certain embodiments, the invention is an in vitro imaging method, the method comprising: (a) contacting a sample with a carbonic anhydrase targeting agent; (b) allowing the agent to bind to a biological target; (c) optionally removing unbound agent; and (d) detecting signal emitted from the agent thereby to determine whether the agent has been activated by or bound to the biological target. In other embodiments, the sample is a biological sample.

In certain embodiments, the carbonic anhydrase targeting agent is fluorescent in the far-red or near-infrared.

The compounds of the present invention are efficacious for the inhibition of CAs, especially CA IX, as well as for in vitro and in vivo fluorescence imaging of CAs and therefore can be used for both therapeutic and diagnostic applications.

In addition, the invention provides methods for in vitro and in vivo imaging using the fluorescent CA imaging agents. With respect to optical in vivo imaging, the method comprises (a) administering to a subject CA agents of the invention; (b) allowing the CA agents to distribute within the subject; (c) exposing the subject to light of a wavelength absorbable by the fluorophore of the CA agent; and (d) detecting an optical signal emitted by the CA agent. The signal emitted by the agent can be used to construct an image. In certain embodiments, certain of the images are a tomographic image. Furthermore, it is understood that the foregoing steps can be repeated at predetermined intervals thereby permitting evaluation of the subject over time.

The carbonic anhydrase targeting agents can be formulated into a pharmaceutical composition suitable for administration to a subject, for example, an animal and/or a human subject. The pharmaceutical composition can include one or more of the carbonic anhydrase agents and one or more stabilizers in a physiologically acceptable carrier.

The subject may be a vertebrate, for example, a mammal, for example, a human. The subject may also be a non-vertebrate (for example, *C. elegans, drosophila*, or another model research organism, etc.) used in laboratory research.

The carbonic anhydrase targeting agent, can include, for example, one to five carbonic anhydrase binding moieties (for example, from two to five, three to five, or four to five carbonic anhydrase binding moieties), each chemically linked to the imaging reporter. The agents can comprise a plurality of carbonic anhydrase binding moieties each chemically linked to the imaging reporter.

Imaging reporters can be chosen, for example, from a fluorophore reporter, a fluorochrome reporter, an optical reporter, a magnetic reporter, a radiolabel, an X-ray reporter, an ultrasound imaging reporter or a nanoparticle-based reporter or combination. The carbonic anhydrase agent can further comprise a biological modifier chemically linked to the carbonic anhydrase binding moiety or to the imaging reporter.

In addition, the present invention provides methods for in vitro and in vivo imaging using the carbonic anhydrase targeting agents. With respect to optical in vivo imaging, one exemplary method comprises (a) administering to a subject one or more of the foregoing carbonic anhydrase targeting agents of the invention, wherein the agents comprise one or more fluorochromes; (b) allowing the agent to distribute within the subject; (c) exposing the subject to light of a wavelength absorbable by at least one fluorochrome; and (d) detecting a signal emitted by the carbonic anhydrase targeting agent. The signal emitted by the agent can be used to construct an image, for example, a tomographic image. Furthermore, it is understood that the foregoing steps can be repeated at predetermined intervals, which permit evaluation of the subject over time.

The carbonic anhydrase targeting agents can be used to measure tumor hypoxia (oxygen defficiency) or other physiological processes such as cellular proliferation in a subject. One exemplary method comprises (a) administering one or more of the foregoing carbonic anhydrase targeting agents to a subject; (b) detecting the presence of the agent(s) thereby to produce an image representative of tumors with reduced oxygen concentration in the subject.

In each of the foregoing methods, the subject can be a vertebrate, for example, a mammal, for example, a human. The subject also can be a non-vertebrate (for example, *C. elegans, drosophila*, or another model research organism, etc.) used in laboratory research.

In addition, the carbonic anhydrase targeting agents can be incorporated into a kit, for example, a kit with optional instructions for using the carbonic anhydrase targeting agents in in vivo or in vitro imaging methods. The kit optionally can include components that aid in the use of the carbonic anhydrase targeting agents, for example, buffers, and other formulating agents. Alternatively, the kit can include medical devices that aid in the administration and/or detection of the carbonic anhydrase targeting agents to subjects.

Other features and advantages of the invention will be apparent from the following figures, detailed description, and the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
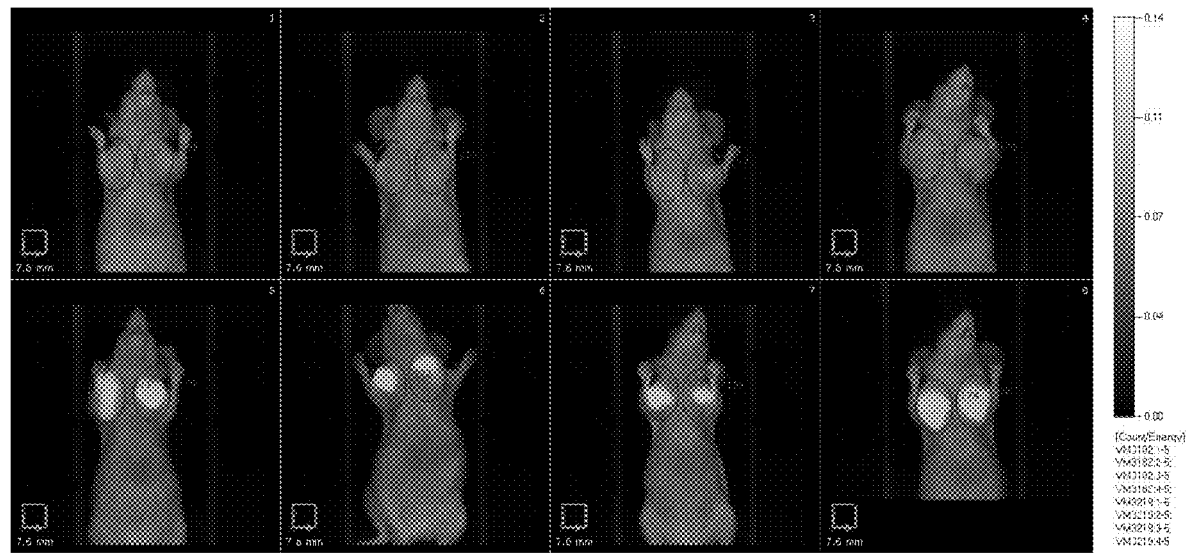
FIGS. 1A-B depict planar reflectance (FIG. 1A) and tomographic (FIG. 1B) images of bilateral HeLa tumors at 24 h after administration of nonbinding control compound D3 (top row of each image set) and exemplary compound C5 (bottom row of each image set)

The invention is based, in part, upon the discovery that it is possible to produce stable, biocompatible fluorescent agents that target carbonic anhydrase (CA), exhibit low nonspecific cellular uptake in vitro and low nonspecific tissue uptake in vivo, and can be used in a variety of in vitro and in vivo assays and imaging applications, as well as in a variety of therapeutic applications. The fluorescent agents can bind to the enzyme carbonic anhydrase, which often is upregulated during hypoxia.

Certain fluorophores, such as cyanine fluorophores with absorbance and emission spectra in the far-red and near-infrared regions, can have molecular weights that far exceed the molecular weights of binding groups, such as carbonic anhydrase binding groups, and can have a dominant effect on the physical, chemical, and biological properties of an agent when linked to a binding group, which can negatively impact in vitro and in vivo imaging performance. Chemical modification of the fluorophore moiety can overcome these limitations by allowing manipulation of the physical, chemical and biological properties of the agent without directly modifying the binding group. Further, the chemical modifying moieties can influence binding affinity, binding selectivity among multiple enzymes, and the nonspecific uptake of the agent in cells or tissues that are otherwise negative with respect to the binding target. In particular, modification of a cyanine dye in such a manner as to impart a significant net negative charge at physiological pH of, for example net charge of −3 to −6, can render a CA IX agent impermeable to CA IX negative cells and favor rapid clearance from CA IX negative tissues in vivo. In certain embodiments, the agents modified to have net negative charge of −3 to −6 at neutral pH show unexpectedly high performance with respect to binding affinity and target to background ratios in both in vitro and in vivo experiments.

In one aspect, the agents of the present invention comprise at least one carbonic anhydrase binding moiety (CAB) chemically linked to a fluorophore, wherein one or more chemical modifying moieties (M) are chemically linked to the fluorophore. Optionally, one or more linker (L) moieties can be used to chemically link the CAB to the fluorophore or the M to the fluorophore. In some embodiments, the CAB is a molecule containing a sulfonamide and an aromatic or heteroaromatic moiety, and the fluorophore is a cyanine dye.

A "carbonic anhydrase binding moiety" or CAB, as defined herein, is a molecule that specifically binds a carbonic anhydrase and/or reduces or prevents the catalytic activity of a carbonic anhydrase toward a natural substrate for carbonic anhydrase, and/or antagonizes the binding of a carbonic anhydrase to its natural ligand. The binding between a CAB and a carbonic anhydrase may be covalent or non-covalent (for example, electrostatic interactions, hydrophobic interactions, van der Waals interactions, hydrogen bonding, dipole interactions, etc.). The binding between a CAB and a carbonic anhydrase preferably is non-covalent.

In certain embodiments, the CAB has an affinity for a carbonic anhydrase, for example CA II, CA IV, CA IX, and CA XII.

The term "affinity" as used herein, refers to the ability of the carbonic anhydrase agent to bind preferentially to and/or be retained by a carbonic anhydrase enzyme. Carbonic anhydrase agents with this characteristic are "targeted." Affinity of a CAB or carbonic anhydrase agent can be measured, for example, by determining inhibition constant $K_i$ towards a CA enzyme by measuring inhibition of activity of the CA enzyme for a substrate (e.g., $CO_2$) in the presence of the agent or, in the case of membrane bound CAs such as CA IX, by measuring the dissociation constant $K_d$ to live CA expressing cells by, for example, flow cytometry. In certain embodiments, the affinity of the carbonic anhydrase targeted agents described herein have a $K_i$ or $K_d$ to a CA of less than 100 nM. In certain preferred embodiments, the $K_i$ or $K_d$ of the agents described herein toward CA IX is less than 50 nM.

It is understood that the carbonic anhydrase targeting agents disclosed herein also include stereoisomeric forms thereof, or mixtures of stereoisomeric forms thereof, or pharmaceutically acceptable salt forms thereof.

The "fluorophore" (F) may be any suitable chemical or substance which is used to provide fluorescent signal or contrast in imaging and that is detectable by imaging techniques. In certain embodiments, F comprises, for example, a cyanine dye, carbocyanine dye, indocyanine dye, or a polymethine fluorescent dye.

In certain embodiments, F comprises a symmetrical cyanine dye. In other embodiments, F comprises a non-symmetrical cyanine dye. In other embodiments, F may also be modified with a plurality of chemical modifying moieties allowing optimization of the in vitro and in vivo properties of the agent, and ultimately the performance of the agent as a fluorescence imaging agent.

As used herein, the term "chemically linked" is understood to mean connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions.

As used herein, the term "functionality" is understood to mean a reactive functional group that can be further modified or derivatized with another molecule. In one aspect, the reactive functional group is an amine, carboxylic acid, carboxylic ester, halogen, hydrazine, hydroxylamine, nitrile, isonitrile, isocyanate, isothiocyanate, thiol, maleimide, azide, alkyne, tetrazolyl, phosphonate, alkene, nitro, and nitroso.

As used herein, the term "chemical modifying group" or "M" is understood to mean any moiety that can be used to alter the physical, chemical or biological properties of the carbonic anhydrase targeting agent, such as, without limitation, making the targeting agent more water soluble or more dispersible in media for administration, increasing binding specificity, increasing or decreasing net molecular charge, decreasing immunogenicity or toxicity, or modifying cell uptake, pharmacokinetic or biodistribution profiles compared to the non-M modified carbonic anhydrase agents.

The "imaging reporter" or "IR" can be any suitable chemical or substance which is used to provide the contrast or signal in imaging and that is detectable by imaging techniques. In certain preferred embodiments, the imaging reporter comprises one or more fluorophores, photoluminescent nanoparticles, radioisotopes, superparamagnetic agents, X-ray contrast agents, and ultrasound agents. It is understood that the IR can also comprise a therapeutic reporter such as a porphyrin used in photodynamic therapy and/or a radionuclide used in radiotherapy.

The term "alkyl" is art-recognized, and includes saturated aliphatic groups, including straight-chain alkyl groups, and branched-chain alkyl groups. Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. In certain embodiments, the alkyl is not substituted, i.e., it is unsubstituted. In instances where the term "alkyl" is used to describe a chemical fragment that connects two portions of a compound, the term "alkyl" is understood to mean a diradical of a saturated aliphatic group, including a diradical of a straight-chain alkyl group, and diradical of branched-chain alkyl group. To illustrate, the term alkyl in "Br-alkyl-$CO_2H$" refers to an alkyl diradical that connects the bromine and carboxylic acid groups.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls. In certain embodiments, the aryl is not substituted, i.e., it is unsubstituted. In instances where the term "aryl" is used to describe a chemical fragment that connects two portions of a compound, the term "aryl" is understood to mean a diradical of an aromatic group. To illustrate, the term aryl in "Br-aryl-CO₂H" refers to an aryl diradical that connects the bromine and carboxylic acid groups.

Terms "heterocyclic" and "heterocyclyl" are art recognized and refer to an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to, furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO₂alkyl, carbonyl, carboxyl, alkylthio, sulfonyl, sulfonamido, sulfonamide, ketone, aldehyde, ester, heterocyclyl, aryl or heteroaryl moieties, —CF₃, —CN, or the like. In certain embodiments, the heterocyclic or heterocyclyl group is not substituted, i.e., it is unsubstituted. In instances where the term "heterocyclyl" is used to describe a chemical fragment that connects two portions of a compound, the term "heterocyclyl" is understood to mean a diradical of an aromatic or nonaromatic ring containing one or more heteroatoms. To illustrate, the term heterocyclyl in "Br-heterocyclyl-CO₂H" refers to a heterocyclyl diradical that connects the bromine and carboxylic acid groups.

The terms "amine" and "amino" are art-recognized and refer to both unsubstituted and substituted amines, e.g., a moiety that may be represented by the general formulas:

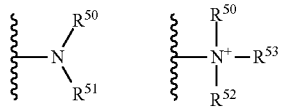

wherein $R^{50}$, $R^{51}$, $R^{52}$ and $R^{53}$ each independently represent a hydrogen, an alkyl, an alkenyl, —(CH₂)$_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH₂)$_m$—$R^{61}$.

The term "oxo" is art-recognized and refers to a "=O" substituent. For example, a cyclopentane substituted with an oxo group is cyclopentanone.

The symbol "~~~" indicates a point of attachment.

Compounds described herein may contain charged functional groups, such as a —SO₃⁻ group. It is understood that compounds containing such charged functional groups contain either (i) a sufficient number of positively charged functional group(s) and negatively charged functional groups so as to provide a charge-neutral compound, or (ii) one or more counterions is present so that the compound is charge-neutral. If a chemical structure is presented that would have an overall charge (as depicted) it is understood that a sufficient number of counterion(s) (e.g., a halogen or acetate to counterbalance a positive charge, or a metal cation or ammonium group to counter-balance a negative charge) are present so as to provide a charge-neutral compound. Further, all tautomers of compounds depicted herein all within the scope of the invention.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

Various compounds are described by chemical structure and/or chemical names. In the event a discrepancy exists between a chemical structure and the chemical name provided for the structure, the chemical structure predominates.

As a general matter, compositions specifying a percentage are by weight unless otherwise specified. Further, if a variable is not accompanied by a definition, then the previous definition of the variable controls.

In one aspect, the invention provides a carbonic anhydrase targeting agent comprising: a carbonic anhydrase targeting moiety comprising a sulfonamide moiety optionally substituted with an aliphatic, aromatic or heteroaromatic moiety; and a fluorescent reporter chemically linked, optionally through a linker (L) moiety to the carbonic anhydrase moiety wherein the fluorescent moiety bears a plurality of chemical modifying groups.

In another aspect, the invention provides a carbonic anhydrase targeting agent comprising: (a) a carbonic anhydrase targeting moiety comprising a sulfonamide moiety optionally substituted with an aliphatic, aromatic or heteroaromatic moiety; and (b) an imaging reporter chemically linked, optionally through a linker (L) moiety to the carbonic anhydrase moiety.

In another aspect, the invention provides a carbonic anhydrase targeting agent represented by formula (I), or a salt thereof:

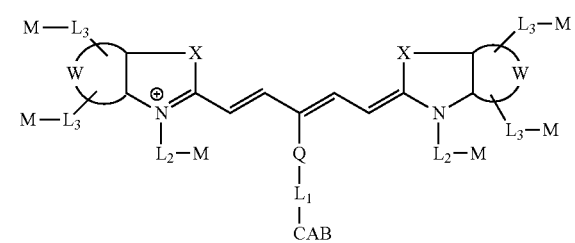

wherein:
CAB is a carbonic anhydrase binding moiety comprising a sulfonamide and an aliphatic, aromatic or heteroaromatic moiety;
Q is a substituted or unsubstituted aryl, substituted or unsubstituted heteroaryl, C₁-C₁₈ alkyl, alkenyl, alkynyl, alkoxy, or thioalkyl group; or Q is absent;
L₁, L₂, and L₃ each represent independently for each occurrence a bond or a linker moiety;

W represents a benzo-condensed, a naphtho-condensed or a pyrido-condensed ring;

X is, independently for each occurrence, $C(CH_2Y_1)(CH_2Y_2)$, O, S, or Se;

$Y_1$ and $Y_2$ are independently hydrogen or a $C_1$-$C_{20}$ aliphatic group, each of which is optionally substituted with $L_3$-M;

M, independently for each occurrence, is hydrogen or a chemical modifying moiety.

In another aspect, the invention provides a carbonic anhydrase targeting agent represented by formula (II), or a salt thereof:

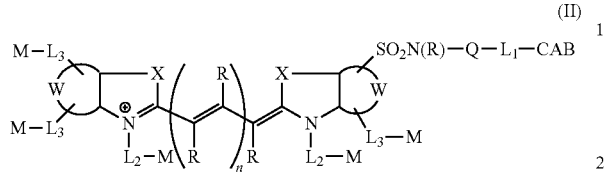

(II)

wherein:

CAB is a carbonic anhydrase binding moiety comprising a sulfonamide and an aliphatic, aromatic or heteroaromatic moiety;

Q is a substituted or unsubstituted aryl, substituted or unsubstituted heteroaryl, $C_1$-$C_{18}$ alkyl, alkenyl, alkynyl, alkoxy, or thioalkyl group; or Q is absent;

$L_1$, $L_2$, and $L_3$ each represent independently for each occurrence a bond or a linker moiety;

R is, independently for each occurrence, hydrogen, substituted or unsubstituted aryl, substituted or unsubstituted heteroaryl, $C_1$-$C_{18}$ alkyl, alkenyl, alkynyl, alkoxy, or thioalkyl group, each of which is optionally substituted with $L_3$-M;

n is 1, 2, or 3;

W represents a benzo-condensed, a naphtho-condensed or a pyrido-condensed ring;

X is, independently for each occurrence, $C(CH_2Y_1)(CH_2Y_2)$, O, S, or Se;

$Y_1$ and $Y_2$ are independently hydrogen or a $C_1$-$C_{20}$ aliphatic group, each of which is optionally substituted with $L_3$-M; and M, independently for each occurrence, is hydrogen or a chemical modifying moiety.

In another aspect, the invention provides a carbonic anhydrase targeting agent of formula (III) or a salt thereof:

F-L-CAB, (III)

wherein

F is a near infrared fluorochrome;

L is an optional linker; and

CAB is a carbonic anhydrase binding moiety comprising a sulfonamide and an aliphatic, aromatic or heteroaromatic moiety.

In another aspect, the invention provides a carbonic anhydrase targeting agent represented by formula (IV), or a salt thereof:

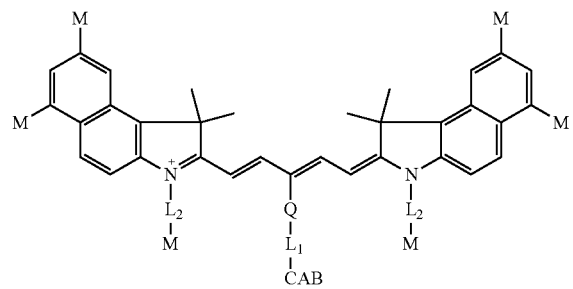

(IV)

wherein:

Q is unsubstituted heteroaryl;

$L_1$ is one of the following:
  (a) —C(O)N($R^1$)-alkyl-C(O)N($R^1$)-ψ;
  (b) —C(O)N($R^1$)-alkyl-ψ;
  (c) —C(O)N($R^1$)—[$C_{2-3}$ alkyl-O]$_z$—$C_{1-3}$alkyl-C(O)N($R^1$)-ψ;
  (d) —C(O)N($R^1$)-alkyl-aryl-C(O)N($R^1$)-ψ;
  (e) —C(O)N($R^1$)-alkyl-C(O)N($R^1$)—$C_{1-3}$alkyl-aryl-C(O)N($R^1$)-ψ; or
  (f) —C(O)N($R^1$)—[$C_{2-3}$ alkyl-O]$_z$—$C_{1-3}$alkyl-C(O)N($R^1$)-alkyl-aryl-C(O)N($R^1$)-ψ;

wherein z is an integer from about 3 to about 35, $R^1$ represents independently for each occurrence hydrogen or alkyl, and ψ is a bond to CAB;

$L_2$ is $C_{1-5}$alkyl;

M represents independently for each occurrence sulfonate or —$SO_3H$; and

CAB is -aryl-$SO_2NH_2$, -heterocyclyl-$SO_2NH_2$, -aryl-C(O)N(R')-heteroaryl-$SO_2NH_2$, -heteroaryl-C(O)N(R')-heteroaryl-$SO_2NH_2$, —C(O)N(R')-heteroaryl-heteroaryl-$SO_2NH_2$, or —C(O)N(R')-aryl-heteroaryl-$SO_2NH_2$, wherein R' represents independently for each occurrence hydrogen or $C_{1-6}$ alkyl; each aryl and heteroaryl are optionally substituted with 1 or 2 substituents independently selected from the group consisting of alkyl and halogen, and each heterocyclyl is optionally substituted with 1, 2, or 3 substituents independently selected from the group consisting of alkyl, halogen, amino, and oxo.

In another aspect, the invention provides a carbonic anhydrase targeting agent represented by formula (V), or a salt thereof:

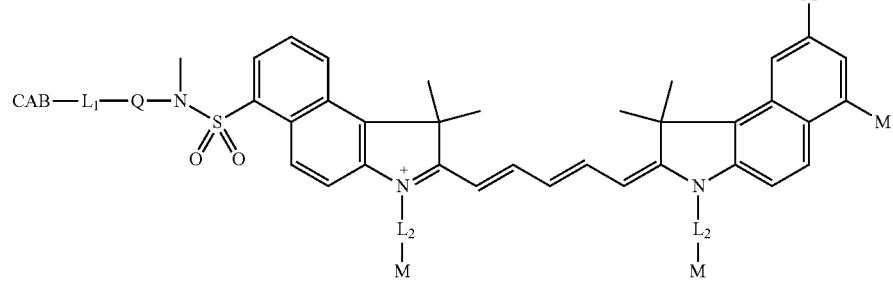

(V)

wherein:

Q is $C_{1-6}$alkyl;

$L_1$ is one of the following:
(a) —C(O)N($R^1$)-alkyl-C(O)N($R^1$)-ψ;
(b) —C(O)N($R^1$)-alkyl-ψ; or
(c) —C(O)N($R^1$)-alkyl-aryl-C(O)N($R^1$)-ψ;
  wherein $R^1$ represents independently for each occurrence hydrogen or alkyl, and ψ is a bond to CAB;

$L_2$ is $C_{1-5}$alkyl;

M represents independently for each occurrence sulfonate or —$SO_3H$; and

CAB is -aryl-$SO_2NH_2$, -heterocyclyl-$SO_2NH_2$, -aryl-C(O)N(R')-heteroaryl-$SO_2NH_2$, -heteroaryl-C(O)N(R')-heteroaryl-$SO_2NH_2$, —C(O)N(R')-heteroaryl-heteroaryl-$SO_2NH_2$, or —C(O)N(R')-aryl-heteroaryl-$SO_2NH_2$, wherein R' represents independently for each occurrence hydrogen or $C_{1-6}$ alkyl; each aryl and heteroaryl are optionally substituted with 1 or 2 substituents independently selected from the group consisting of alkyl and halogen, and each heterocyclyl is optionally substituted with 1, 2, or 3 substituents independently selected from the group consisting of alkyl, halogen, amino, and oxo.

In another aspect, the invention provides a carbonic anhydrase targeting agent represented by formula (VI), or a salt thereof:

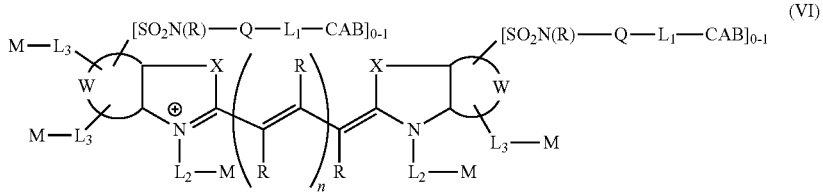

(VI)

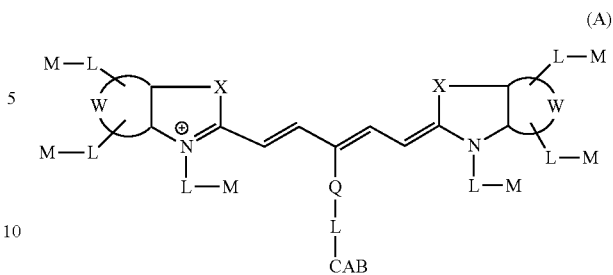

(A)

wherein CAB is a carbonic anhydrase targeting moiety comprising a sulfonamide and an aliphatic, aromatic or heteroaromatic moiety;

L is, independently for each occurrence, a bond or a linker moiety;

Q is selected from a group consisting of substituted or unsubstituted aryl, substituted or unsubstituted heteroaryl, $C_1$-$C_{18}$ alkyl, alkenyl, alkynyl, alkoxy, and a thioalkyl group;

W represents a benzo-condensed, a naphtho-condensed or a pyrido-condensed ring;

X is, independently for each occurrence, selected from the group consisting of $C(CH_2Y_1)(CH_2Y_2)$, O, S, and Se;

$Y_1$ and $Y_2$ are independently selected from the group consisting of H, and $C_1$-$C_{20}$ aliphatic group, each of which is optionally substituted with L-M; and M, independently for each occurrence, is a chemical modifying moiety or is absent.

In another aspect, the invention provides a compound of formula (B), or a salt thereof:

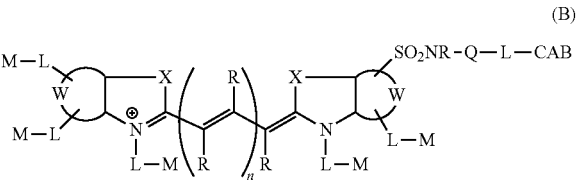

(B)

wherein:

CAB is a carbonic anhydrase binding moiety comprising a sulfonamide and an aliphatic, aromatic or heteroaromatic moiety;

Q is a substituted or unsubstituted aryl, substituted or unsubstituted heteroaryl, $C_1$-$C_{18}$ alkyl, alkenyl, alkynyl, alkoxy, or thioalkyl group; or Q is absent; $L_1$, $L_2$, and $L_3$ each represent independently for each occurrence a bond or a linker moiety;

R is, independently for each occurrence, hydrogen, substituted or unsubstituted aryl, substituted or unsubstituted heteroaryl, $C_1$-$C_{18}$ alkyl, alkenyl, alkynyl, alkoxy, or thioalkyl group, each of which is optionally substituted with $L_3$-M;

n is 1, 2, or 3;

W represents a benzo-condensed, a naphtho-condensed or a pyrido-condensed ring;

X is, independently for each occurrence, $C(CH_2Y_1)(CH_2Y_2)$, O, S, or Se;

$Y_1$ and $Y_2$ are independently hydrogen or a $C_1$-$C_{20}$ aliphatic group, each of which is optionally substituted with $L_3$-M;

M, independently for each occurrence, is hydrogen or a chemical modifying moiety; and provided that there is at least one occurrence of CAB.

In another aspect, the invention provides a compound of formula (A) or a salt thereof:

wherein CAB is a carbonic anhydrase binding moiety comprising a sulfonamide and an aliphatic, aromatic or heteroaromatic moiety;

L is, independently for each occurrence, a bond or a linker moiety;

Q is selected from a group consisting of substituted or unsubstituted aryl, substituted or unsubstituted heteroaryl, $C_1$-$C_{18}$ alkyl, alkenyl, alkynyl, alkoxy, and thioalkyl group, or Q is absent;

R is, independently for each occurrence, substituted or unsubstituted aryl, substituted or unsubstituted heteroaryl, $C_1$-$C_{18}$ alkyl, alkenyl, alkynyl, alkoxy, or thioalkyl group, each of which is optionally substituted with L-M, or R is absent;

n is 1, 2, or 3;

W represents a benzo-condensed, a naphtho-condensed or a pyrido-condensed ring;

X is, independently for each occurrence, selected from the group consisting of $C(CH_2Y_1)(CH_2Y_2)$, O, S, and Se;

$Y_1$ and $Y_2$ are independently selected from the group consisting of H and $C_1$-$C_{20}$ aliphatic group, each of which is optionally substituted with L-M; and M, independently for each occurrence, is a chemical modifying moiety or is absent.

Chemical Modifier M

The chemical modifier M can be an anionic moiety selected from the group consisting of a sulfonate, a carboxylate, phosphonate, phosphate, or iminodiacetate.

The chemical modifier M can be a hydrogen, alcohol, sulfonamide, sulfoxide, sulfone, ketone, an amino acid or polyamino acid, oligo- or polyethylene glycol, an amine, a quaternary ammonium ion, or a sugar such as glucosamine, galactosamine or mannosamine.

The chemical modifier M can be a metal chelator, such as ethylenediamine tetraacetic acid, diethylenetriamine pentaacetic acid, and tetraazacyclododecane tetraacetic acid. In another aspect of the invention, one or more metal chelating M groups are coordinated to a metal ion.

The chemical modifier M can be an ionizable group, for example, a carboxylate, sulfonate, phosphonate, phosphate or iminodiacetate, that impart a significant net negative charge on the agent. In certain embodiments, the net charge on the agent after chemical modification of the fluorophore with a plurality of ionizable modifying groups, is between −3 and −12 at neutral pH. In certain embodiments, the net charge on the fluorophore moiety is −5.

In certain embodiments, the chemical modifier M comprises a biologically active molecule, such as a drug or a radiotherapeutic moiety. In certain embodiments the biologically active molecule is linked to the agent through a linker that is cleavable through a biological or physical mechanism including but not limited to enzymatic, thermal, acid catalyzed or photochemical cleavage.

In certain embodiments, M represents independently for each occurrence a sulfonate or —$SO_3H$. In certain embodiments, M represents independently for each occurrence hydrogen, a sulfonate, or —$SO_3H$.

In certain embodiments M represents independently for each occurrence a substituent selected from the group consisting of hydrogen, alcohol, sulfonic acid, sulfonate, polysulfonate, cysteic acid, sulfonamide, sulfoxide, sulfone, carboxylate, ketone, phosphonate, phosphate; iminodiacetate, ethylenediamine tetraacetic acid, diethylenetriamine pentaacetic acid, tetraazacyclododecane tetraacetic acid, an amino acid or polyamino acid, oligo- or polyethylene glycol, amine, quaternary ammonium ion, a sugar, glucosamine, galactosamine, mannosamine, polyethylene glycol (PEG), alkoxy polyethylene glycol, a branched polypropylene glycol, polypropylene glycol, a graft copolymer of poly-lysine and methoxypolyethyleneglycol, peptide, a lipid, a fatty acid, palmitate, phospholipid, a phospholipid-PEG conjugate, a carbohydrate, an iron oxide nanoparticle, naphthylalanine, phenylalanine, 3,3-diphenylpropylamine, taurine, a phosphonate, a phosphate, a carboxylate, and a polycarboxylate.

In certain embodiments, M represents independently for each occurrence hydrogen or —$N(C_{1-4}$ alkyl-$SO_3H)_2$.

In certain embodiments, the chemical modifying moiety M enhances the binding selectivity of the carbonic anhydrase targeting agent for carbonic anhydrase IX over other carbonic anhydrases including but not limited to carbonic anhydrase II. In certain embodiments, the chemical modifying moiety M modifies the carbonic anhydrase targeting agent with a net negative charge ranging from −3 to −12 at neutral pH. In certain embodiments, the chemical modifying moiety M reduces the nonspecific cell membrane permeability of the carbonic anhydrase targeting agent. In certain other embodiments, the chemical modifying moiety M reduces the nonspecific tissue accumulation of the carbonic anhydrase targeting agent when administered to a live animal.

Linker Moiety

In certain embodiments, the linker moiety, L, comprises a moiety selected from the group consisting of glycine, alanine, β-alanine, —NH—$(CH_2)_n$—C(=O)— where n=1-8, 4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, and diamine-amino acids, such as homolysine, lysine, ornithine, diaminobutyric acid and diaminopropionic acid, succinic acid, glutaric acid, suberic acid, and adipic acid. In certain embodiments, L is a bond.

In certain other embodiments, each of $L_1$, $L_2$, and $L_3$ independently comprises —NH—$(CH_2)_n$—C(=O)— where n=1-8, or a diradical of a moiety selected from the group consisting of glycine, alanine, β-alanine, 4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, a diamine-amino acid, lysine, ornithine, diaminobutyric acid, diaminopropionic acid, succinic acid, glutaric acid, suberic acid, adipic acid, amide, triazole, urea, and thiourea.

In certain embodiments, $L_1$ is one of the following: (a) —C(O)N($R^1$)-alkyl-C(O)N($R^1$)-ψ; (b) —C(O)N($R^1$)-alkyl-ψ; (c) —C(O)N($R^1$)—[$C_{2-3}$ alkyl-O]$_z$—$C_{1-3}$ alkyl-C(O)N($R^1$)-ψ; (d) —C(O)N($R^1$)-alkyl-aryl-C(O)N($R^1$)-ψ; (e) —C(O)N($R^1$)-alkyl-C(O)N($R^1$)—$C_{1-3}$ alkyl-aryl-C(O)N($R^1$)-ψ; or (f) —C(O)N($R^1$)—[$C_{2-3}$ alkyl-O]$_z$—$C_{1-3}$ alkyl-C(O)N($R^1$)-alkyl-aryl-C(O)N($R^1$)-ψ; wherein z is an integer from about 3 to about 35, $R^1$ represents independently for each occurrence hydrogen or alkyl, and ψ is a bond to CAB.

In certain embodiments, $L_2$ is $C_{1-5}$alkyl. In certain embodiments, $L_3$ is a bond.

In certain embodiments, $L_2M$ is —$(CH_2)_{0-3}CH_3$.

Variable Q

In certain embodiments, Q can be selected from the group consisting of (i) a functionalized, substituted or unsubstituted aromatic or heteroaromatic ring, (ii) a functionalized, substituted or unsubstituted nitrogen containing heterocyclic ring, (iii) a functionalized, substituted or unsubstituted nitrogen containing 6-membered heterocyclic ring, such as pyridine, pyrimidone, pyrazine, and pyridazine, (iv) functionalized, substituted or unsubstituted 6-membered aromatic ring, such as benzene, (v) a functionalized, substituted or unsubstituted $C_1$-$C_{18}$alkyl, alkenyl, alkynyl, alkoxy, or thioalkyl group. In other embodiments, Q is absent.

In certain embodiments, Q is unsubstituted heteroaryl, such as pyridinyl. In certain other embodiments, Q is alkyl, such as $C_{1-4}$ alkyl.

Exemplary Specific Carbonic Anhydrase Targeting Agents

The carbonic anhydrase targeting agent can be selected from the group comprising:

3-ethyl-2-((1E,3Z,5E)-5-(3-ethyl-1,1-dimethyl-6,8-disulfo-1H-benzo[e]indol-2(3H)-ylidene)-3-(5-((4-sulfamoyl-benzyl)carbamoyl)pyridin-2-yl)penta-1,3-dien-1-yl)-1,1-dimethyl-6,8-disulfo-1H-benzo[e]indol-3-ium;

3-(2-((1E,3Z,5E)-5-(1,1-dimethyl-6,8-disulfo-3-(3-sulfo-propyl)-1H-benzo[e]indol-2(3H)-ylidene)-3-(5-((4-sulfa-moylbenzyl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3E,5E)-5-(1,1-dimethyl-6,8-disulfo-3-(3-sulfo-propyl)-1H-benzo[e]indol-2(3H)-ylidene)penta-1,3-dien-1-yl)-1,1-dimethyl-6-(N-methyl-N-(4-oxo-4-((4-sulfa-moylbenzyl)amino)butyl)sulfamoyl)-1H-benzo[e]indol-3-ium-3-yl)propane-1-sulfonate;

3-(2-((1E,3Z,5E)-5-(1,1-dimethyl-6,8-disulfo-3-(3-sulfo-propyl)-1H-benzo[e]indol-2(3H)-ylidene)-3-(5-((6-oxo-6-((4-sulfamoylbenzyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3Z,5E)-5-(1,1-dimethyl-6,8-disulfo-3-(3-sulfo-propyl)-1H-benzo[e]indol-2(3H)-ylidene)-3-(5-((3-oxo-1-(4-sulfamoylphenyl)-6,9,12,15,18,21,24,27,30,33,36,39,42,45,48,51,54,57,60,63,66,69,72,75-tetracosaoxa-2-azaheptaheptacontan-77-yl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3E,5E)-5-(1,1-dimethyl-6,8-disulfo-3-(3-sulfo-propyl)-1H-benzo[e]indol-2(3H)-ylidene)penta-1,3-dien-1-yl)-1,1-dimethyl-6-(N-methyl-N-(4-oxo-4-((4-((5-sul-famoyl-1,3,4-thiadiazol-2-yl)carbamoyl)benzyl)amino)butyl)sulfamoyl)-1H-benzo[e]indol-3-ium-3-yl)propane-1-sulfonate;

3-(2-((1E,3Z,5E)-5-(1,1-dimethyl-6,8-disulfo-3-(3-sulfo-propyl)-1H-benzo[e]indol-2(3H)-ylidene)-3-(5-((6-oxo-6-((4-((5-sulfamoyl-1,3,4-thiadiazol-2-yl)carbamoyl)benzyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-ethyl-2-((1E,3Z,5E)-5-(3-ethyl-1,1-dimethyl-6,8-disulfo-1H-benzo[e]indol-2(3H)-ylidene)-3-(5-((4-((5-sulfa-moyl-1,3,4-thiadiazol-2-yl)carbamoyl)benzyl)carbam-oyl)pyridin-2-yl)penta-1,3-dien-1-yl)-1,1-dimethyl-8-sulfo-1H-benzo[e]indol-3-ium-6-sulfonate;

3-(2-((1E,3Z,5E)-5-(1,1-dimethyl-6,8-disulfo-3-(3-sulfo-propyl)-1H-benzo[e]indol-2(3H)-ylidene)-3-(5-((4-((5-sulfamoyl-1,3,4-thiadiazol-2-yl)carbamoyl)benzyl)car-bamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3Z,5E)-5-(1,1-dimethyl-6,8-disulfo-3-(3-sulfo-propyl)-1H-benzo[e]indol-2(3H)-ylidene)-3-(5-((3-oxo-1-(4-((5-sulfamoyl-1,3,4-thiadiazol-2-yl)carbamoyl)phe-nyl)-6,9,12,15,18,21,24,27,30,33,36,39,42,45,48,51,54,57,60,63,66,69,72,75-tetracosaoxa-2-azaheptaheptacontan-77-yl)carbamoyl)pyridin-2-yl)penta-1,3-dien-1-yl)-1,1-dimethyl-6,8-disulfo-1H-benzo[e]indol-3-ium-3-yl)propane-1-sulfonate;

3-(2-((1E,3Z,5E)-5-(1,1-dimethyl-6,8-disulfo-3-(3-sulfo-propyl)-1H-benzo[e]indol-2(3H)-ylidene)-3-(5-((3-oxo-3-((5-sulfamoyl-1,3,4-thiadiazol-2-yl)amino)propyl)car-bamoyl)pyridin-2-yl)penta-1,3-dien-1-yl)-1,1-dimethyl-6,8-disulfo-1H-benzo[e]indol-3-ium-3-yl)propane-1-sulfonate; and 3-(2-((1E,3Z,5E)-5-(3,3-dimethyl-5-sulfo-1-(3-sulfopropyl)indolin-2-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-3,3-dimethyl-5-sulfo-3H-indol-1-ium-1-yl)propane-1-sulfonate; and pharmaceutically acceptable salts thereof.

In certain embodiments, the carbonic anhydrase targeting agent is one of the carbonic anhydrase targeting agents described in the Examples or a pharmaceutically acceptable salt thereof.

The carbonic anhydrase targeting agents can be fluorescent in the far-red or near-infrared spectral range.

In certain embodiments, the carbonic anhydrase targeting agent further comprises one or more chemical modifiers, independently, chemically linked to the CAB, L, and/or F or any combination thereof. Each of the features of the carbonic anhydrase binding moieties, imaging reporters, linkers and biological modifiers are discussed in more detail below.

Carbonic Anhydrase Binding Moieties

Certain exemplary carbonic anhydrase binding moieties useful in the practice of the invention are described in U.S. Pat. No. 7,833,737; and International Application Publication Nos. WO2006/137092, WO2008/124703, WO 2010/147666, and WO2010/065906, all of which are incorporated herein by reference in their entirety.

In certain embodiments, the carbonic anhydrase binding (CAB) moiety is -aryl-$SO_2NH_2$, -heterocyclyl-$SO_2NH_2$, -aryl-C(O)N(R')-heteroaryl-$SO_2NH_2$, -heteroaryl-C(O)N(R')-heteroaryl-$SO_2NH_2$, —C(O)N(R')-heteroaryl-heteroaryl-$SO_2NH_2$, or —C(O)N(R')-aryl-heteroaryl-$SO_2NH_2$, wherein R' represents independently for each occurrence hydrogen or $C_{1-6}$ alkyl; each aryl and heteroaryl are optionally substituted with 1 or 2 substituents independently selected from the group consisting of alkyl and halogen, and each heterocyclyl is optionally substituted with 1, 2, or 3 substituents independently selected from the group consisting of alkyl, halogen, amino, and oxo.

In certain embodiments, the CAB is -phenyl-$SO_2NH_2$; -pyridinyl-$SO_2NH_2$; 1,3,4-thiadiazole-$SO_2NH_2$; -benzo[d]thiazole-$SO_2NH_2$; -phenyl-C(O)N(H)-pyridinyl-$SO_2NH_2$; -phenyl —C(O)N(H)-1,3,4-thiadiazole-$SO_2NH_2$; -pyridinyl-C(O)N(H)-1,3,4-thiadiazole-$SO_2NH_2$; —C(O)N(H)-pyridinyl-1,3,4-thiadiazole-$SO_2NH_2$; or —C(O)N(H)-phenyl-1,3,4-thiadiazole-$SO_2NH_2$; wherein each phenyl, pyridinyl, and thiadiazole are optionally substituted with 1 or 2 substituents independently selected from the group consisting of alkyl and halogen.

In certain embodiments, the carbonic anhydrase binding moiety is one of the following:

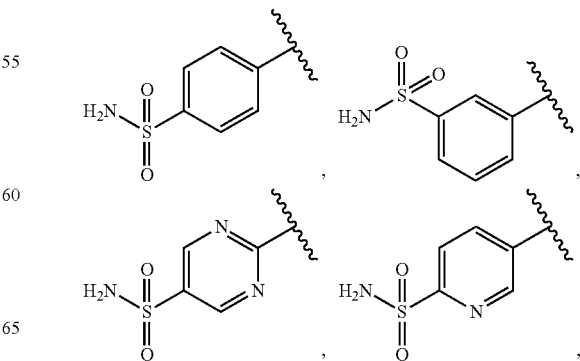

Imaging Reporters

It is understood that a variety of different imaging reporters, for example, fluorescent and non-fluorescent reporters can be used to produce a carbonic anhydrase targeting agent of the invention.

(a) Fluorescent Reporters

In certain embodiments the imaging reporter is a fluorophore molecule. A "fluorophore" includes, but is not limited to, a fluorochrome, a fluorochrome quencher molecule, any organic or inorganic dye, metal chelate, or any fluorescent enzyme substrate, including protease activatable enzyme substrates.

In certain embodiments, the carbonic anhydrase targeting agents comprise a fluorophore. In certain embodiments, the fluorophores are far red and near infrared fluorochromes (NIRFs) with absorption and emission maximum between about 600 and about 1200 nm, more preferably between about 600 nm and about 900 nm. It will be appreciated that the use of fluorochromes with excitation and emission wavelengths in other spectrums can also be employed in the compositions and methods of the present invention. Exemplary fluorochromes include but are not limited to a carbocyanine fluorochrome and an indocyanine fluorochrome.

The near infrared fluorochromes preferably have an extinction coefficient of at least 50,000 $M^{-1}cm^{-1}$ per fluorochrome molecule in aqueous medium. The near infrared fluorochromes preferably also have (1) high quantum yield (i.e., quantum yield greater than 5% in aqueous medium), (2) narrow excitation/emission spectrum, spectrally separated absorption and emission spectra (i.e., excitation and emission maxima separated by at least 15 nm), (3) high chemical and photostability, (4) non-toxicity, (5) good biocompatibility, biodegradability and excretability, and (6) commercial viability and scalable production for large quantities (i.e., gram and kilogram quantities) required for in vivo and human use.

Certain carbocyanine or polymethine fluorescent dyes can be used to produce the carbonic anhydrase targeting agents of the invention and include, for example, those described in U.S. Pat. Nos. 6,747,159; 6,448,008; 6,136,612; 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; also WO 97/40104, WO 99/51702, WO 01/21624, and EP 1 065 250 A1; and Tetrahedron Letters 41, 9185-88 (2000).

Various fluorochromes are commercially available and can be used to construct the carbonic anhydrase targeting agents of the invention. Exemplary fluorochromes include, for example, Cy5.5, Cy5 and Cy7 (GE Healthcare); AlexaFlour660, AlexaFlour680, AlexaFluor750, and AlexaFluor790 (Invitrogen); VivoTag680, VivoTag-S680, and VivoTag-5750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health).

Table 1 lists a number of exemplary fluorochromes useful in the practice of the invention together with their spectral properties.

TABLE 1

| Fluorochrome | $\varepsilon_{max}$ $M^{-1}cm^{-1}$ | Absorbance max (nm) |
|---|---|---|
| Cy5 | 250,000 | 649 |
| Cy5.5 | 250,000 | 675 |
| Cy7 | 250,000 | 743 |
| AlexaFlour660 | 132,000 | 663 |
| AlexaFlour680 | 184,000 | 679 |
| AlexaFlour750 | 280,000 | 749 |
| VivoTag680 (VT680) | 100,000 | 670 |
| VivoTag-S680 | 220,000 | 674 |
| VivoTag-S750 | 100,000 | 750 |
| Dy677 | 180,000 | 673 |
| Dy682 | 140,000 | 690 |
| Dy752 | 270,000 | 748 |
| Dy780 | 170,000 | 782 |
| DyLight547 | 150,000 | 557 |
| DyLight647 | 250,000 | 653 |
| IRDye800CW | 240,000 | 774 |
| IRDye800RS | 200,000 | 767 |
| IRDye700DX | 165,000 | 689 |
| ADS780WS | 170,000 | 782 |
| ADS830WS | 240,000 | 819 |
| ADS832WS | 190,000 | 824 |

In some embodiments, the fluorophore is substituted by a plurality of chemical modifying groups. In one embodiment, the fluorophore is represented by formula VI:

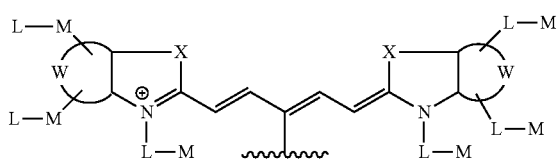

(VI)

or a salt thereof, wherein:
W represents a benzo-condensed, a naphtho-condensed or a pyrido-condensed ring;
X, independently for each occurrence, is selected from the group consisting of $C(CH_2Y_1)(CH_2Y_2)$, O, S, and Se;
$Y_1$ and $Y_2$ are independently selected from the group consisting of H and $C_1$-$C_{20}$ aliphatic group, each of which is optionally substituted with L-M;
L, independently for each occurrence, represents a bond or a linker moiety;
M, independently for each occurrence, represents a chemical modifying moiety.

In one embodiment, the fluorochrome is represented by formula VII:

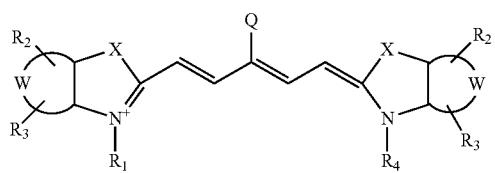

(VII)

or a salt thereof, wherein:
X is independently selected from the group consisting of $C(CH_2Y_1)(CH_2Y_2)$, O, S, and Se;
$Y_1$ and $Y_2$ are independently selected from the group consisting of H, $C_1$-$C_{20}$ aliphatic group and a $C_1$-$C_{20}$ aliphatic group substituted with —OR*, N(R*)$_2$ or —SR*;
W represents a benzo-condensed, a naphtho-condensed or a pyrido-condensed ring;
R* is alkyl;
$R_1$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;
$R_4$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;
$R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety; and
Q is selected from a group consisting of a heteroaryl ring substituted with a carboxyl group or 6-membered heteroaryl ring substituted with a carbonyl group.

In certain embodiments of formula VII, Q is selected from a group consisting of (i) a carboxyl functionalized heterocyclic ring, (ii) a carboxyl functionalized nitrogen containing heterocyclic ring, (iii) a carboxyl functionalized nitrogen containing 6-membered heterocyclic ring, such as pyridine, pyrimidone, pyrazine, and pyridazine, (iv) a carboxyl functionalized nitrogen containing 6-membered heterocyclic ring, such as pyridine, (v) a carbonyl functionalized nitrogen containing 6-membered heterocyclic ring, such as pyridine, and (vi) an isonicotinic acid, nicotinic acid and picolinic acid, and a group selected from:

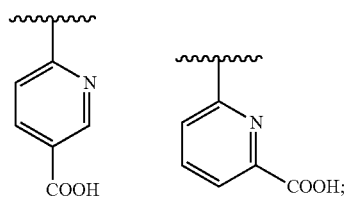

wherein, the carboxyl group is also in the form of an ester, an activated ester or carbonyl halide capable of reacting with nucleophiles, and can be, for example, a —C(O)O-benzotriazolyl, —C(O)O—N-succinimidyl, —C(O)O-tetrafluorophenyl, —C(O)O-pentafluorophenyl, —C(O)O-imidazole, or —C(O)O-p-nitrophenyl.

In another embodiment, the fluorochrome is represented by formula VIII:

(VIII)

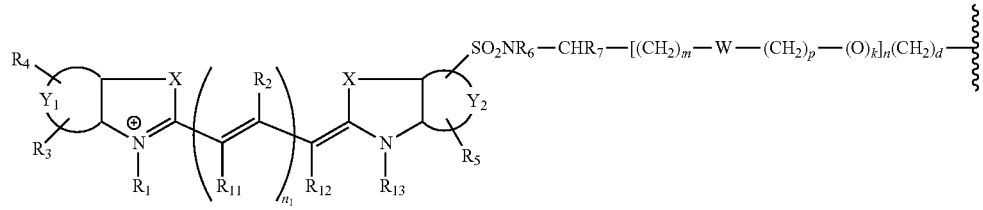

or a salt thereof, wherein:
- $X_1$ and $X_2$ are independently selected from the group consisting of $C(CH_2K_1)(CH_2K_2)$, O, S and Se;
- $K_1$ and $K_2$ are independently H or a $C_1$-$C_{20}$ aliphatic group; or $K_1$ and $K_2$ together are part of a substituted or unsubstituted carbocyclic or heterocyclic ring;
- $Y_1$ and $Y_2$ are each independently a benzo-condensed ring, a naphtha-condensed ring or a pyrido-condensed ring;
- $n_1$ is 1, 2, or 3;
- $R_2$, $R_{11}$ and $R_{12}$ are independently H, halogen, $C_1$-$C_6$ alkyl, $C_1$-$C_6$ alkoxy, aryloxy, aryl, a sulfonate, an iminium ion, or any two adjacent $R_{12}$ and $R_{11}$ substituents, when taken in combination, form a 4-, 5-, or 6-membered carbocyclic ring optionally substituted one or more times by $C_1$-$C_6$ alkyl or halogen;
- $R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;
- $R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;
- $R_6$ is selected from the group consisting of an unsubstituted $C_1$-$C_{20}$ aliphatic group, an unsubstituted aryl, or an unsubstituted alkylaryl;
- $R_7$ is selected from the group consisting of H, an unsubstituted $C_1$-$C_{20}$ aliphatic group, an unsubstituted aryl, or an unsubstituted alkylaryl, wherein $R_7$ is optionally substituted with halogen; or
- $R_6$ and $R_7$, taken together form a 4-, 5-, 6- or 7-membered heterocyclic ring optionally substituted with halogen;
- W is absent or is a group selected from the group consisting of —$SO_2NR_6$—$CHR_7$—, —O—, —COO—, and —CONH—;
- h=0-70; k=0 or 1; d=0-12; m=0-12; p=0-12.

Exemplary chemically modified fluorophores that can be used in the synthesis of the carbonic anhydrase targeting agents of the invention include, for example, those listed in Table 2.

TABLE 2

| No. | Fluorophore |
| --- | --- |
| F1 | 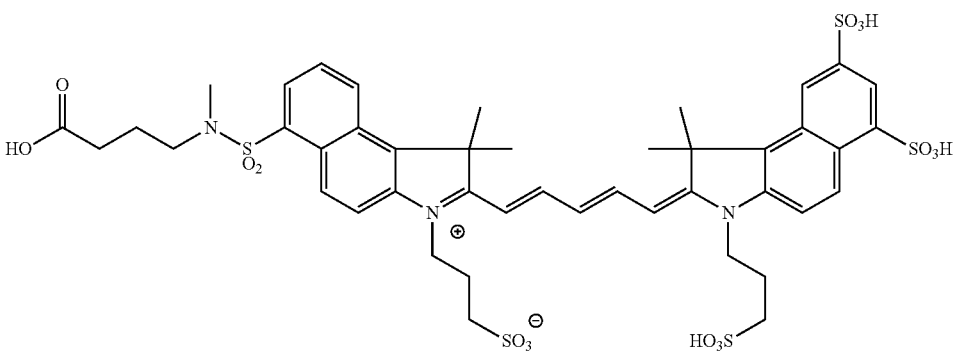 |
| F2 | 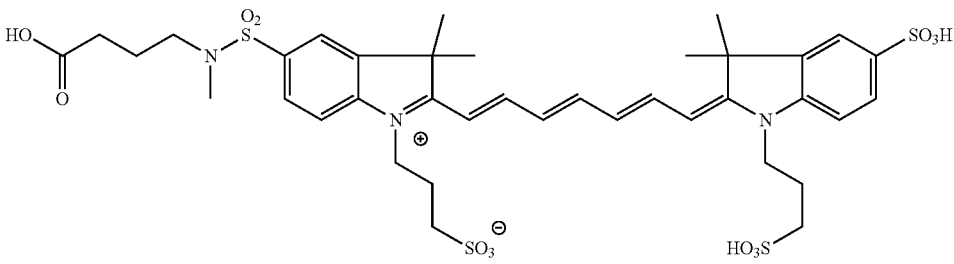 |
| F3 | 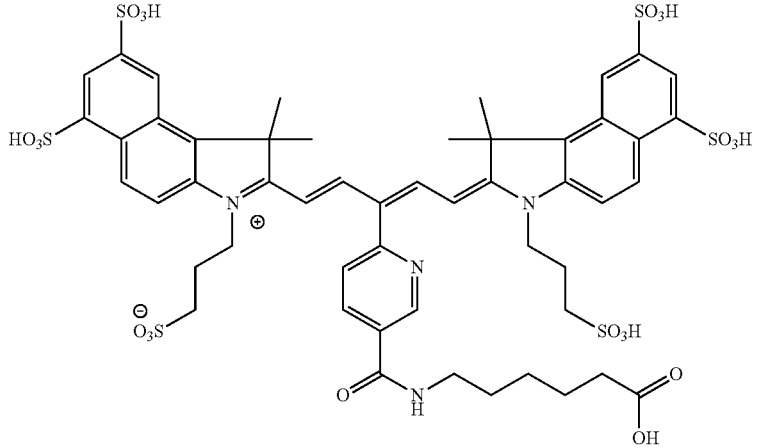 |

TABLE 2-continued

| No. | Fluorophore |
|---|---|
| F4 | (structure) |
| F5 | (structure) |
| F6 | (structure) |

TABLE 2-continued
| No. | Fluorophore |
|---|---|
| F7 | 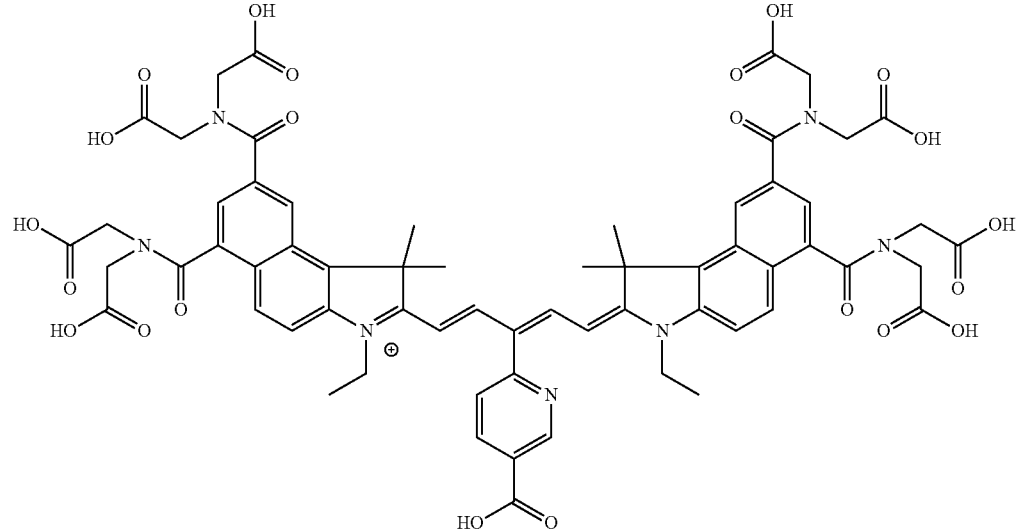 |
| F8 | 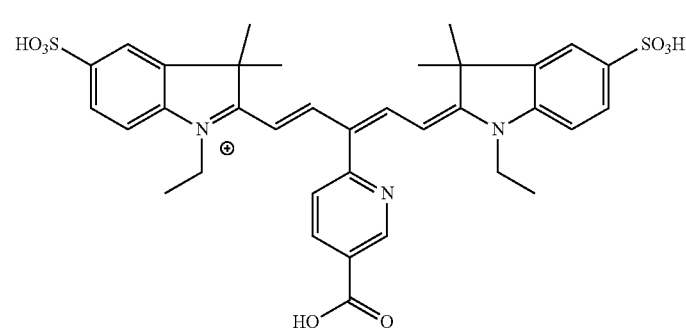 |
| F9 | 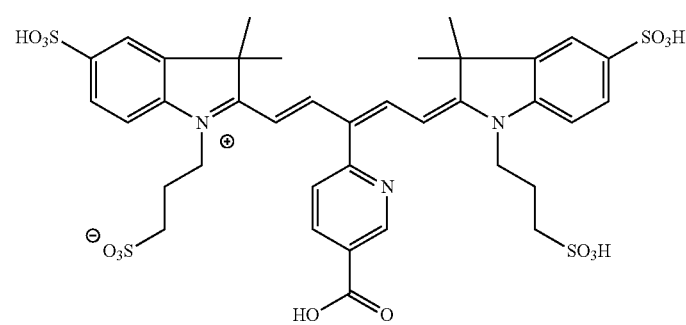 |

TABLE 2-continued

| No. | Fluorophore |
|---|---|
| F10 | |
| F11 | |
| F12 | | n = 3, 4, 8, 12, 24

TABLE 2-continued
| No. | Fluorophore |
|---|---|
| F13 | 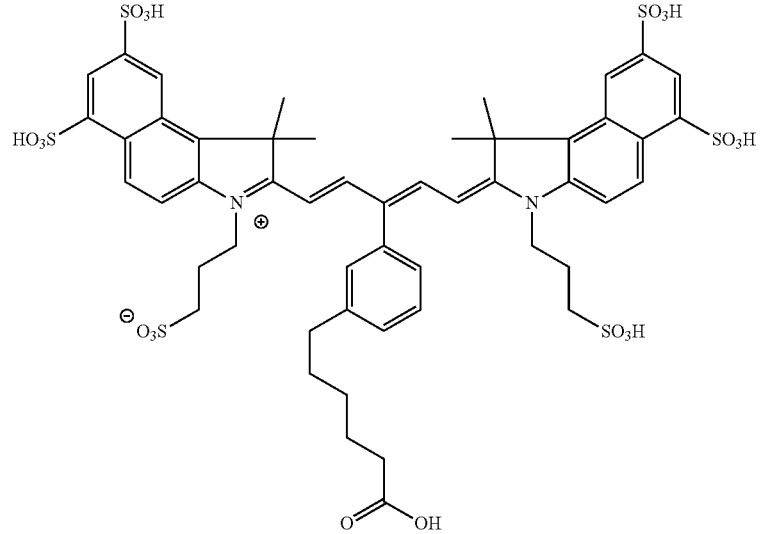 |
| F14 | 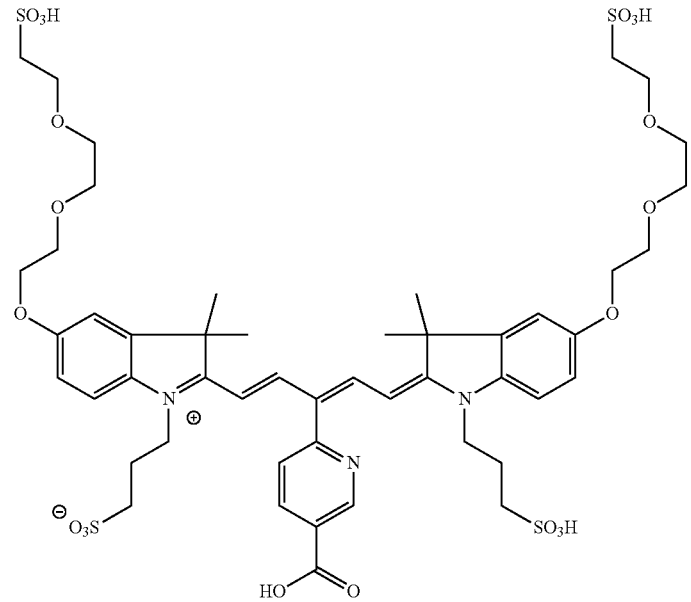 |
| F15 | 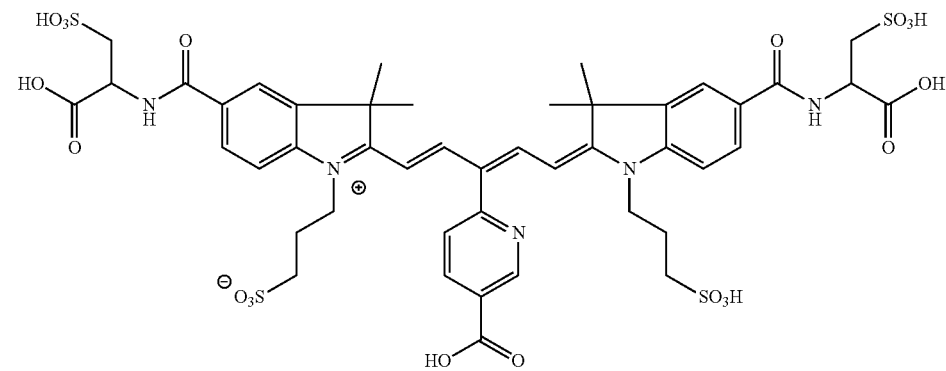 |

TABLE 2-continued

| No. | Fluorophore |
|---|---|
| F16 | 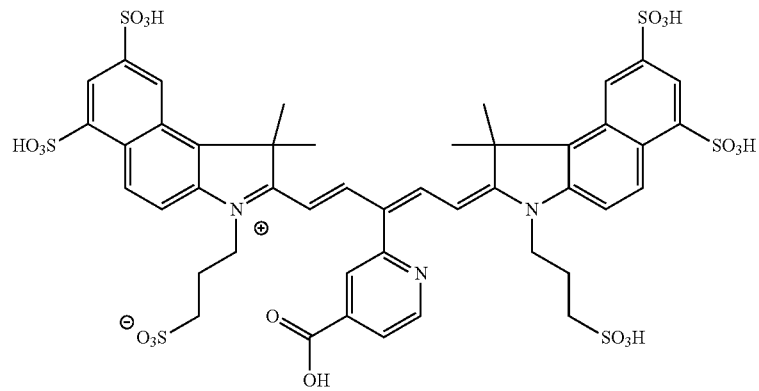 |
| F17 | 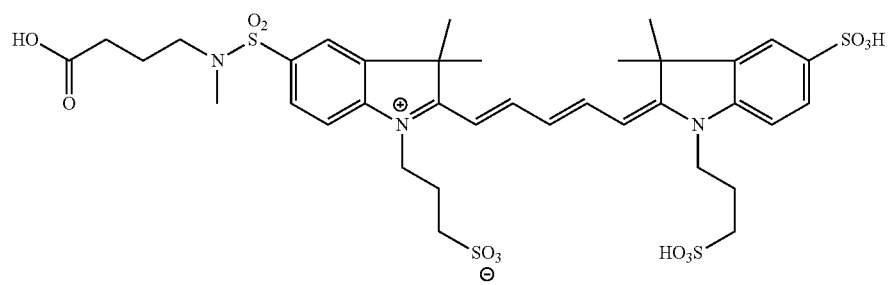 |

In certain embodiments, one or more fluorochrome molecules can be chemically linked to the carbonic anhydrase binding moiety to produce the fluorescent carbonic anhydrase targeting agents.

In the case where the imaging reporter is a fluorochrome molecule, the extinction coefficient of the carbonic anhydrase targeting agents can be calculated as the ratio of the absorbance of dye at its absorption maxima (for example at ~670 nm for VivoTag 680) in a 1 cm path length cell to the concentration of particles using the formula $\varepsilon=A/cl$, where A is absorbance, c is molar concentration and l is path length in cm.

It is understood that carbonic anhydrase targeting agent can be linked to nanoparticles (for example, silicon containing nanoparticles) to produce fluorescent or luminescent nanoparticles. Aggregates of crystalline silicon (as multiple or single crystals of silicon), porous silicon, or amorphous silicon, or a combination of these forms, can form the nanoparticle. Preferred fluorescent silicon nanoparticles have a diameter between about 0.5 nm to about 25 nm, more preferably between about 2 nm and about 10 nm. The size of nanoparticles can be determined by laser light scattering or by atomic force microscopy or other suitable techniques.

Fluorescent silicon nanoparticles may have excitation and emission spectra 200 to 2000 nm, however, preferred fluorescent silicon nanoparticles have excitation and emission maximum between about 400 nm and about 1200 nm (and preferably 500 nm-900 nm, for example, 500 nm-600 nm, 600 nm-700 nm, 700 nm-800 nm, or 800 nm-900 nm). Preferred fluorescent silicon nanoparticles also have extinction coefficients of at least 50,000 $M^{-1}cm^{-1}$ in aqueous medium. Although fluorescent silicon nanoparticles that have excitation and emission maximum between 400 nm and 1200 nm are preferred, it will be appreciated that the use of fluorescent silicon nanoparticles with excitation and emission wavelengths in other spectrums can also be employed in the compositions and methods of the present invention.

For example, in certain embodiments, the particles may have excitation approximately about 300-350 nm, and emission approximately about 400-450 nm.

Fluorescent silicon nanoparticles may also have the following properties: (1) high quantum yield (i.e., quantum yield greater than 5% in aqueous medium), (2) narrow emission spectrum (i.e., less than 75 nm; more preferably less than 50 nm), (3) spectrally separated absorption and emission spectra (i.e., separated by more than 20 nm; more preferably by more than 50 nm), (3) have high chemical stability and photostability (i.e., retain luminescent properties after exposure to light), (4) are biocompatible (see below) or can be made more biocompatible; (5) are non toxic or minimally toxic to cells or subjects at doses used for imaging protocols, (as measured for example, by $LD_{50}$ or irritation studies, or other similar methods known in the art) and/or (6) have commercial viability and scalable production for large quantities (i.e., gram and kilogram quantities) required for in vivo and human use.

Other exemplary fluorophores include metal oxide nanoparticles that are fluorescent and can be used in a variety of in vitro and vivo applications. In one embodiment, the carbonic anhydrase binding moieties are conjugated to fluorescent metal oxide nanoparticles with one or more of the following features: (1) a polymer coating suitable for attaching a plurality of fluorochromes thereby achieving large extinction coefficients (in excess of 1,000,000 $M^{-1}cm^{-1}$), (2) a non-crosslinked polymer coating suitable for attaching from about 10 to about 300 fluorochromes per particle, (3) a polymer coating suitable for attaching a plurality of fluorochromes in a manner that does not significantly compromise the quantum yield of the fluorochromes (e.g., the nanoparticles retain at least 50% of the fluorescent signal that is created by substantially the same number of free fluorochromes when tested under the same conditions), and (4) a polymer coating that is amenable to efficient chemical linking of biomolecules with retention of their biological properties to yield molecular imaging agents. The fluorescent metal oxide nanoparticles are highly stable molecular imaging agents in vitro, both before and after chemical linking of fluorochromes and carbonic anhydrase targeting agents, but yet are labile and/or degradable in vivo.

The carbonic anhydrase binding moiety can be linked to fluorescent quantum dots such as amine T2 MP EviTags (Evident Technologies) or Qdot Nanocrystals (Invitrogen). In general, fluorescent quantum dots are nanocrystals containing several atoms of a semiconductor material (including but not limited to those containing cadmium and selenium, sulfide, or tellurium; zinc sulfide, indium-antimony, lead selenide, gallium arsenide, and silica or ormosil, which have been coated with zinc sulfide to improve the properties of these fluorescent agents.

Furthermore, the carbonic anhydrase binding moiety can be conjugated to molecules capable of eliciting photodynamic therapy. These include, but are not limited to, Photofrin, Lutrin, Antrin, aminolevulinic acid, hypericin, benzoporphyrin derivative, and select porphyrins.

In certain embodiments, one or more different fluorophore molecules can be covalently linked to a cleavable (for example, an enzymatically cleavable) oligopeptide, or alternatively, two substantially similar fluorophores can be covalently linked to the oligopeptide, at fluorescence-quenching permissive locations separated by a cleavage site, for example, a proteolytic cleavage site, to produce the imaging agents of the invention.

In certain embodiments, a quencher is used to quench the fluorescent signal from the fluorophore covalently linked to the oligopeptide. For example, an agent can be designed such that the quencher quenches the fluorescence of the fluorophore of the imaging agent when the agent is in an unactivated state, so that the imaging agent exhibits little or no signal until it is activated. It is understood that the quencher can be a non-fluorescent agent, which when suitably located relative to a fluorophore (i.e., at a fluorescence-quenching permissive location) is capable of quenching the emission signal from the fluorophore. It is understood that certain of the foregoing fluorophores can act to quench the fluorescent signal of another spaced apart fluorophore, when the two fluorophores are positioned at fluorescence-quenching interaction permissive locations.

A number of quenchers are available and known to those skilled in the art including, but not limited to 4-{[4-(dimethylamino)-phenyl]azo}-benzoic acid (DABCYL), QSY®-7 (9-[2-[(4-carboxy-1-piperidinyl)sulfonyl]phenyl]-3,6-bis(methylphenylamino)-xanthylium chloride) (Molecular Probes, Inc., OR), QSY®-33 (Molecular Probes, Inc., OR), ATTO612Q, ATTO580Q (ATTO-TEC, Germany); Black Hole Quenchers® (Bioresearch Technologies, Novato, Calif.), QXL™680 Acid (AnaSpec, San Jose Calif.), and fluorescence fluorophores such as Cy5 and Cy5.5 (e.g., 2-[5-[3-[6-[(2,5-dioxo-1-pyrrolidinyl)oxy]-6-oxohexyl]-1,3-dihydro-1,1-dimethyl-6,8-disulfo-2H-benz[e]indol-2-ylidene]-1,3-pentadienyl]-3-ethyl-1,1-dimethyl-6,8-disulfo-1H-benz[e]indolium, inner salt) (Schobel, Bioconjugate 10:1107, 1999). Other quenching strategies can be used, for example, using various solvents to quench fluorescence of the agents.

Exemplary fluorophores that can quench the emission of other fluorophores are represented in Table 3.

TABLE 3

| No. | Quencher |
|---|---|
| Q1 | 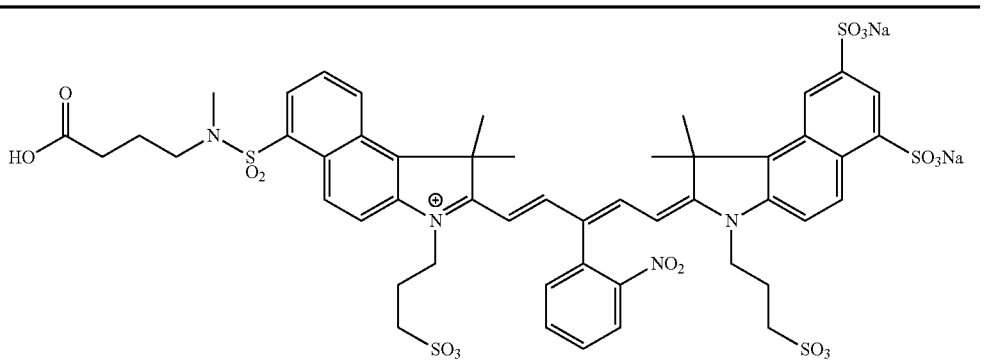 |
| Q2 | 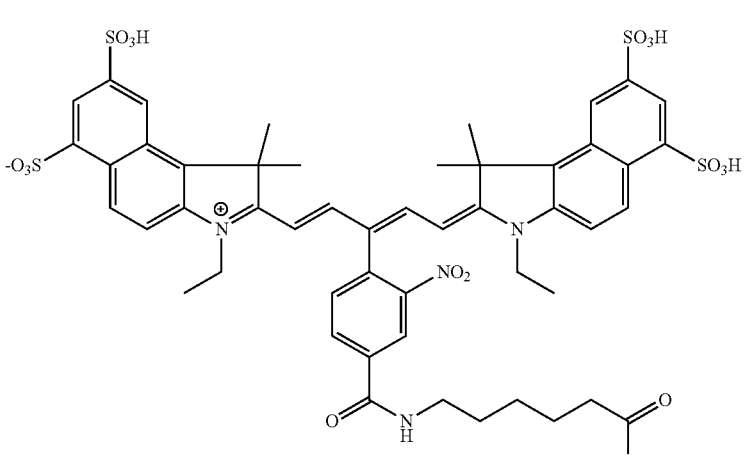 |

In such embodiments, the two fluorophores or the fluorophore and the quencher are located within the intact imaging agent at fluorescent-quenching interaction permissive positions. In other words, a first fluorophore is located close enough in the intact imaging agent to a second fluophore (or quencher) to permit them to interact photochemically with one another so that the second fluorophore (or quencher) quenches the signal from the first fluorophore. In the case of the imaging agents with two fluorophores, one fluorophore preferably quenches the other fluorophore. For principles of quenching, see U.S. Pat. No. 6,592,847.

(b) Non-Fluorescent Reporters

The term "non-fluorescent reporter" as used herein, refers to a chemical moiety that is not fluorescent but which can be used to provide the contrast or signal in imaging and is detectable by a non-fluorescent imaging technique. In certain embodiments, other non-fluorescent reporters can be chemically linked with the imaging agents, or can be administered to a subject simultaneously or sequentially with the imaging agents of the invention. Such reporters can include photoluminescent nanoparticles, radioisotopes, superparamagnetic agents, X-ray contrast agents, and ultrasound agents. A reporter may also comprise therapeutic reporters such as porphyrins, Photofrin®, Lutrin®, Antrin®, aminolevulinic acid, hypericin, benzoporphryrin derivatives used in photodynamic therapy, and radionuclides used for radiotherapy.

(i) Radioactive Reporters

The agents can include one or more radioactive labels. Radioisotopic forms of metals such as copper, gallium, indium, technetium, yttrium, and lutetium can be chemically linked to the metallic imaging agents and can be used for nuclear imaging or therapeutic applications. Exemplary radioactive labels include, without limitation, $^{99m}$Tc, $^{111}$In, $^{64}$Cu, $^{67}$Ga, $^{186}$Re, $^{188}$Re, $^{153}$Sm, $^{177}$Lu, and $^{67}$Cu.

Other exemplary labels include, for example, $^{123}$I, $^{124}$I, $^{125}$I, $^{11}$C, $^{13}$N, $^{15}$O, and $^{18}$F.

Other exemplary labels can be therapeutic radiopharmaceuticals including for example, $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir.

Chelators or bonding moieties for diagnostic and therapeutic radiopharmaceuticals are also contemplated and can be chemically associated with the imaging agents. Exemplary chelators can be selected to form stable complexes with radioisotopes that have imageable gamma ray or positron emissions, such as $^{99m}$Tc, $^{111}$In, $^{64}$Cu, and $^{67}$Ga. Exemplary chelators include diaminedithiols, monoamine-monoamidedithiols, triamide-monothiols, monoamine-diamide-monothiols, diaminedioximes, and hydrazines. Chelators generally are tetradentate with donor atoms selected from nitrogen, oxygen and sulfur, and may include for example, cyclic and acyclic polyaminocarboxylates such as diethylenetriaminepentaacetic acid (DTPA), 1,4,7,10-tetraazacyclododecane-1,4,7,10-tetraacetic acid (DOTA), (DO3A), 2-benzyl-DOTA, alpha-(2-phenethyl)1,4,7,10-tetraazazcyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N'',N''-tetra(carboxymethyl)aminomethyl)-4'-(3-amino-4-methoxyphenyl)-2,2':6',2"-terpyridine.

(ii) Magnetic Reporters

Other exemplary reporters can include a chelating agent for magnetic resonance agents. Such chelators can include for example, polyamine-polycarboxylate chelators or iminoacetic acid chelators that can be chemically linked to the agents.

Chelators for magnetic resonance imaging agents can be selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(met hylacetic)acid, 2-benzyl-cyclohexyldiethylenetriaminepentaacetic acid, 2-benzyl-6-methyl-DTPA, and 6,6"-bis[N,N,N'',N''-tetra(carboxymethyl)aminomethyl)-4'-(3-amino-4-methoxyphenyl)-2,2':6',2"-terpyridine.

In one embodiment, the carbonic anhydrase targeting agents are conjugated to superparamagnetic metal oxide nanoparticles that are either (a) non-fluorescent or (b) are fluorescent and can be used in a variety of in vitro and vivo applications. Fluorescent metal oxide nanoparticles that also have magnetic properties can be used for MRI, thus providing a multi-modality imaging agent.

In certain embodiments, the imaging agents can include a fluorescent and/or non-fluorescent superparamagenetic metal oxide nanoparticle with one or more of the following features: (1) a polymer coating suitable for attaching a plurality of agents (2) a non-crosslinked polymer coating suitable for attaching from about 10 to about 300 agents per particle, and (3) a polymer coating that is amenable to efficient chemical linking of the agents with retention of their biological properties to yield molecular imaging agents. The agent modified metal oxide nanoparticle can be a highly stable molecular imaging agent in vitro, both before and after chemical linking of the agents, but yet are labile and/or degradable in vivo.

The carbonic anhydrase targeting agent conjugated metal oxide nanoparticles can be formulated into a pharmaceutical composition suitable for administration to a subject, for example, an animal and/or a human subject.

(iii) Ultrasound Reporters

For ultrasound imaging, the imaging reporter can include gas-filled bubbles such as Levovist, Albunex, or Echovist, or particles or metal chelates where the metal ions have atomic numbers 21-29, 42, 44 or 57-83. Examples of such compounds are described in Tyler et al., *Ultrasonic Imaging*, 3, pp. 323-29 (1981) and D. P. Swanson, "Enhancement Agents for Ultrasound: Fundamentals," Pharmaceuticals in Medical Imaging, pp. 682-87 (1990).

(iv) X-Ray Reporters

Exemplary reporters can comprise iodinated organic molecules or chelates of heavy metal ions of atomic numbers 57 to 83. Examples of such compounds are described in M. Sovak, ed., "Radiocontrast Agents," *Springer-Verlag*, pp. 23-125 (1984) and U.S. Pat. No. 4,647,447.

Linkers

Linker or spacer moieties (L) can be used to chemically link one or more chemical modifiers (M) to the fluorophore and/or to link the CAB moiety to Q or, if Q is absent, directly to the fluorophores of the agents of the present invention. Useful linker moieties include both natural and non-natural amino acids and nucleic acids, peptides, such as glycine, β-alanine, γ-aminobutyric acid or aminocaproic acid, as well as synthetic linker molecules such as aminoethyl maleimide or aminomethyl benzoic acid, or a polymer such as homobifunctional or heterobifunctional polyethylene glycol (PEG). When the linker is a peptide, the peptide optionally may include proteolytic cleavage site that can be cleaved with a variety of agents, for example, an enzyme.

It is understood that there is no particular structural, size or content limitation for a given linker. Linkers can include, for example, a variety of functional groups such as maleimide, dithiopyridyl, thiol, azide, alkene, or alkyne that permit the assembly of molecules of diverse architecture.

Linkers can be homofunctional linkers or heterofunctional linkers. For example, amine ($NH_2$)-functionalized moieties can be reacted with bifunctional cross-linkers designed to react with amino groups. Particularly useful conjugation reagents that can facilitate formation of a linker or facilitate covalent linkage between, for example, a fluorophore, and an enzymatically cleavable oligopeptide can include a N-hydroxysuccinimide (NHS) ester and/or a maleimide. The NHS ester can react with the amine group of, for example, a peptide or fluorophore. The maleimide can react with the sulfhydryl group of another molecule. Other particularly useful linker moieties are bifunctional crosslinkers such as N-succinimidyl 3-(2-pyridyldithio)propionate (SPDP), long chain-SPDP, maleimidobenzoic acid-N-hydroxysuccinimide ester (MBS), succinimidyl trans-4-(maleimidylmethyl)cyclohexane-1-carboxylate (SMCC), succinimidyl iodoacetate (SIA).

In certain embodiments a linker, if present, may be a derivative of a diamine. A diamine moiety or derivative can provide a linker arm of varying lengths and chemistries for chemically linking molecules by derivatizing, optionally, with carboxylic acids. Non-limiting examples of diamines include ethylenediamine (EDA), propylenediamine, spermidine, spermine, hexanediamine, and diamine-amino acids, such as homolysine, lysine, ornithine, diaminobutyric acid and diaminopropionic acid. In other embodiments, moieties of an imaging agent can be chemically linked to a dicarboxylic acid, for example, succinic acid, glutaric acid, suberic acid, or adipic acid. In one embodiment, the linker is aminoethylmaleimide.

In certain embodiments, a linker can be branched, for example glutamic acid or 5-(aminomethyl)isophthalic acid, or a dendrimer, such as a lysine or glutamic acid dendrimer, with multiple M groups linked to a single site on the fluorophore.

In certain embodiments, L is a functionalized, substituted or unsubstituted $C_1$-$C_{18}$ alkyl, alkenyl, alkynyl, alkoxy, or thioalkyl group. In other embodiments, L is functionalized, substituted or unsubstituted aromatic or heteroaromatic ring. In other embodiments, L is absent.

In certain embodiments, a linker can be formed from an azide moiety that can react with substituted alkynes in an azide-acetylene Huisgen [3+2] cycloaddition. In certain embodiments the azide or alkyne linker can link a polyethyleneglycol (PEG) moiety to, for example, an enzymatically cleavable oligopeptide. Other contemplated linkers include propargylglycine, pentanoyl, pentynoic acid, propargylic acid, and/or propargylamine moieties.

In certain embodiments, the imaging reporters are directly chemically linked to the carbonic anhydrase binding moiety using reactive NHS esters groups on the IR which react with the amine group of the amino-functionalized CAB. In certain other embodiments, carboxylic acid groups on the IR can be activated in situ by activating agents known in the art, such as 2-(1H-benzotriazole-1-yl)-1,1,3,3,-tetramethyluronium hexafluorophosphate (HBTU), 1-ethyl-3-(3'-dimethylaminopropyl)-carbodiimide hydrochloride (EDC), N,N'-dicyclohexylcarbodiimide (DCC), N,N'-disuccinimidyl carbonate (DSC). In other embodiments, IRs containing a sulfhydryl or thiol group, can be chemically linked to the ITM via a bifunctional cross-linker that has a second moiety that can react with a sulfhydryl (thiol) group. Such cross-linking agents include, for example and as described above, SPDP, long chain-SPDP, SIA, MBS, SMCC, and others that are well known in the art.

Useful linker moieties include both natural and non-natural amino acids, oligopeptides, for example, linear or cyclic oligopeptides, and nucleic acids. The linker can be a peptide or peptide moiety. The linker can optionally include a proteolytic or non-proteolytic cleavage site, such as an ester linkage, that can be cleaved due to pH changes at the site of interest.

As used herein, the term "enzymatically cleavable oligopeptide" is understood to mean a peptide comprising two or more amino acids (as defined herein) that are linked by means of a enzymatically cleavable peptide bond. Also included are moieties that include a pseudopeptide or peptidomimetic. Examples of cleavable peptide substrates can be found in U.S. Pat. No. 7,439,319.

The term "amino acid" as used herein is understood to mean an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Natural amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Other amino acids include, but not limited to, arginosuccinic acid, citrulline, cysteine sulfinic acid, 3,4-dihydroxyphenylalanine, homocysteine, homoserine, ornithine, carnitine, selenocysteine, selenomethionine, 3-monoiodotyrosine, 3,5-diiodotryosine, 3,5,5'-triiodothyronine, and 3,3',5,5'-tetraiodothyronine.

Modified or unusual amino acids which can be used to practice the invention include, but are not limited to, D-amino acids, hydroxylysine, dehydroalanine, pyrrolysine, 2-aminoisobutyric acid, gamma aminobutyric acid, 5-hydroxytryptophan, S-adenosyl methionine, S-adenosyl homocysteine, 4-hydroxyproline, an N-Cbz-protected amino acid, 2,4-diaminobutyric acid, homoarginine, norleucine, N-methylaminobutyric acid, naphthylalanine, phenylglycine, .beta.-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, a "pseudopeptide" or "peptidomimetic" is a compound which mimics the structure of an amino acid residue or a peptide, for example, by using linking groups other than via amide linkages (pseudopeptide bonds) and/or by using non-amino acid substituents and/or a modified amino acid residue. A "pseudopeptide residue" means that portion of a pseudopeptide or peptidomimetic that is present in a peptide. The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation. The following conventional three-letter amino acid abbreviations are used herein: Ala=alanine; Aca=aminocaproic acid, Ahx=6-aminohexanoic acid, Arg=arginine;

Asn=asparagines; Asp=aspartic acid; Cha=cyclohexylalanine; Cit=citrulline; Cys=cysteine; Dap=diaminopropionic acid; Gln=glutamine; Glu=glutamic acid; Gly=glycine; His=histidine; Ile=isoleucine; Leu=leucine; Lys=lysine; Met=methionine; Nal=naphthylalanine; Nle=norleucine; Orn=ornithine; Phe=phenylalanine; Phg=phenylglycine; Pro=praline; Sar=sarcosine; Ser=serine; Thi=Thienylalanine; Thr=threonine; Trp=tryptophan; Tyr=tyrosine; and Val=valine. Use of the prefix D-indicates the D-isomer of that amino acid; for example D-lysine is represented as D-Lys.

The peptides can be synthesized using either solution phase chemistry or solid phase chemistry or a combination of both (Albericio, Curr. Opinion. Cell Biol., 8, 211-221 (2004), M. Bodansky, Peptide Chemistry: A Practical Textbook, Springer-Verlag; N. L. Benoiton, Chemistry of Peptide Synthesis, 2005, CRC Press).

Selective or orthogonal amine protecting groups may be required to prepare the agents of the invention. As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Synthesis, Biology, Vol. 3, Academic Press, New York (1981). Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. Also included in the term "amine protecting group" are acyl groups such as azidobenzoyl, p-benzoylbenzoyl, o-benzylbenzoyl, p-acetylbenzoyl, dansyl, glycyl-p-benzoylbenzoyl, phenylbenzoyl, m-benzoylbenzoyl, benzoylbenzoyl.

In certain embodiments the enzymatically cleavable oligopeptide can include oligo-L-arginine, oligo-L-lysine, oligo-L-aspartic acid or oligo-L-glutamic acid.

The enzymatically cleavable oligopeptide is cleavable by at least one enzyme chosen from hydrolases, elastases, cathepsins, matrix metalloproteases, peptidases, exopeptidases, endopeptidases, carboxypeptidases, glycosidases, lipases, nucleases, lyases, amylases, phospholipases, phosphatases, phosphodiesterases, sulfatases, serine proteases, subtilisin, chymotrypsin, trypsin, threonine proteases, cysteine proteases, calpains, papains, caspases, aspartic acid proteases, pepsins, chymosins, glutamic acid proteases, renin, reductases, and parasitic, viral and bacterial enzymes.

Chemical Modifiers

Depending upon the intended use, the carbonic anhydrase targeting agents can comprise one or more chemical modifiers (M), which can alter the physical, chemical or biological properties of the carbonic anhydrase targeting agent. In particular, a plurality of Ms can be chemically linked to the phluorophore moiety of the agent. The Ms can be the same or can be different for each occurrence. For example, the Ms may render the carbonic anhydrase agents more useful for biological imaging, that is, for example, more water soluble, or more dispersible in media for administration, with increased binding specificity, or less immunogenic, or less toxic, or with reduced non-specific binding, altered biodistribution and pharmacokinetic compared to an unsubstituted or lesser substituted fluorophore moiety.

For example, incorporation of methoxypolyethylene glycol (mPEG) or polypeptides or a plurality of anionic Ms may function to modify the pharmacodynamics and blood clearance rates of the carbonic anhydrase agents in vivo. Other Ms can be chosen to accelerate the clearance of the carbonic anhydrase targeting agents from background tissue, such as muscle or liver, and/or from the blood, thereby reducing the background interference and improving image quality. Additionally, the Ms can be used to favor a particular route of excretion, e.g., via the kidneys rather than via the liver. The Ms can also aid in formulating probes in pharmaceutical compositions or may be used to alter or preserve the signal reporting properties of the carbonic anhydrase targeting agents. In particular, chemical linking of polyethylene glycol (PEG) or a derivative thereof to carbonic anhydrase targeting agents can result in longer blood residence time (longer circulation) and decreasing immunogenicity.

Exemplary modifiers include polyethylene glycol (PEG) and derivatives thereof (for example, alkoxy polyethylene glycol (for example, methoxypolyethylene glycol, ethoxypolyethylene glycol and the like), branched polypropylene glycol, polypropylene glycol, a graft copolymer of polylysine and methoxypolyethyleneglycol, amino acids, peptides, lipids, fatty acids, palmitate, phospholipids, phospholipid-PEG conjugates, carbohydrates (such as dextran, amino-dextran, carboxymethyl-dextran), iron oxide nanoparticles, sulfonates, polysulfonates, cysteic acid, naphthylalanine, phenylalanine, and 3,3-diphenylpropylamine taurine, phosphonates, phosphates, carboxylates and polycarboxylates.

In certain embodiments, the chemical modifier M is an anionic moiety selected from the group consisting of carboxylate, phosphonate, phosphate, iminodiacetate, cysteic acid, or taurine.

In certain embodiments, the chemical modifier M is a sulfonate or polysulfonate.

In certain embodiments, the chemical modifier M is a hydrogen, alcohol, sulfonamide, sulfoxide, sulfone, ketone, an amino acid such as glutamic acid or taurine, a polyamino acid such as polycysteic acid, oligo- or polyethylene glycol, an amine, a quaternary ammonium ion, or a carbohydrate such as glucosamine, galactosamine or mannosamine.

In certain embodiments, the chemical modifier M is a metal chelator, such as ethylenediamine tetraacetic acid (EDTA), diethylenetriamine pentaacetic acid (DTPA), or tetraazacyclododecane tetraacetic acid (DOTA). In another aspect of the invention, one or more metal chelating M groups are coordinated to a metal ion.

In certain embodiments, as discussed above, the biological modifier may be a PEG moiety that has a molecular weight, for example, from about 0.1 kDa to about 50 kDa, about 5 kDa to about 35 kDa, or about 10 kDa to about 30 kDa. Alternatively, the PEG may be dPEG, functionalized at a discrete molecular weight, for example, of about 1100 daltons.

In certain embodiments, the PEG is methoxyPEG$_{(5000)}$-succinimidylpropionate (mPEG-SPA), methoxyPEG$_{(5000)}$-succinimidylsuccinate (mPEG-SS). Such PEGS are commercially available from Nektar Therapeutics or SunBiowest or LaysanBio or NOF.

The PEG moiety can be conjugated to reactive amines on the carbonic anhydrase targeting agent via a carboxyl functionality. Alternatively, the PEG modifier can be conjugated to the carbonic anhydrase targeting agent by using a thiol reactive cross linker and then reacting with a thiol group on the PEG.

In one embodiment, the PEG may be branched, or Y-shaped, as available from JenKem USA or NOF, or comb-shaped, or synthesized by coupling two or more PEGs to a small molecule such as glutamic acid.

The omega position of PEG may include a hydroxyl group or a methoxy group and the PEG may also contain an amino group in the omega position. Such an amino group can in turn be coupled to a variety of agents. In another embodiment of the present invention, the biological modifier can be a pegylated poly-L-lysine or a pegylated poly-D-lysine.

In other embodiments, the biological modifier can be polyvinylpyrrolidone (PVP)-type polymers. The biological modifier can be a functionalized polyvinylpyrrolidone, for example, carboxy or amine functionalized on one (or both) ends of the polymer (as available from Polymersource) or within the polymer chain.

Alternatively, the biological modifier can include Poly N-(2-hydroxypropyl)methacrylamide (HPMA), or functionalized HPMA (amine, carboxy, etc.), Poly(N-isopropyl acrylamide) or functionalized poly(N-isopropylacrylamide).

Biological modifiers can include straight or branched chain acyl groups, such as pentynoyl; acidic groups, such as succinyl; lower alkyl groups, such as methyl, ethyl, propyl, etc.; carboxyalkyl groups, such as carboxyethyl; haloalkyl groups, such as trifluoromethyl; and the like.

In general, the chemical linking of Ms does not adversely affect the affinity and/or binding properties of the carbonic anhydrase targeting agents.

Exemplary Carbonic Anhydrase Targeting Agents, and Formulations

Useful carbonic anhydrase targeting agents can be created using one or more of the carbonic anhydrase binding moieties, imaging reporters, biological modifiers, and linkers described hereinabove using standard chemistries known in the art. Depending upon the particular application, the carbonic anhydrase targeting agents should be water soluble or water dispersible (i.e., sufficiently soluble or suspendable in aqueous or physiological media solutions). In one embodiment, the carbonic anhydrase targeting agent is water soluble or dispersible in aqueous media, and is biocompatible, i.e., non-toxic having, for example, an $LD_{50}$ of greater than about 50 mg/kg body weight. The carbonic anhydrase targeting agents preferably do not have any undesired phototoxic properties and/or display low serum protein binding affinity.

A list of exemplary carbonic anhydrase targeting agents is provided in Table 4.

TABLE 4

| Compound No. | Structure | Name |
|---|---|---|
| IV-1 | 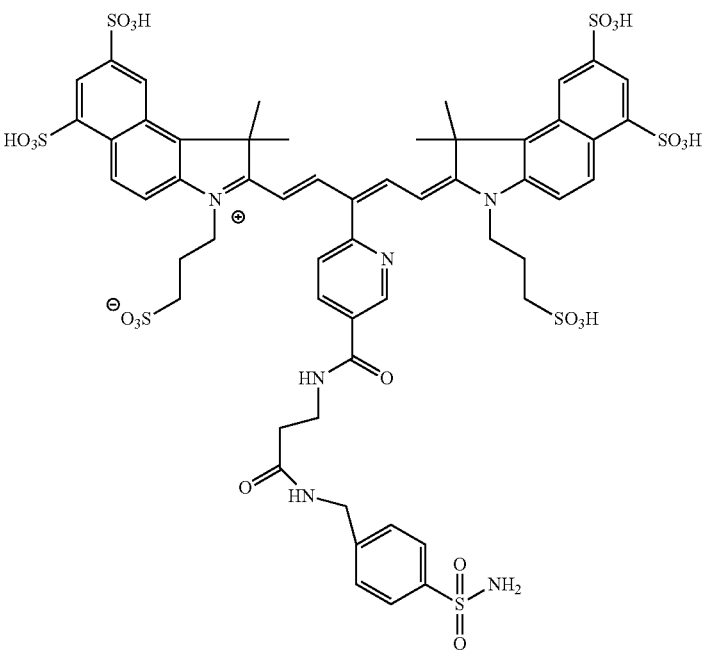 | 3-(2-((1E,3Z,5E)-5-(1,1-dimethyl-6,8-disulfo-3-(3-sulfopropyl)-1H-benzo[e]indol-2(3H)-ylidene)-3-(5-((3-oxo-3-((4-sulfamoylbenzyl)amino)propyl)carbamoyl)pyridin-2-yl)penta-1,3-dien-1-yl)-1,1-dimethyl-6,8-disulfo-1H-benzo[e]indol-3-ium-3-yl)propane-1-sulfonate |

TABLE 4-continued

| Compound No. | Structure | Name |
|---|---|---|
| IV-2 | 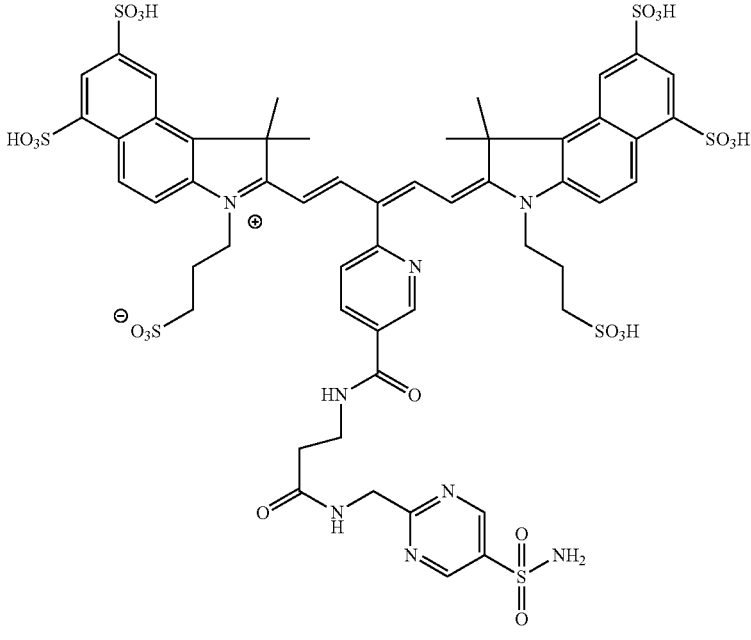 | 3-(2-((1E,3Z,5E)-5-(1,1-dimethyl-6,8-disulfo-3-(3-sulfopropyl)-1H-benzo[e]indol-2(3H)-ylidene)-3-(5-((3-oxo-3-(((5-sulfamoylpyrimidin-2-yl)methyl)amino)propyl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-3 | 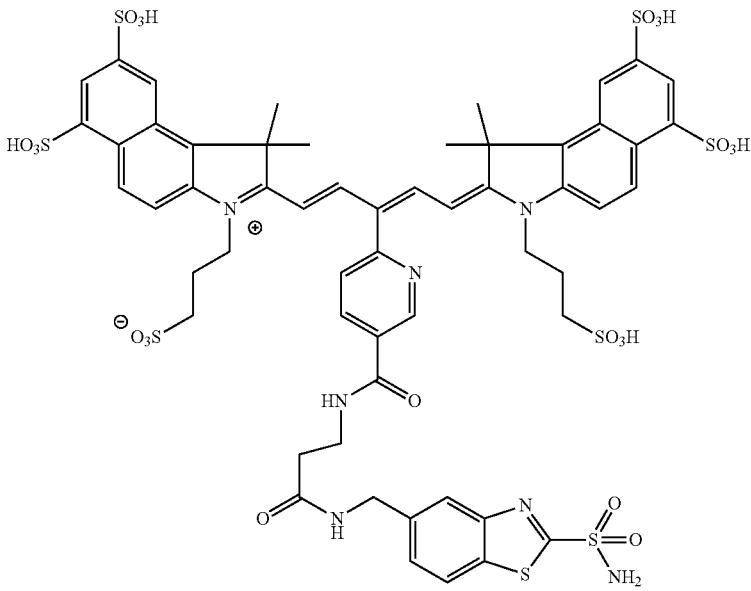 | 3-(2-((1E,3Z,5E)-5-(1,1-dimethyl-6,8-disulfo-3-(3-sulfopropyl)-1H-benzo[e]indol-2(3H)-ylidene)-3-(5-((3-oxo-3-(((2-sulfamoylbenzo[d]thiazol-5-yl)methyl)amino)propyl)carbamoyl)pyridin-2-yl)penta-1,3-dien-1-yl)-1,1-dimethyl-6,8-disulfo-1H-benzo[e]indol-3-ium-3-yl)propane-1-sulfonate |

TABLE 4-continued

| Compound No. | Structure | Name |
|---|---|---|
| IV-4 | 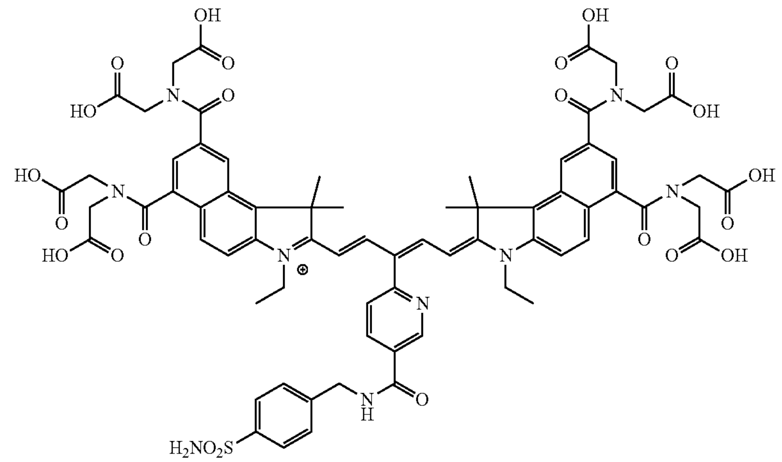 | 2-((1E,3Z,5E)-5-(6,8-bis(bis(carboxymethyl)carbamoyl)-3-ethyl-1,1-dimethyl-1H-benzo[e]indol-2(3H)-ylidene)-3-(5-(4-sulfamoylbenzylcarbamoyl)pyridin-2-yl)penta-1,3-dienyl)-6,8-bis(bis(carboxymethyl)carbamoyl)-3-ethyl-1,1-dimethyl-1H-benzo[e]indolium |
| IV-5 | 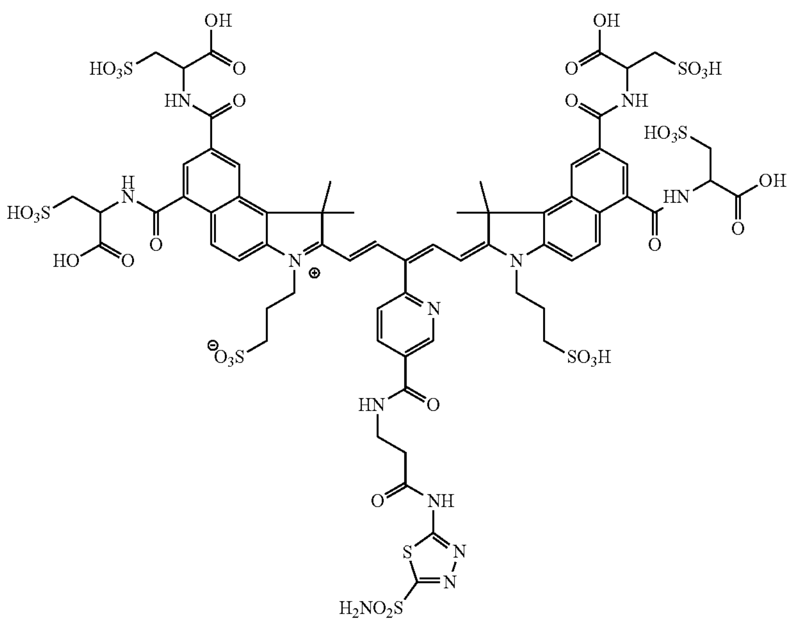 | 3-(2-((1E,3Z,5E)-5-(6,8-bis(1-carboxy-2-sulfoethylcarbamoyl)-1,1-dimethyl-3-(3-sulfopropyl)-1H-benzo[e]indol-2(3H)-ylidene)-3-(5-(3-oxo-3-(5-sulfamoyl-1,3,4-thiadiazol-2-ylamino)propylcarbamoyl)pyridin-2-yl)penta-1,3-dienyl)-6,8-bis(1-carboxy-2-sulfoethylcarbamoyl)-1,1-dimethyl-1H-benzo[e]indolium-3-yl)propane-1-sulfonate |
| IV-6 | 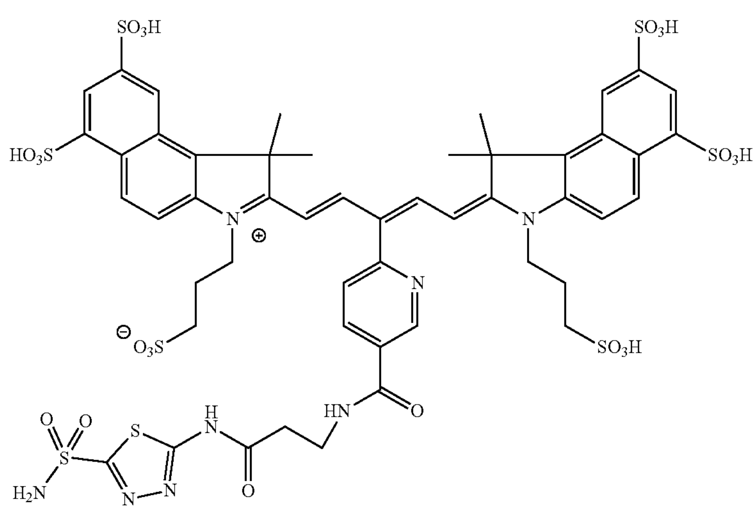 | 3-(2-((1E,3Z,5E)-5-(1,1-dimethyl-6,8-disulfo-3-(3-sulfopropyl)-1H-benzo[e]indol-2(3H)-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-1,1-dimethyl-6,8-disulfo-1H-benzo[e]indol-3-ium-3-yl)propane-1-sulfonate |

TABLE 4-continued

| Compound No. | Structure | Name |
|---|---|---|
| IV-7 | 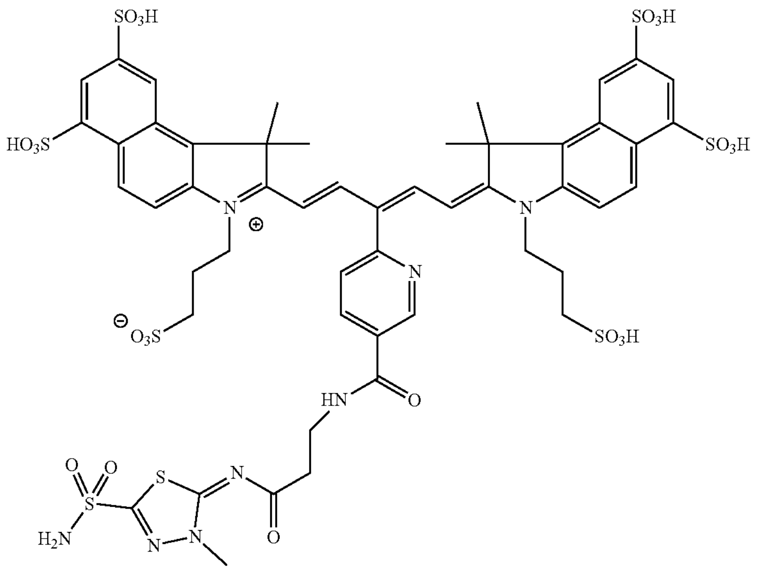 | 3-(2-((1E,3Z,5E)-5-(1,1-dimethyl-6,8-disulfo-3-(3-sulfopropyl)-1H-benzo[e]indol-2(3H)-ylidene)-3-(5-(3-((E)-3-methyl-5-sulfamoyl-1,3,4-thiadiazol-2(3H)-ylideneamino)-3-oxopropylcarbamoyl)pyridin-2-yl)penta-1,3-dienyl)-1,1-dimethyl-6,8-disulfo-1H-benzo[e]indolium-3-yl)propane-1-sulfonate |
| IV-8 | 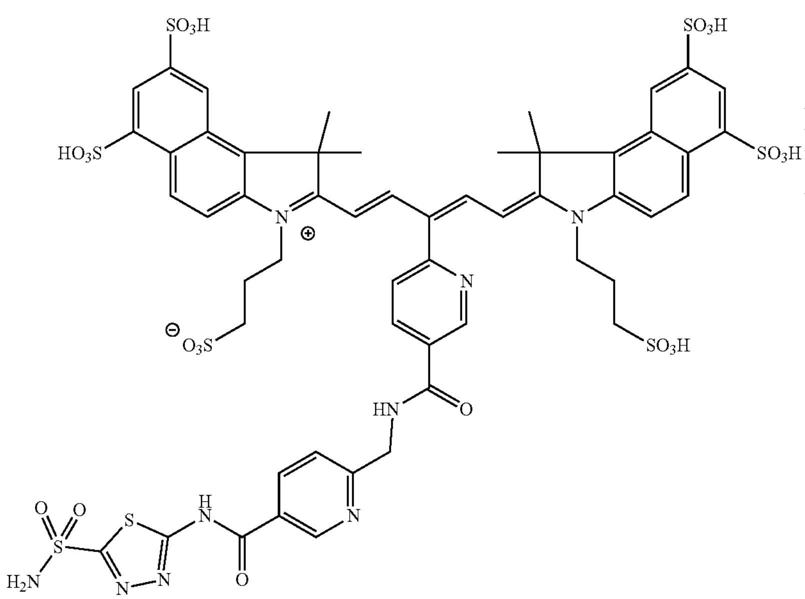 | 3-(2-((1E,3Z,5E)-5-(1,1-dimethyl-6,8-disulfo-3-(3-sulfopropyl)-1H-benzo[e]indol-2(3H)-ylidene)-3-(5-(((5-((5-sulfamoyl-1,3,4-thiadiazol-2-yl)carbamoyl)pyridin-2-yl)methyl)carbamoyl)pyridin-2-yl)penta-1,3-dien-1-yl)-1,1-dimethyl-6,8-disulfo-1H-benzo[e]indol-3-ium-3-yl)propane-1-sulfonate |

TABLE 4-continued

| Compound No. | Structure | Name |
|---|---|---|
| IV-9 | 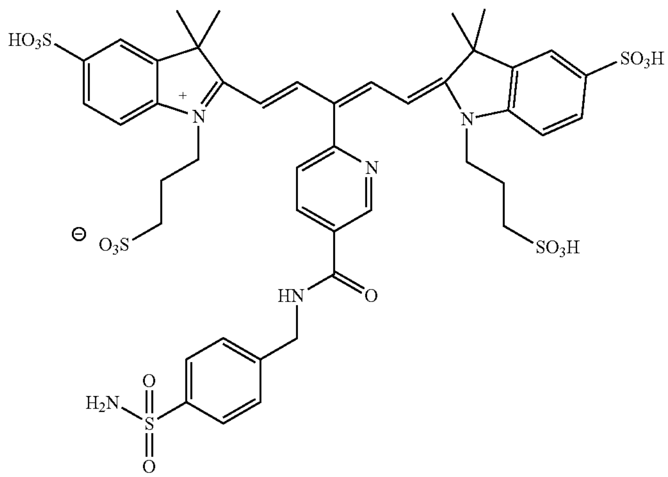 | 3-(2-((1E,3Z,5E)-5-(3,3-dimethyl-5-sulfo-1-(3-sulfopropyl)indolin-2-ylidene)-3-(5-(4-sulfamoylbenzylcarbamoyl)pyridin-2-yl)penta-1,3-dienyl)-3,3-dimethyl-5-sulfo-3H-indolium-1-yl)propane-1-sulfonate |
| IV-10 | 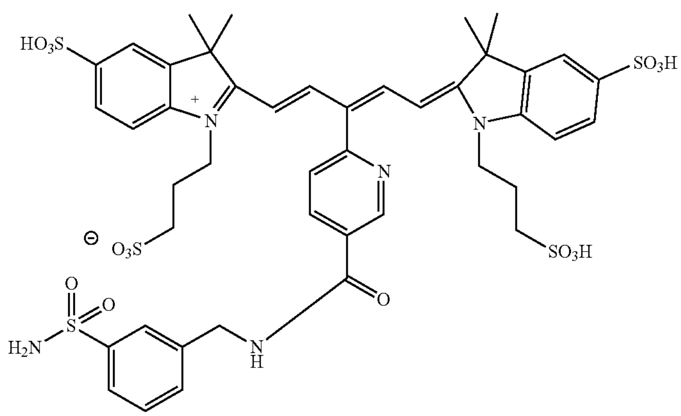 | 3-(2-((1E,3Z,5E)-5-(3,3-dimethyl-5-sulfo-1-(3-sulfopropyl)indolin-2-ylidene)-3-(5-(3-sulfamoylbenzylcarbamoyl)pyridin-2-yl)penta-1,3-dienyl)-3,3-dimethyl-5-sulfo-3H-indolium-1-yl)propane-1-sulfonate |
| IV-11 | 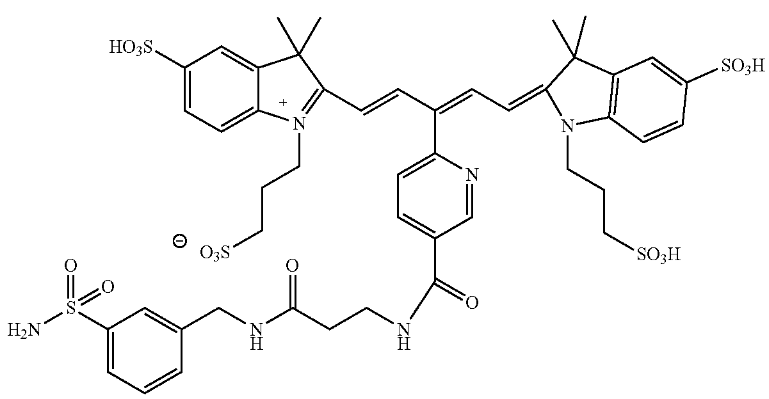 | 3-(2-((1E,3Z,5E)-5-(3,3-dimethyl-5-sulfo-1-(3-sulfopropyl)indolin-2-ylidene)-3-(5-(3-oxo-3-(3-sulfamoylbenzylamino)propylcarbamoyl)pyridin-2-yl)penta-1,3-dienyl)-3,3-dimethyl-5-sulfo-3H-indolium-1-yl)propane-1-sulfonate |

TABLE 4-continued

| Compound No. | Structure | Name |
|---|---|---|
| IV-12 | 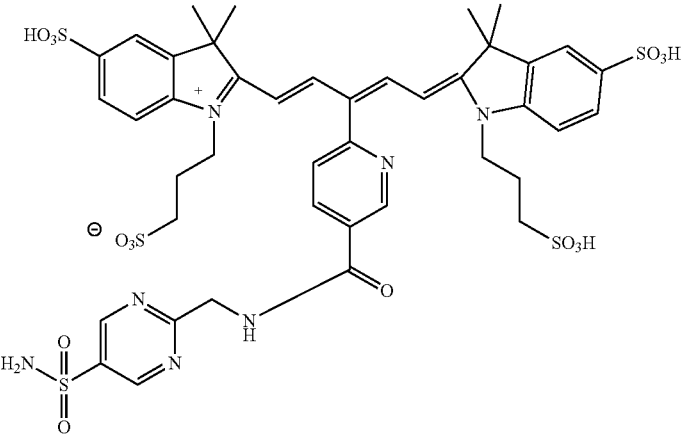 | 3-(2-((1E,3Z,5E)-5-(3,3-dimethyl-5-sulfo-1-(3-sulfopropyl)indolin-2-ylidene)-3-(5-((5-sulfamoylpyrimidin-2-yl)methylcarbamoyl)pyridin-2-yl)penta-1,3-dienyl)-3,3-dimethyl-5-sulfo-3H-indolium-1-yl)propane-1-sulfonate |
| IV-13 | 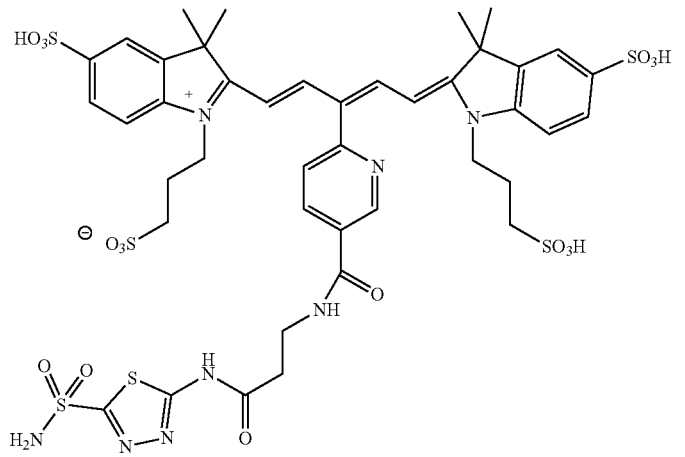 | 3-(2-((1E,3Z,5E)-5-(3,3-dimethyl-5-sulfo-1-(3-sulfopropyl)indolin-2-ylidene)-3-(5-(3-oxo-3-(5-sulfamoyl-1,3,4-thiadiazol-2-ylamino)propylcarbamoyl)pyridin-2-yl)penta-1,3-dienyl)-3,3-dimethyl-5-sulfo-3H-indolium-1-yl)propane-1-sulfonate |
| IV-14 | 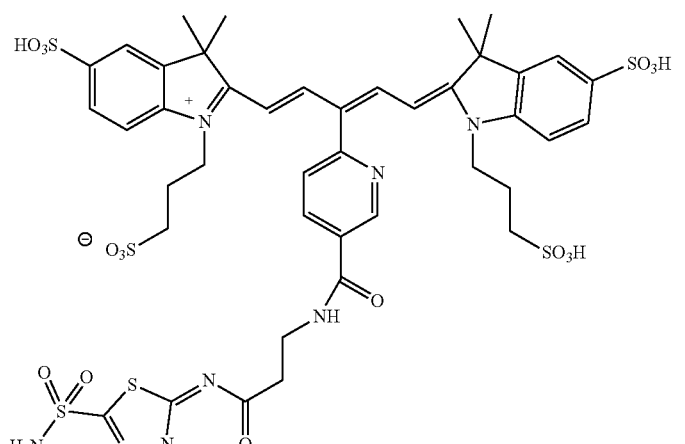 | 3-(2-((1E,3Z,5E)-5-(3,3-dimethyl-5-sulfo-1-(3-sulfopropyl)indolin-2-ylidene)-3-(5-(3-((E)-3-methyl-5-sulfamoyl-1,3,4-thiadiazol-2(3H)-ylideneamino)-3-oxopropylcarbamoyl)pyridin-2-yl)penta-1,3-dienyl)-3,3-dimethyl-5-sulfo-3H-indolium-1-yl)propane-1-sulfonate |

TABLE 4-continued

| Compound No. | Structure | Name |
|---|---|---|
| IV-15 | 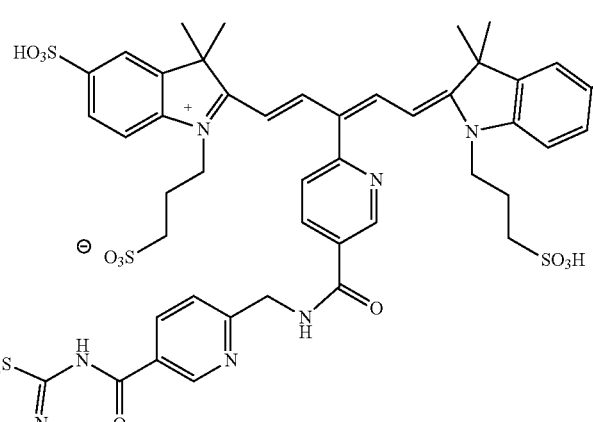 | 3-(2-((1E,3Z,5E)-5-(3,3-dimethyl-5-sulfo-1-(3-sulfopropyl)indolin-2-ylidene)-3-(5-((5-(5-sulfamoyl-1,3,4-thiadiazol-2-ylcarbamoyl)pyridin-2-yl)methylcarbamoyl)pyridin-2-yl)penta-1,3-dienyl)-3,3-dimethyl-5-sulfo-3H-indolium-1-yl)propane-1-sulfonate |
| IV-16 | 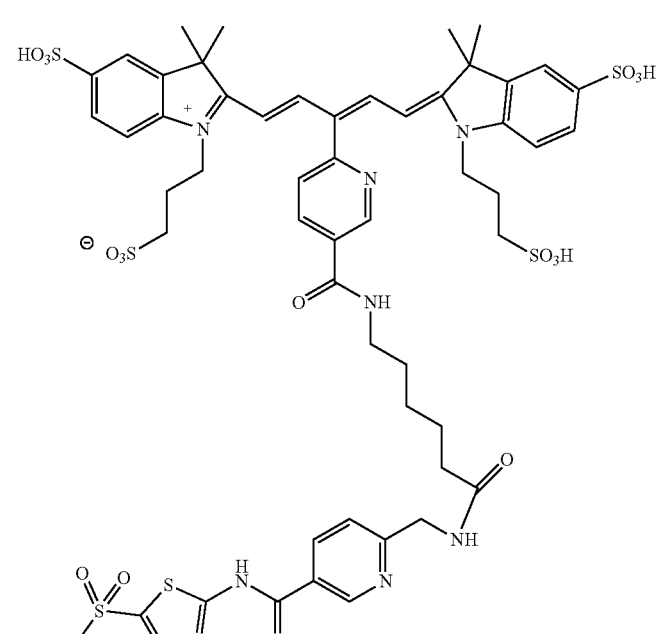 | 3-(2-((1E,3Z,5E)-5-(3,3-dimethyl-5-sulfo-1-(3-sulfopropyl)indolin-2-ylidene)-3-(5-((6-oxo-6-(((5-((5-sulfamoyl-1,3,4-thiadiazol-2-yl)carbamoyl)pyridin-2-yl)methyl)amino)hexyl)carbamoyl)pyridin-2-yl)penta-1,3-dien-1-yl)-3,3-dimethyl-5-sulfo-3H-indol-1-ium-1-yl)propane-1-sulfonate |

TABLE 4-continued

| Compound No. | Structure | Name |
|---|---|---|
| IV-17 | 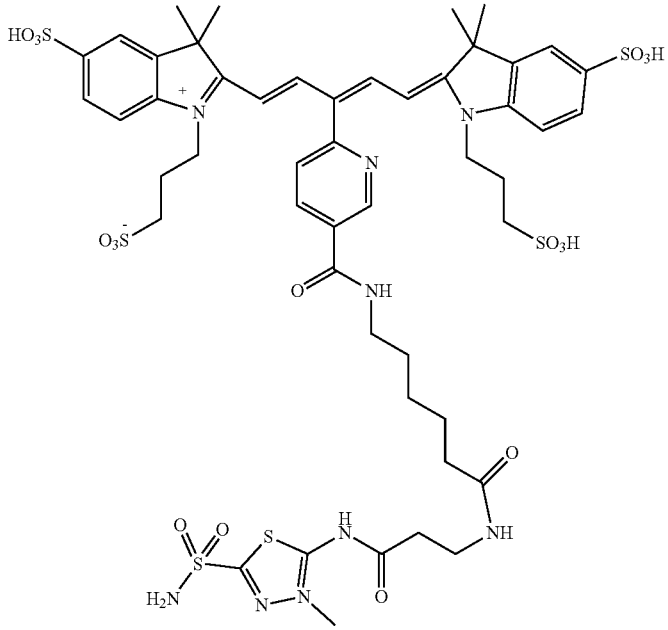 | 3-(2-((1E,3Z,5E)-5-(3,3-dimethyl-5-sulfo-1-(3-sulfopropyl)indolin-2-ylidene)-3-(5-((6-((3-((3-methyl-5-sulfamoyl-1,3,4-thiadiazol-3-ium-2-yl)amino)-3-oxopropyl)amino)-6-oxohexyl)carbamoyl)pyridin-2-yl)penta-1,3-dien-1-yl)-3,3-dimethyl-5-sulfo-3H-indol-1-ium-1-yl)propane-1-sulfonate |
| IV-18 | 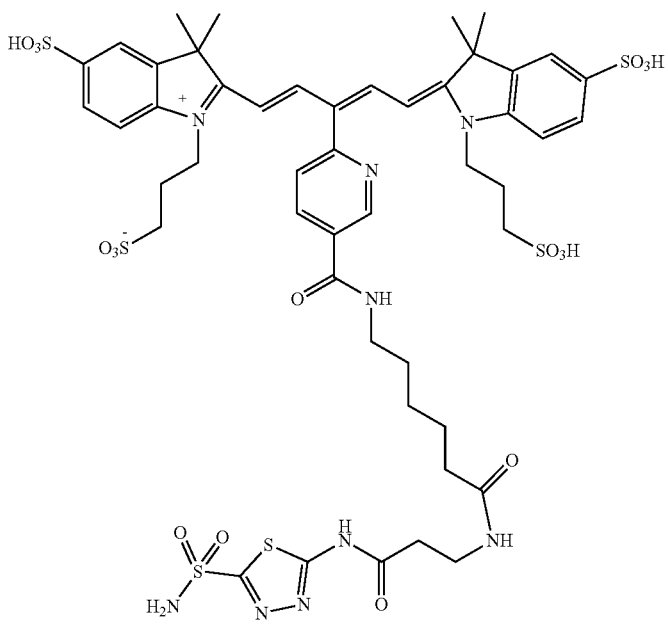 | 3-(2-((1E,3Z,5E)-5-(3,3-dimethyl-5-sulfo-1-(3-sulfopropyl)indolin-2-ylidene)-3-(5-((6-oxo-6-((3-oxo-3-((5-sulfamoyl-1,3,4-thiadiazol-2-yl)amino)propyl)amino)hexyl)carbamoyl)pyridin-2-yl)penta-1,3-dien-1-yl)-3,3-dimethyl-5-sulfo-3H-indol-1-ium-1-yl)propane-1-sulfonate |

TABLE 4-continued

| Compound No. | Structure | Name |
|---|---|---|
| IV-19 | 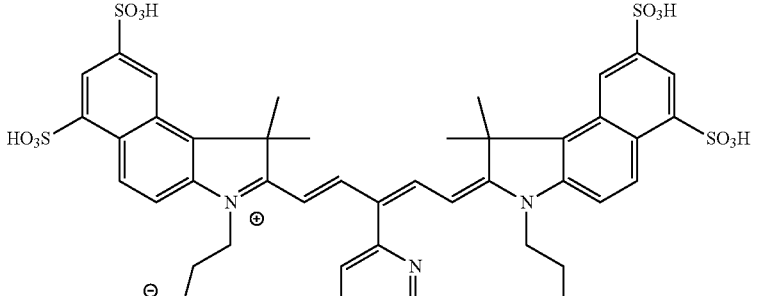 | 2-(2-((1E,3Z,5E)-5-(1,1-dimethyl-6,8-disulfo-3-(2-sulfoethyl)-1H-benzo[e]indol-2(3H)-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-1,1-dimethyl-6,8-disulfo-1H-benzo[e]indol-3-ium-3-yl)ethanesulfonate |
| IV-20 | 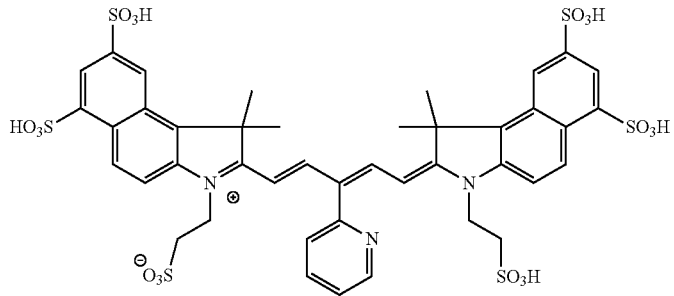 | 2-(2-((1E,3Z,5E)-5-(1,1-dimethyl-6,8-disulfo-3-(2-sulfoethyl)-1H-benzo[e]indol-2(3H)-ylidene)-3-(5-((6-oxo-6-((3-oxo-3-((5-sulfamoyl-1,3,4-thiadiazol-2-yl)amino)propyl)amino)hexyl)carbamoyl)pyridin-2-yl)penta-1,3-dien-1-yl)-1,1-dimethyl-6,8-disulfo-1H-benzo[e]indol-3-ium-3-yl)ethanesulfonate |

TABLE 4-continued

| Compound No. | Structure | Name |
|---|---|---|
| IV-21 | 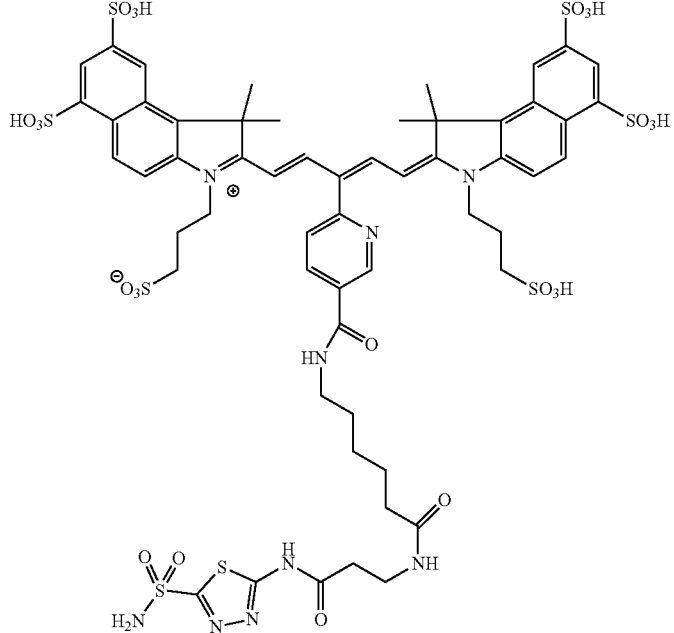 | 3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-((3-oxo-3-((5-sulfamoyl-1,3,4-thiadiazol-2-yl)amino)propyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-22 | 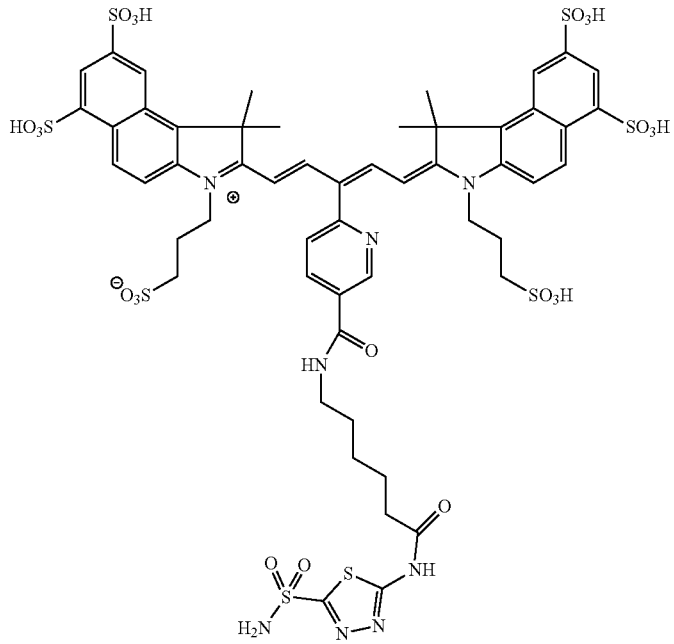 | 3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-((5-sulfamoyl-1,3,4-thiadiazol-2-yl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate |

TABLE 4-continued

| Compound No. | Structure | Name |
|---|---|---|
| IV-23 | 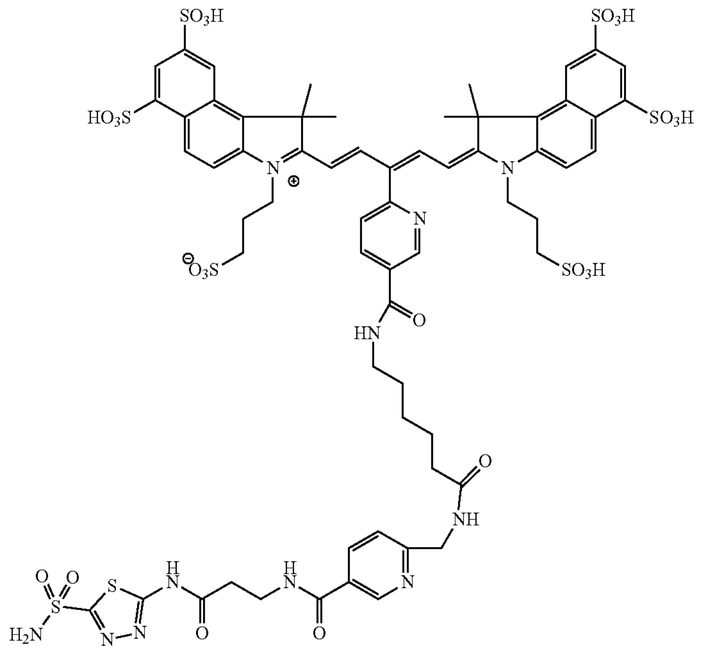 | 3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-(((5-((3-oxo-3-((5-sulfamoyl-1,3,4-thiadiazol-2-yl)amino)propyl)carbamoyl)pyridin-2-yl)methyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-24 | 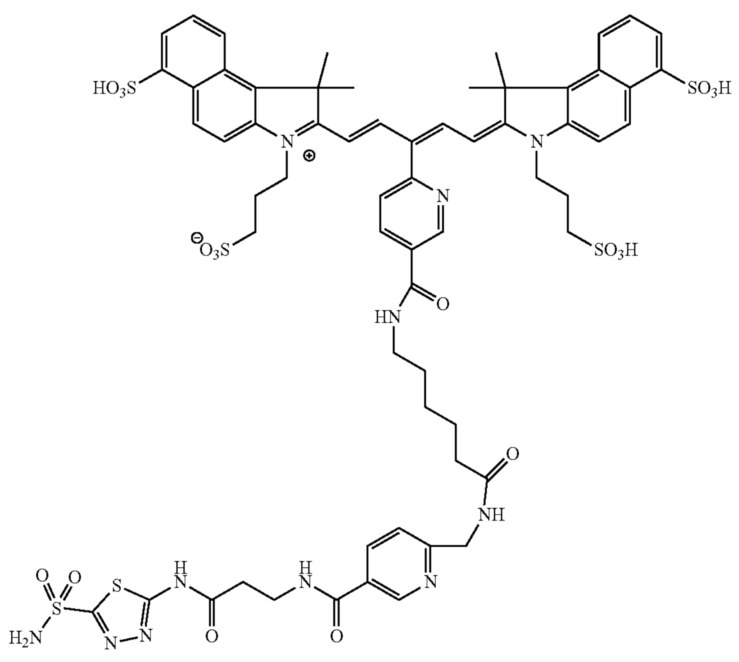 | 3-(2-((1E,3Z,5E)-5-(1,1-dimethyl-6-sulfo-3-(3-sulfopropyl)-1H-benzo[e]indol-2(3H)-ylidene)-3-(5-((6-oxo-6-(((5-((3-oxo-3-((5-sulfamoyl-1,3,4-thiadiazol-2-yl)amino)propyl)carbamoyl)pyridin-2-yl)methyl)amino)hexyl)carbamoyl)pyridin-2-yl)penta-1,3-dien-1-yl)-1,1-dimethyl-6-sulfo-1H-benzo[e]indol-3-ium-3-yl)propane-1-sulfonate |

TABLE 4-continued

| Compound No. | Structure | Name |
|---|---|---|
| IV-25 | 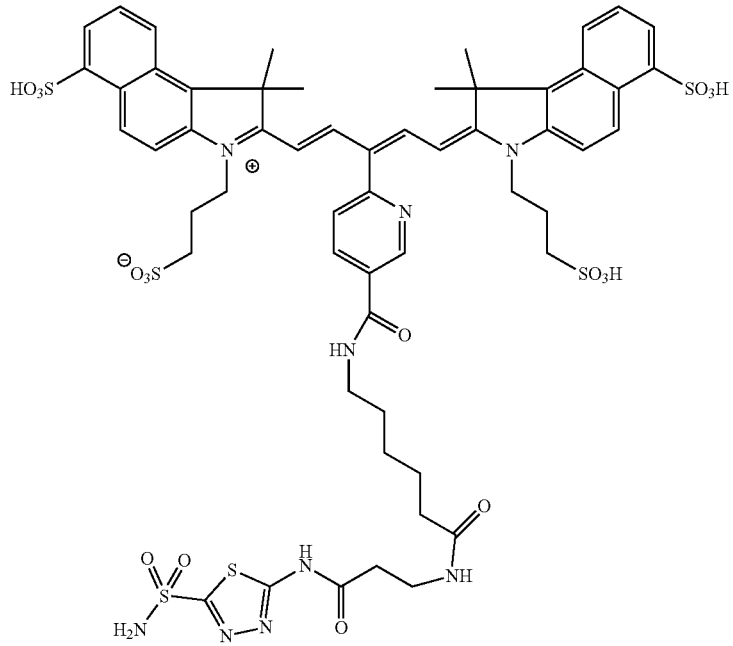 | 3-(2-((1E,3Z,5E)-5-(1,1-dimethyl-6-sulfo-3-(3-sulfopropyl)-1H-benzo[e]indol-2(3H)-ylidene)-3-(5-((6-oxo-6-((3-oxo-3-((5-sulfamoyl-1,3,4-thiadiazol-2-yl)amino)propyl)amino)hexyl)carbamoyl)pyridin-2-yl)penta-1,3-dien-1-yl)-1,1-dimethyl-6-sulfo-1H-benzo[e]indol-3-ium-3-yl)propane-1-sulfonate |
| IV-26 | 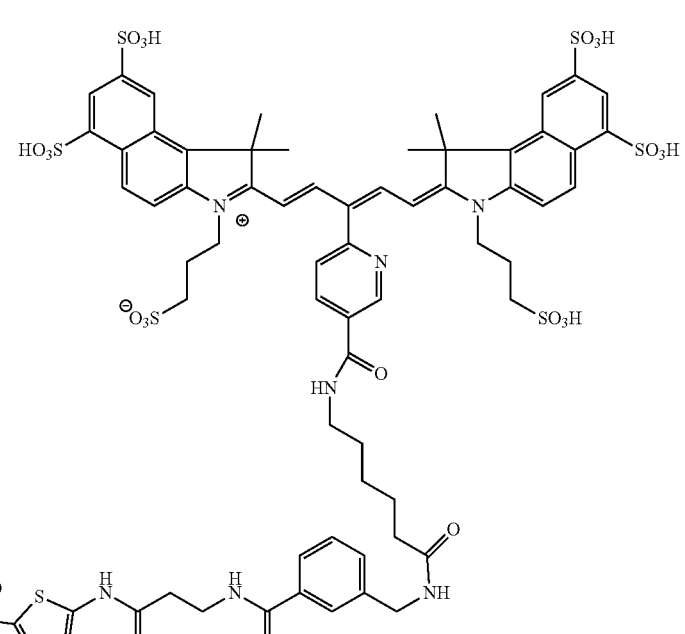 | 3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-((3-((3-oxo-3-((5-sulfamoyl-1,3,4-thiadiazol-2-yl)amino)propyl)carbamoyl)benzyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate |

TABLE 4-continued

| Compound No. | Structure | Name |
|---|---|---|
| IV-27 | 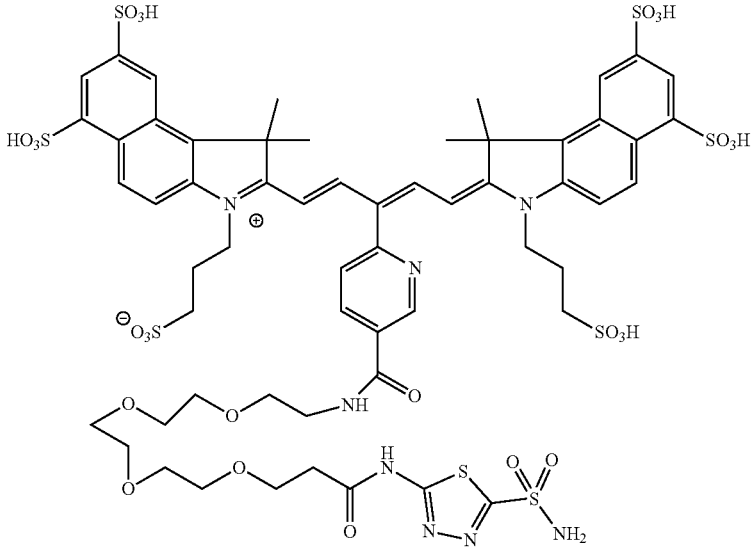 | 3-(2-((1E,3Z,5E)-5-(1,1-dimethyl-6,8-disulfo-3-(3-sulfopropyl)-1H-benzo[e]indol-2(3H)-ylidene)-3-(5-((15-oxo-15-((5-sulfamoyl-1,3,4-thiadiazol-2-yl)amino)-3,6,9,12-tetraoxapentadecyl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-28 | 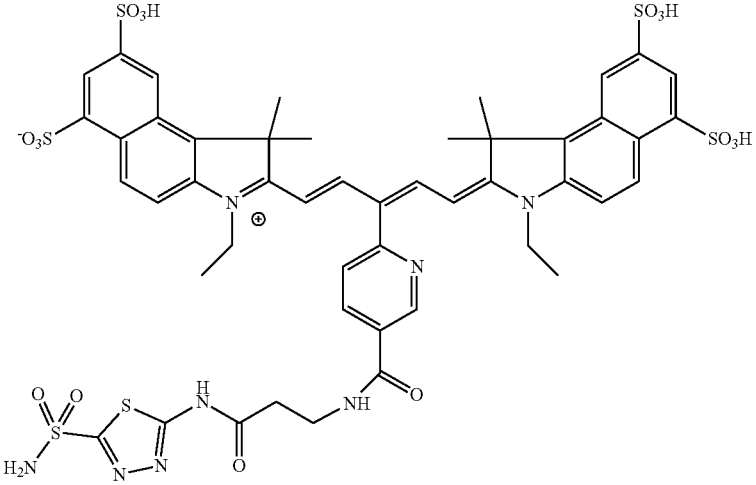 | 3-ethyl-2-((1E,3Z,5E)-5-(3-ethyl-1,1-dimethyl-6,8-disulfo-1H-benzo[e]indol-2(3H)-ylidene)-3-(5-(3-oxo-3-(5-sulfamoyl-1,3,4-thiadiazol-2-ylamino)propylcarbamoyl)pyridin-2-yl)penta-1,3-dienyl)-1,1-dimethyl-8-sulfo-1H-benzo[e]indolium-6-sulfonate |
| IV-29 | 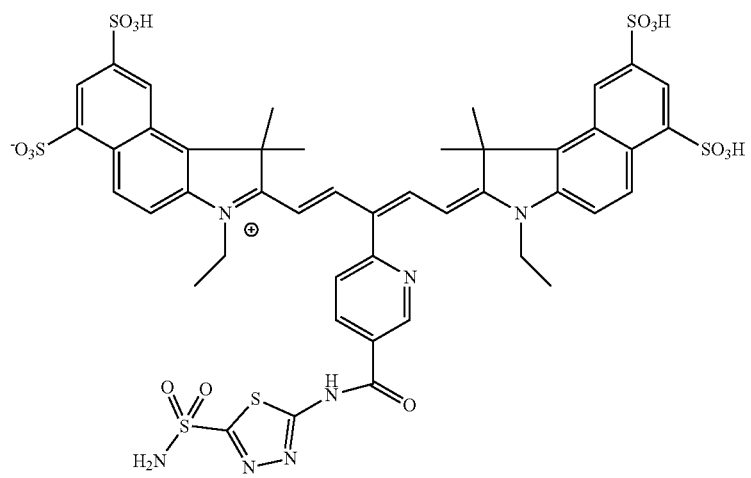 | 3-ethyl-2-((1E,3Z,5E)-5-(3-ethyl-1,1-dimethyl-6,8-disulfo-1H-benzo[e]indol-2(3H)-ylidene)-3-(5-(5-sulfamoyl-1,3,4-thiadiazol-2-ylcarbamoyl)pyridin-2-yl)penta-1,3-dienyl)-1,1-dimethyl-8-sulfo-1H-benzo[e]indolium-6-sulfonate |

| Compound No. | Structure | Name |
|---|---|---|
| IV-30 | 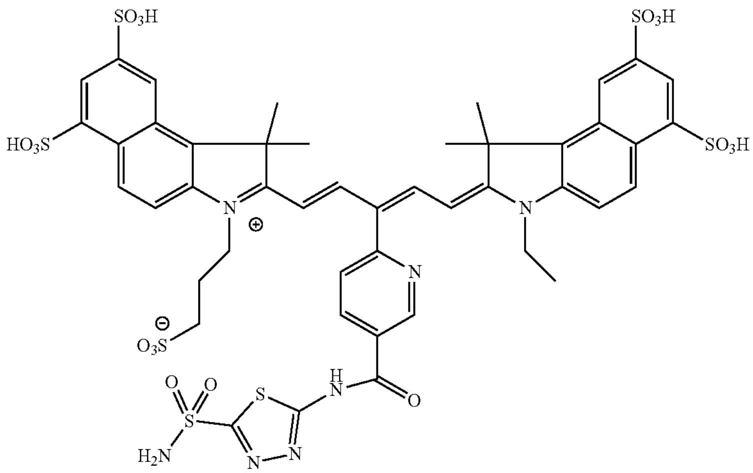 | 3-(2-((1E,3Z,5E)-5-(3-ethyl-1,1-dimethyl-6,8-disulfo-1H-benzo[e]indol-2(3H)-ylidene)-3-(5-((5-sulfamoyl-1,3,4-thiadiazol-2-yl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-31 | 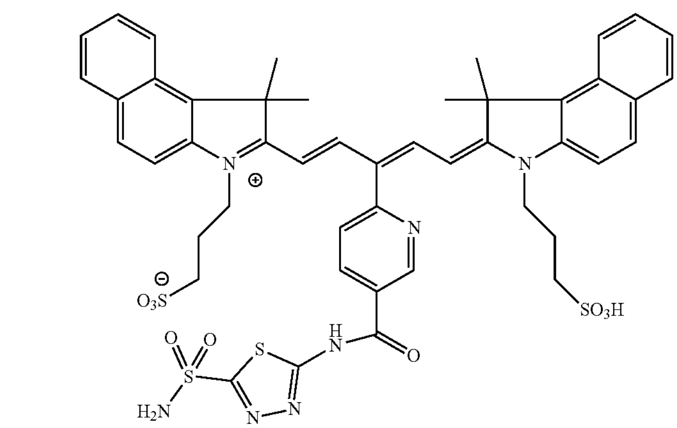 | 3-(2-((1E,3Z,5E)-5-(1,1-dimethyl-3-(3-sulfopropyl)-1H-benzo[e]indol-2(3H)-ylidene)-3-(5-((5-sulfamoyl-1,3,4-thiadiazol-2-yl)carbamoyl)pyridin-2-yl)penta-1,3-dien-1-yl)-1,1-dimethyl-1H-benzo[e]indol-3-ium-3-yl)propane-1-sulfonate |
| IV-32 | 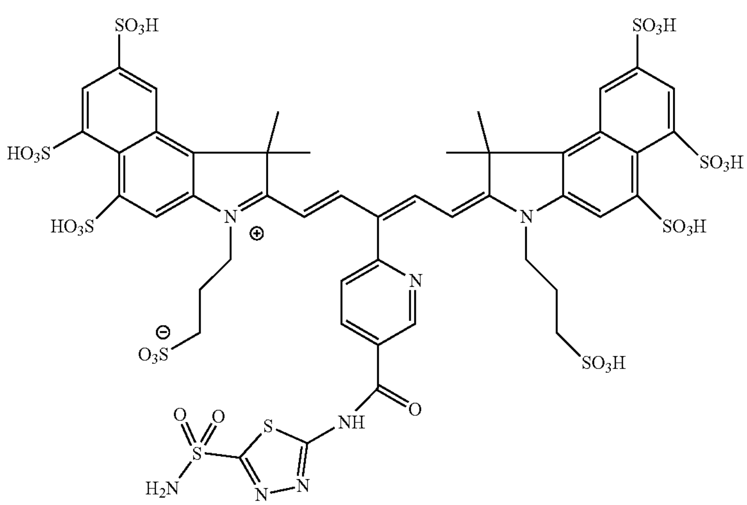 | 3-(2-((1E,3Z,5E)-5-(1,1-dimethyl-5,6,8-trisulfo-3-(3-sulfopropyl)-1H-benzo[e]indol-2(3H)-ylidene)-3-(5-((5-sulfamoyl-1,3,4-thiadiazol-2-yl)carbamoyl)pyridin-2-yl)penta-1,3-dien-1-yl)-1,1-dimethyl-5,6,8-trisulfo-1H-benzo[e]indol-3-ium-3-yl)propane-1-sulfonate |

TABLE 4-continued

| Compound No. | Structure | Name |
|---|---|---|
| IV-33 | 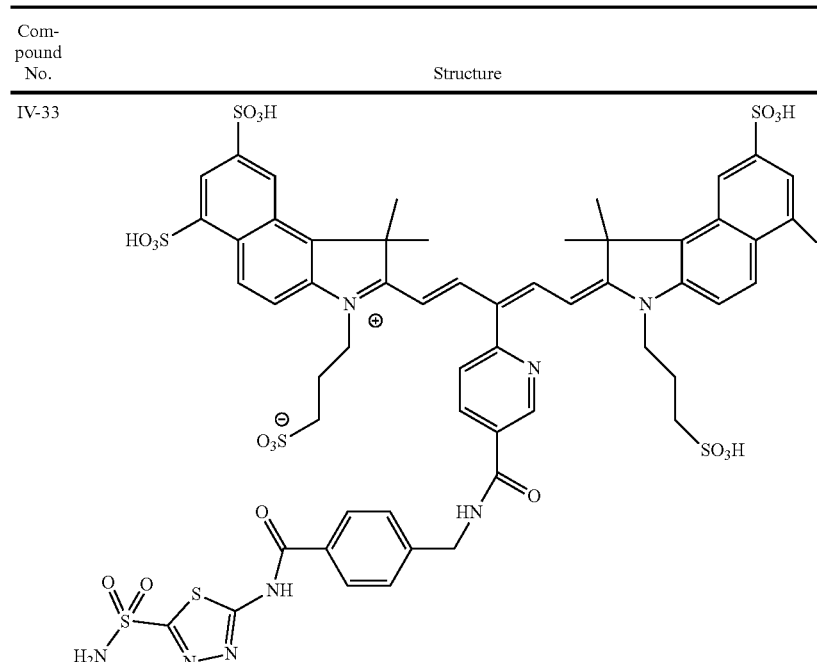 | 3-(2-((1E,3Z,5E)-5-(1,1-dimethyl-6,8-disulfo-3-(3-sulfopropyl)-1H-benzo[e]indol-2(3H)-ylidene)-3-(5-((4-((5-sulfamoyl-1,3,4-thiadiazol-2-yl)carbamoyl)benzyl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-34 | 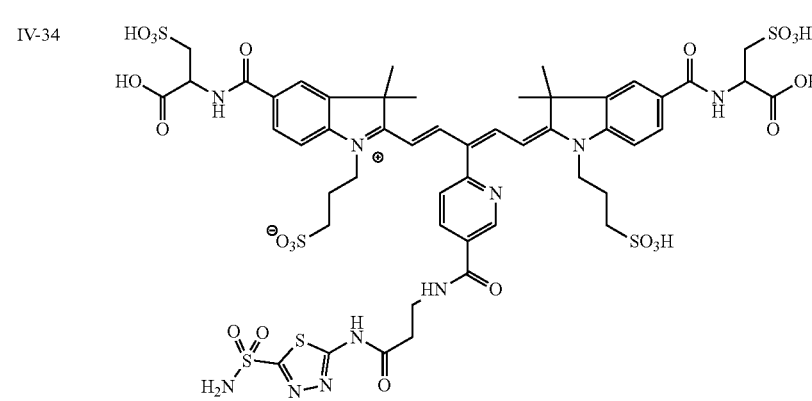 | 3-(5-((1-carboxy-2-sulfoethyl)carbamoyl)-2-((1E,3Z,5E)-5-(5-((1-carboxy-2-sulfoethyl)carbamoyl)-3,3-dimethyl-1-(3-sulfopropyl)indolin-2-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-3,3-dimethyl-3H-indol-1-ium-1-yl)propane-1-sulfonate |
| IV-35 | 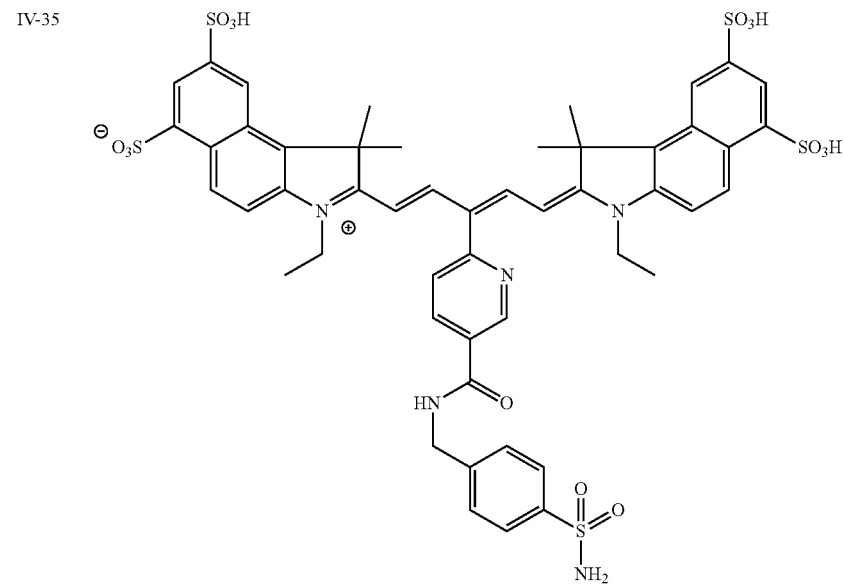 | 3-ethyl-2-((1E,3Z,5E)-5-(3-ethyl-1,1-dimethyl-6,8-disulfo-1H-benzo[e]indol-2(3H)-ylidene)-3-(5-((4-sulfamoylbenzyl)carbamoyl)pyridin-2-yl)penta-1,3-dien-1-yl)-1,1-dimethyl-8-sulfo-1H-benzo[e]indol-3-ium-6-sulfonate |

TABLE 4-continued
| Compound No. | Structure | Name |
|---|---|---|
| IV-36 | 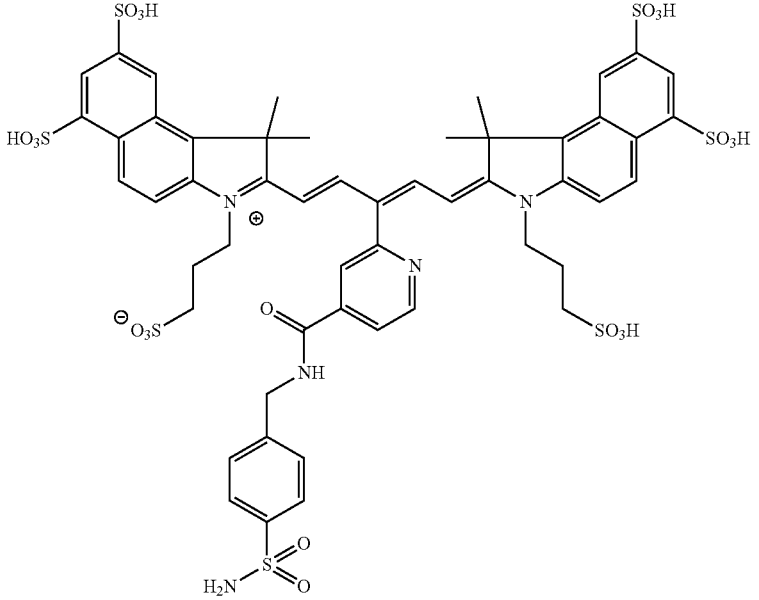 | 3-(2-((1E,3Z,5E)-5-(1,1-dimethyl-6,8-disulfo-3-(3-sulfopropyl)-1H-benzo[e]indol-2(3H)-ylidene)-3-(4-((4-sulfamoylbenzyl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-37 | 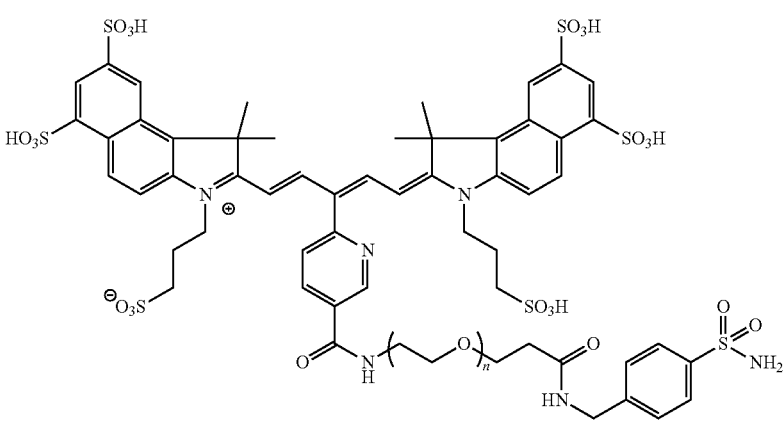<br>N = 3, 4, 8, 12, or 24 | N/A |

TABLE 4-continued

| Compound No. | Structure | Name |
|---|---|---|
| IV-38 | 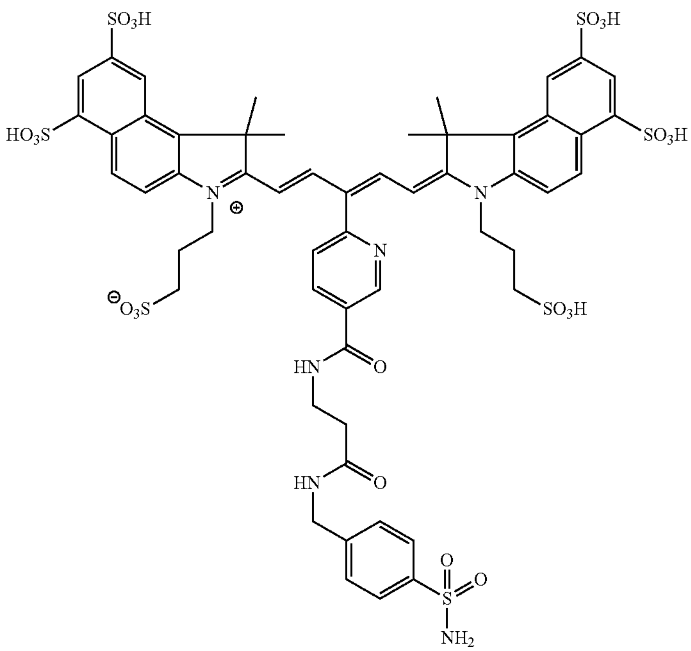 | 3-(2-((1E,3Z,5E)-5-(1,1-dimethyl-6,8-disulfo-3-(3-sulfopropyl)-1H-benzo[e]indol-2(3H)-ylidene)-3-(5-((3-oxo-3-((4-sulfamoylbenzyl)amino)propyl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-39 | 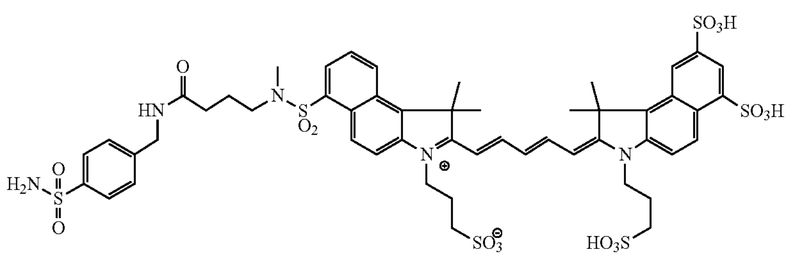 | 3-(2-((1E,3E,5E)-5-(1,1-dimethyl-6,8-disulfo-3-(3-sulfopropyl)-1H-benzo[e]indol-2(3H)-ylidene)penta-1,3-dien-1-yl)-1,1-dimethyl-6-(N-methyl-N-(4-oxo-4-((4-sulfamoylbenzyl)amino)butyl)sulfamoyl)-1H-benzo[e]indol-3-ium-3-yl)propane-1-sulfonate |
| IV-40 | 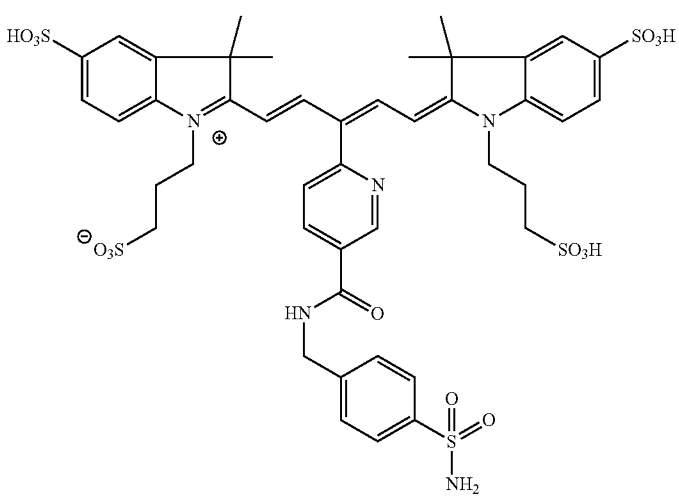 | 3-(2-((1E,3Z,5E)-5-(3,3-dimethyl-5-sulfo-1-(3-sulfopropyl)indolin-2-ylidene)-3-(5-((4-sulfamoylbenzyl)carbamoyl)pyridin-2-yl)penta-1,3-dien-1-yl)-3,3-dimethyl-5-sulfo-3H-indol-1-ium-1-yl)propane-1-sulfonate |

TABLE 4-continued

| Compound No. | Structure | Name |
|---|---|---|
| IV-41 | 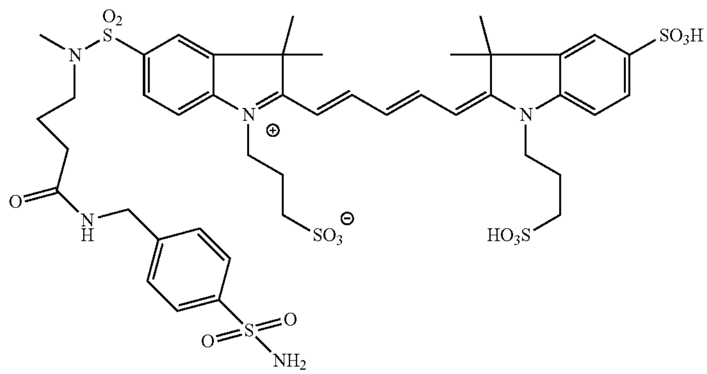 | 3-(2-((1E,3E,5E)-5-(3,3-dimethyl-5-sulfo-1-(3-sulfopropyl)indolin-2-ylidene)penta-1,3-dien-1-yl)-3,3-dimethyl-5-(N-methyl-N-(4-oxo-4-((4-sulfamoylbenzyl)amino)butyl)sulfamoyl)-3H-indol-1-ium-1-yl)propane-1-sulfonate |
| IV-42 | 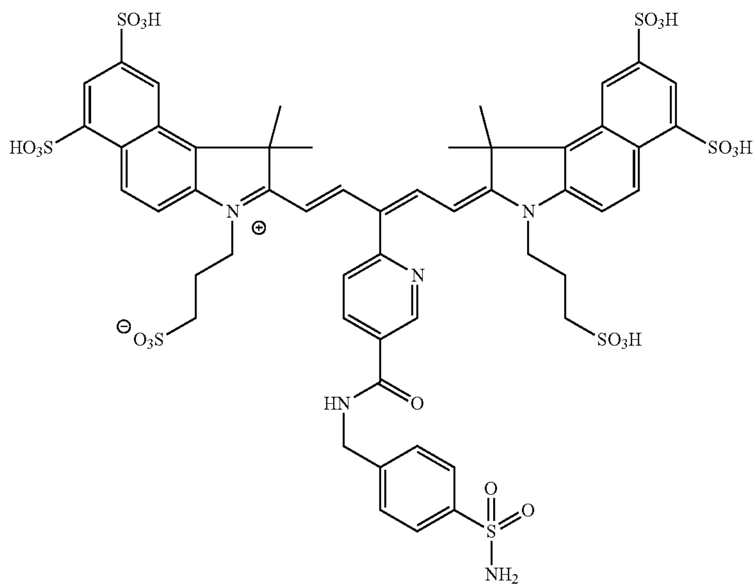 | 2-((1E,3Z,5E)-5-(1,1-dimethyl-6,8-disulfo-3-(3-sulfopropyl)-1H-benzo[e]indol-2(3H)-ylidene)-3-(5-((4-sulfamoylbenzyl)carbamoyl)pyridin-2-yl)penta-1,3-dien-1-yl)-1,1-dimethyl-8-sulfo-3-(3-sulfopropyl)-1H-benzo[e]indol-3-ium-6-sulfonate |
| IV-43 | 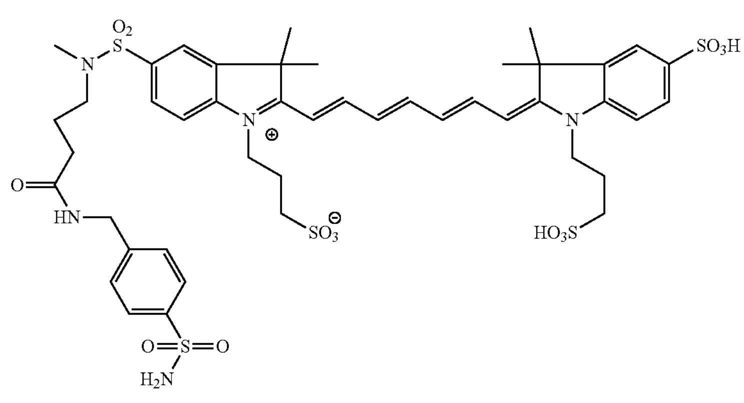 | 3-(2-((1E,3E,5E,7E)-7-(3,3-dimethyl-5-sulfo-1-(3-sulfopropyl)indolin-2-ylidene)hepta-1,3,5-trien-1-yl)-3,3-dimethyl-5-(N-methyl-N-(4-oxo-4-((4-sulfamoylbenzyl)amino)butyl)sulfamoyl)-3H-indol-1-ium-1-yl)propane-1-sulfonate |

TABLE 4-continued

| Compound No. | Structure | Name |
|---|---|---|
| IV-44 | 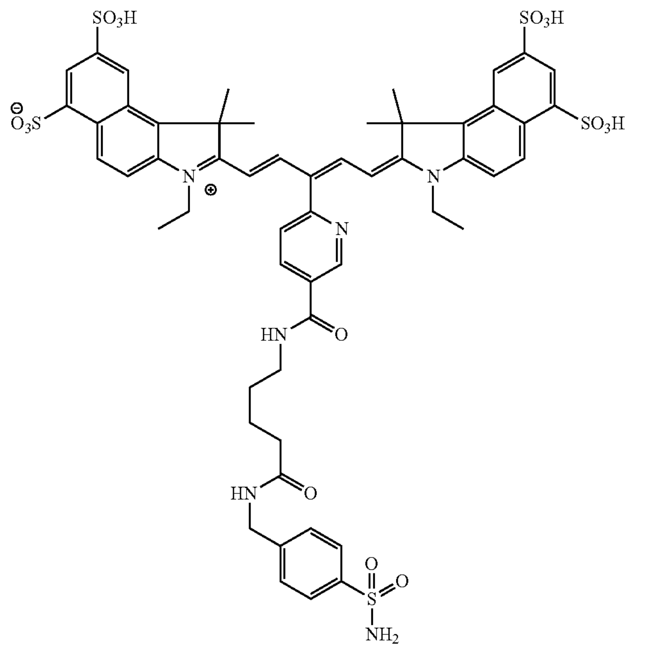 | 3-ethyl-2-((1E,3Z,5E)-5-(3-ethyl-1,1-dimethyl-6,8-disulfo-1H-benzo[e]indol-2(3H)-ylidene)-3-(5-((5-oxo-5-((4-sulfamoylbenzyl)amino)pentyl)carbamoyl)pyridin-2-yl)penta-1,3-dien-1-yl)-1,1-dimethyl-8-sulfo-1H-benzo[e]indol-3-ium-6-sulfonate |
| IV-45 | 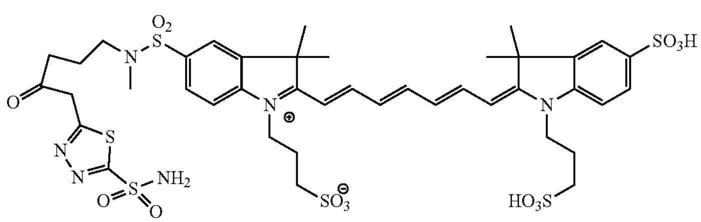 | 3-(2-((1E,3E,5E,7E)-7-(3,3-dimethyl-5-sulfo-1-(3-sulfopropyl)indolin-2-ylidene)hepta-1,3,5-trien-1-yl)-3,3-dimethyl-5-(N-methyl-N-(4-oxo-4-((5-sulfamoyl-1,3,4-thiadiazol-2-yl)amino)butyl)sulfamoyl)-3H-indol-1-ium-1-yl)propane-1-sulfonate |
| IV-46 | 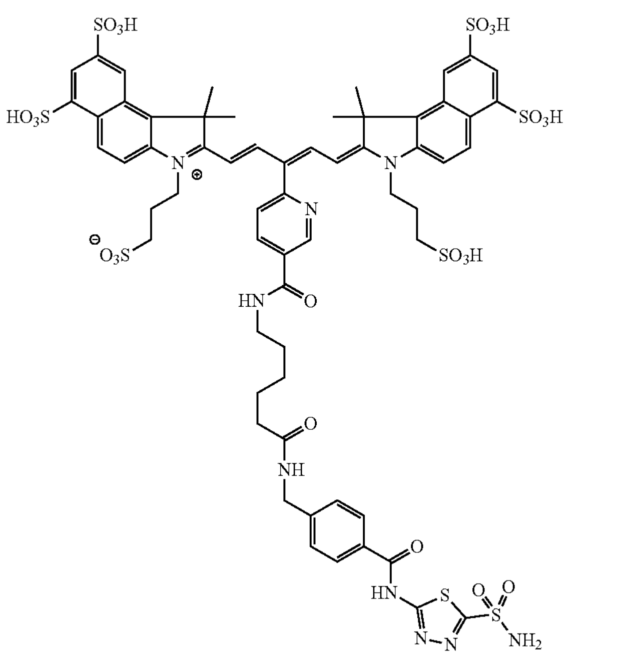 | 3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-((4-((5-sulfamoyl-1,3,4-thiadiazol-2-yl)carbamoyl)benzyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate |

TABLE 4-continued

| Compound No. | Structure | Name |
|---|---|---|
| IV-47 | 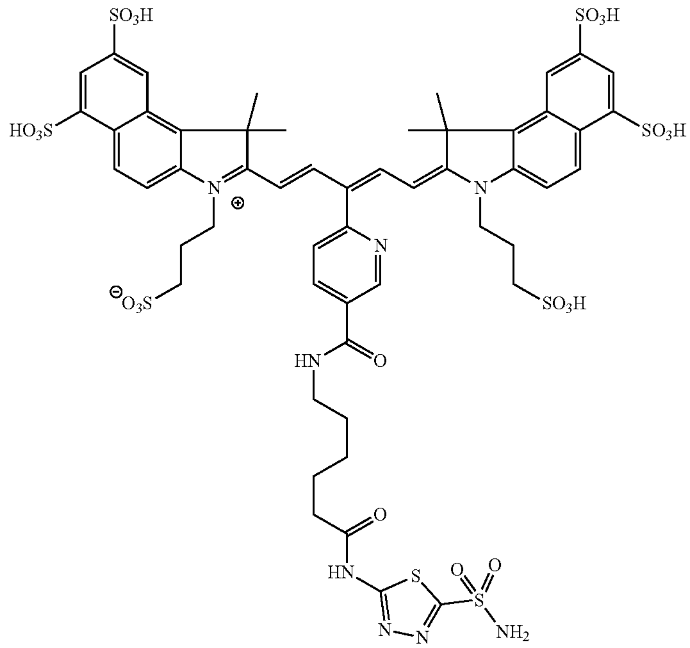 | 3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-((5-sulfamoyl-1,3,4-thiadiazol-2-yl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-48 | 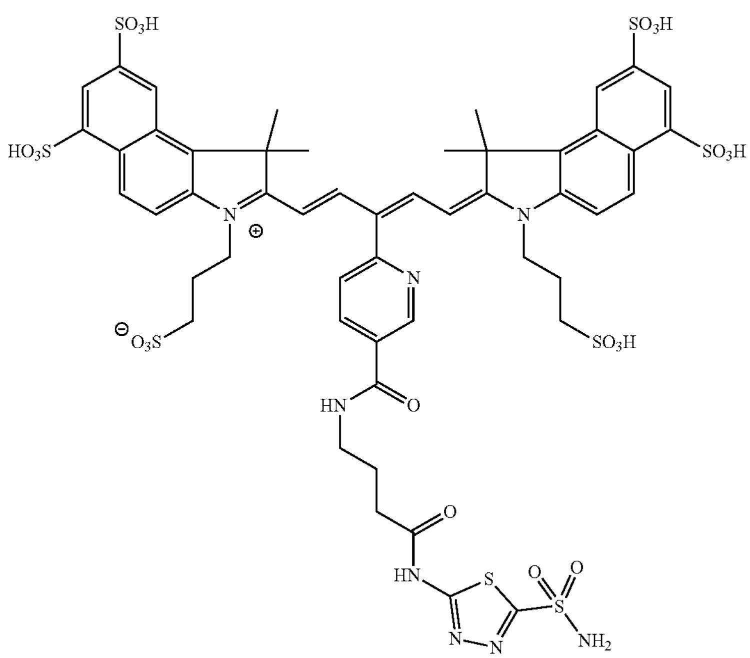 | 3-(2-((1E,3Z,5E)-5-(1,1-dimethyl-6,8-disulfo-3-(3-sulfopropyl)-1H-benzo[e]indol-2(3H)-ylidene)-3-(5-((4-oxo-4-((5-sulfamoyl-1,3,4-thiadiazol-2-yl)amino)butyl)carbamoyl)pyridin-2-yl)penta-1,3-dien-1-yl)-1,1-dimethyl-6,8-disulfo-1H-benzo[e]indol-3-ium-3-yl)propane-1-sulfonate |

TABLE 4-continued
| Compound No. | Structure | Name |
|---|---|---|
| IV-49 | 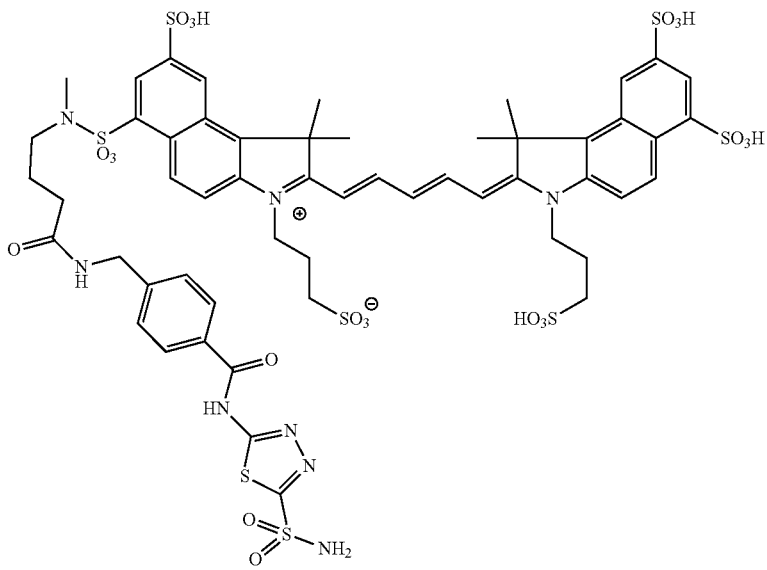 | 3-(2-((1E,3E,5E)-5-(1,1-dimethyl-6,8-disulfo-3-(3-sulfopropyl)-1H-benzo[e]indol-2(3H)-ylidene)penta-1,3-dien-1-yl)-1,1-dimethyl-6-(N-methyl-N-(4-oxo-4-((4-((5-sulfamoyl-1,3,4-thiadiazol-2-yl)carbamoyl)benzyl)amino)butyl)sulfamoyl)-1H-benzo[e]indol-3-ium-3-yl)propane-1-sulfonate |
| IV-50 | 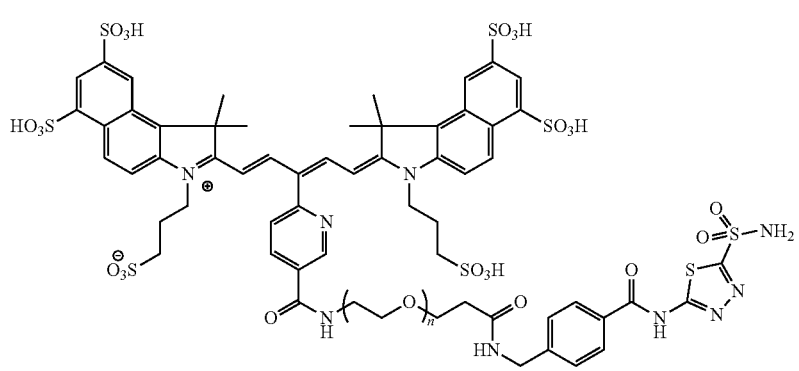 N = 3, 4, 8, 12, or 24 | N/A |

| Compound No. | Structure | Name |
|---|---|---|
| IV-51 | 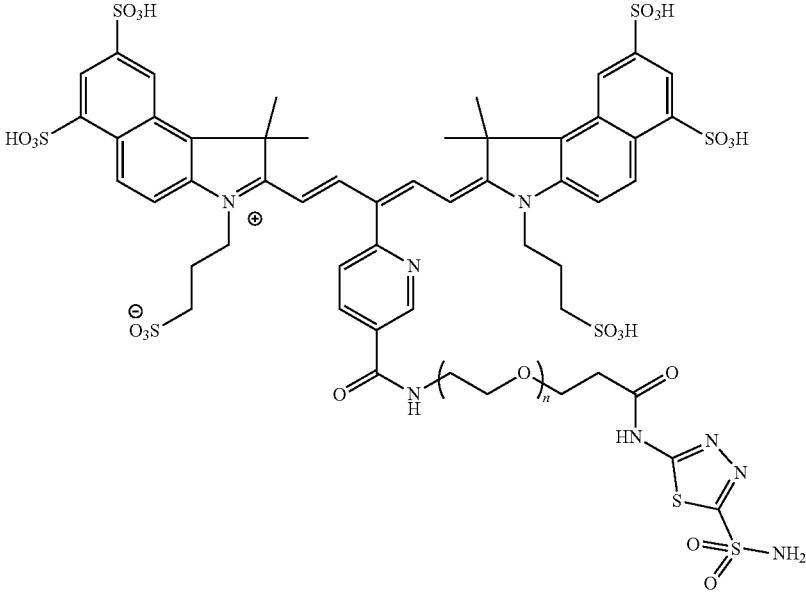 N = 3, 4, 8, 12, or 24 | N/A |
| IV-52 | 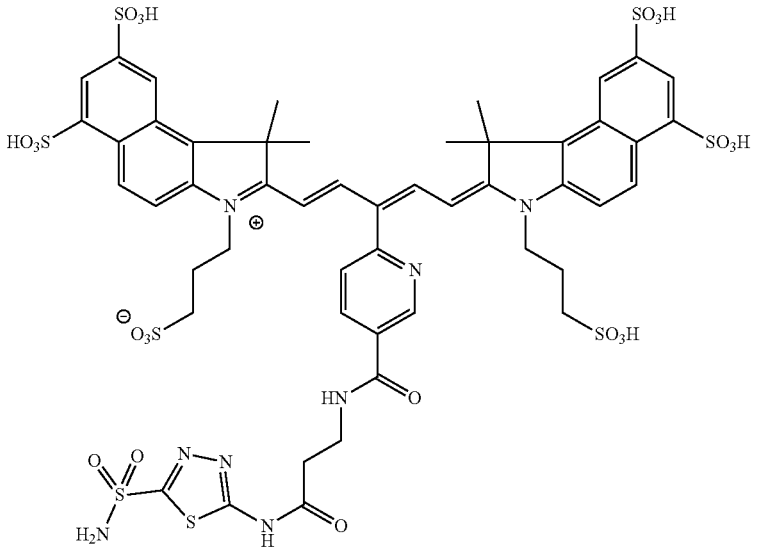 | 3-(2-((1E,3Z,5E)-5-(1,1-dimethyl-6,8-disulfo-3-(3-sulfopropyl)-1H-benzo[e]indol-2(3H)-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-1,1-dimethyl-6,8-disulfo-1H-benzo[e]indol-3-ium-3-yl)propane-1-sulfonate |

TABLE 4-continued

| Compound No. | Structure | Name |
|---|---|---|
| IV-53 | 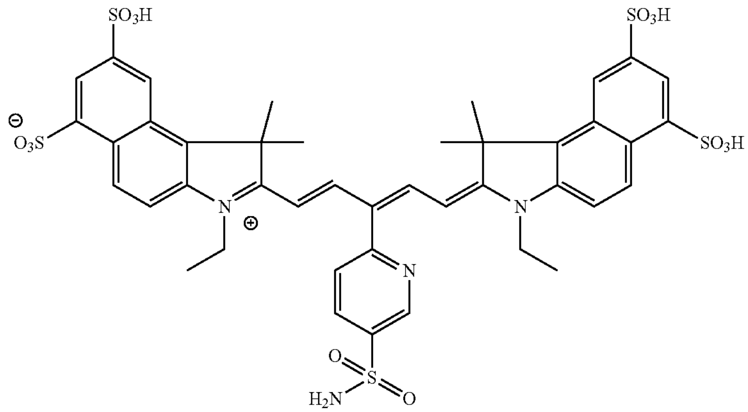 | 3-ethyl-2-((1E,3Z,5E)-5-(3-ethyl-1,1-dimethyl-6,8-disulfo-1H-benzo[e]indol-2(3H)-ylidene)-3-(5-sulfamoylpyridin-2-yl)penta-1,3-dien-1-yl)-1,1-dimethyl-8-sulfo-1H-benzo[e]indol-3-ium-6-sulfonate |
| IV-54 | 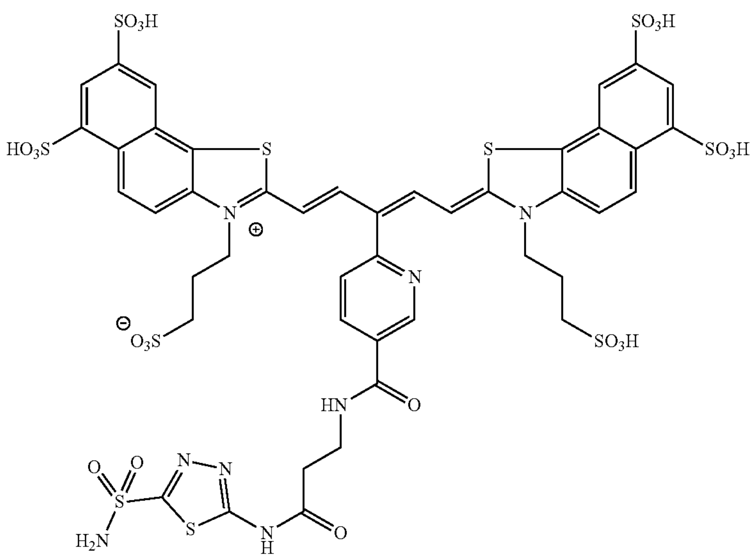 | 3-(2-((1E,3Z,5Z)-5-(6,8-disulfo-3-(3-sulfopropyl)naphtho[2,1-d]thiazol-2(3H)-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-6,8-disulfonaphtho[2,1-d]thiazol-3-ium-3-yl)propane-1-sulfonate |
| IV-55 | 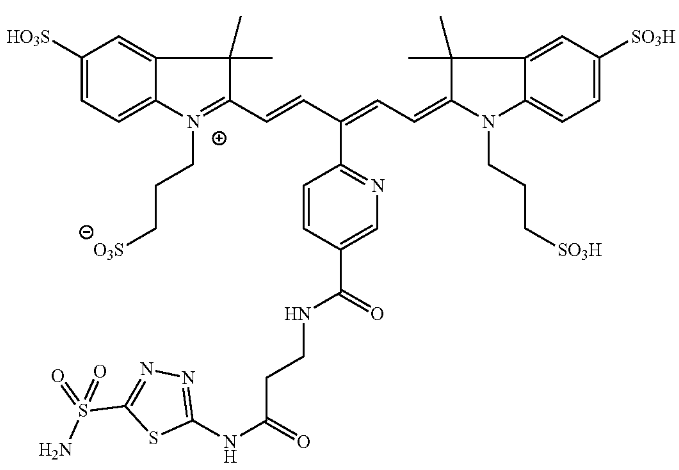 | 3-(2-((1E,3Z,5E)-5-(3,3-dimethyl-5-sulfo-1-(3-sulfopropyl)indolin-2-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-3,3-dimethyl-5-sulfo-3H-indol-1-ium-1-yl)propane-1-sulfonate |

TABLE 4-continued
| Compound No. | Structure | Name |
|---|---|---|
| IV-56 | 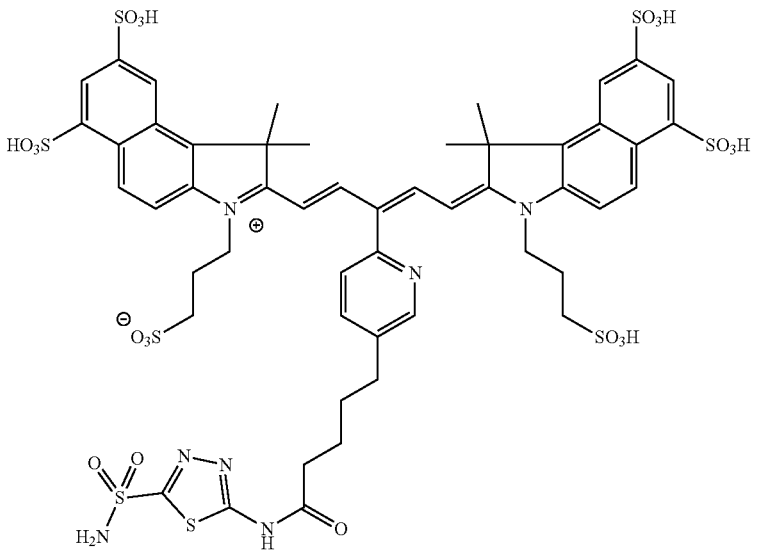 | 3-(2-((1E,3Z,5E)-5-(1,1-dimethyl-6,8-disulfo-3-(3-sulfopropyl)-1H-benzo[e]indol-2(3H)-ylidene)-3-(5-(5-oxo-5-((5-sulfamoyl-1,3,4-thiadiazol-2-yl)amino)pentyl)pyridin-2-yl)penta-1,3-dien-1-yl)-1,1-dimethyl-6,8-disulfo-1H-benzo[e]indol-3-ium-3-yl)propane-1-sulfonate |
| IV-57 | 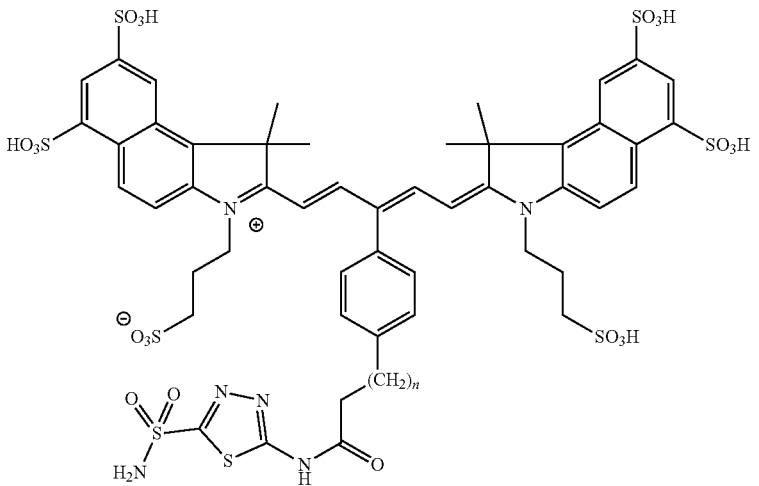<br>n = 0-6 | N/A |
| IV-58 | 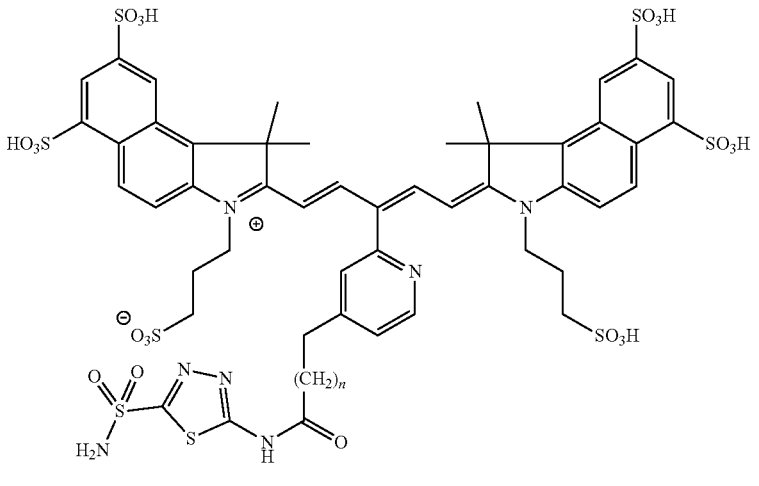<br>n = 0-6 | N/A |

TABLE 4-continued

| Compound No. | Structure | Name |
|---|---|---|
| IV-59 | 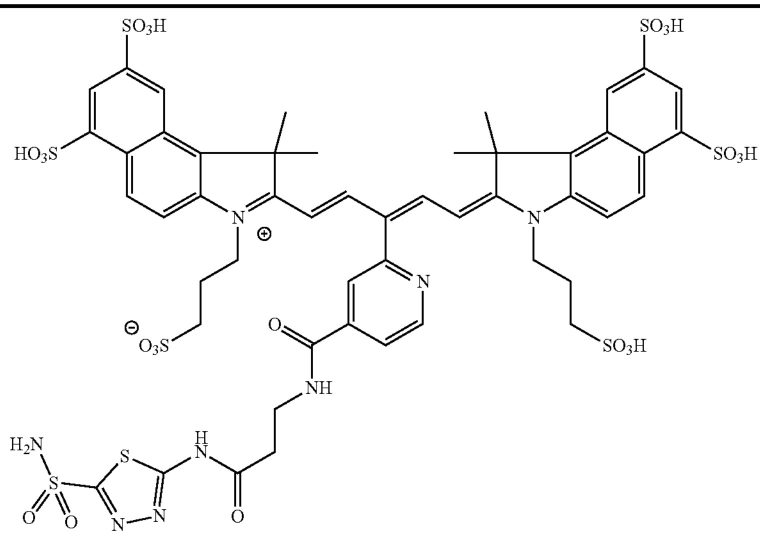 | 3-(2-((1E,3Z,5E)-5-(1,1-dimethyl-6,8-disulfo-3-(3-sulfopropyl)-1H-benzo[e]indol-2(3H)-ylidene)-3-(4-((3-oxo-3-((5-sulfamoyl-1,3,4-thiadiazol-2-yl)amino)propyl)carbamoyl)pyridin-2-yl)penta-1,3-dien-1-yl)-1,1-dimethyl-6,8-disulfo-1H-benzo[e]indol-3-ium-3-yl)propane-1-sulfonate |
| IV-60 | 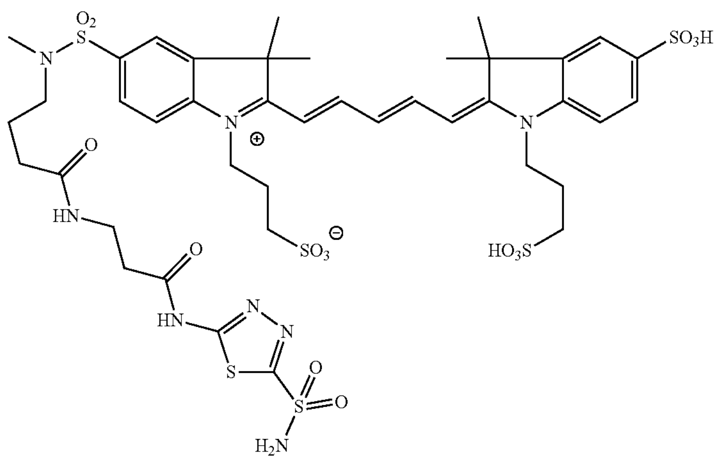 | 3-(2-((1E,3E,5E)-5-(3,3-dimethyl-5-sulfo-1-(3-sulfopropyl)indolin-2-ylidene)penta-1,3-dien-1-yl)-3,3-dimethyl-5-(N-methyl-N-(4-oxo-4-((3-oxo-3-((5-sulfamoyl-1,3,4-thiadiazol-2-yl)amino)propyl)amino)butyl)sulfamoyl)-3H-indol-1-ium-1-yl)propane-1-sulfonate |

The symbol "N/A" indicates that a chemical name was not available.

The imaging agents disclosed herein can be formulated into a pharmaceutical composition suitable for administration to a subject, for example, an animal and/or a human. The pharmaceutical composition can include one or more imaging agents and one or more excipients, for example, a stabilizer in a physiologically relevant carrier.

For in vivo use, the compositions of the present invention can be provided in a formulation suitable for administration to a subject, for example, an animal or a human. Accordingly, the formulations include the agents together with a physiologically relevant carrier suitable for the desired form and/or dose of administration. The term, "physiologically relevant carrier" is understood to mean a carrier in which the agents are dispersed, dissolved, suspended, admixed and physiologically tolerable, i.e., can be administered to, in, or on the subject's body without undue discomfort, or irritation, or toxicity. The preferred carrier is a fluid, preferably a liquid, more preferably an aqueous solution; however, carriers for solid formulations, topical formulations, inhaled formulations, ophthalmic formulations, and transdermal formulations are also contemplated as within the scope of the invention.

It is contemplated that the agents can be administered orally or parenterally. For parenteral administration, the agents can be administered intravenously, intramuscularly, cutaneously, percutaneously, subcutaneously, rectally, nasally, vaginally, and ocularly. Thus, the composition may be in the form of, e.g., solid tablets, capsules, pills, powders including lyophilized powders, colloidal suspensions, microspheres, liposomes granulates, suspensions, emulsions, solutions, gels, including hydrogels, pastes, ointments, creams, plasters, irrigation solutions, drenches, osmotic delivery devices, suppositories, enemas, injectables, implants, sprays, or aerosols. The pharmaceutical compositions can be formulated according to conventional pharmaceutical practice (see, e.g., Remington: The Science and Practice of Pharmacy, 20th edition, 2000, ed. A. R. Germaro, Lippincott Williams & Wilkins, Philadelphia, and Encyclopedia of Pharmaceutical Technology, eds. J. Swarbrick and J. C. Boylan, 1988-1999, Marcel Dekker, New York).

It is understood that the formulation of the agents, the choice of mode of administration, the dosages of agents administered to the subject, and the timing between administration of the agents and imaging is within the level of skill in the art.

Applications

It is understood that carbonic anhydrase targeting agents can be used in a variety of imaging and therapeutic applications.

(a) Imaging Methods

The present invention provides methods for in vitro and in vivo imaging using the imaging agents disclosed herein. For a review of optical imaging techniques, see, e.g., Alfano et al., Ann. NY Acad. Sci. 820:248-270 (1997); Weissleder, Nature Biotechnology 19, 316-317 (2001); Ntziachristos et al., Eur. Radiol. 13:195-208 (2003); Graves et al., Curr. Mol. Med. 4:419-430 (2004); Citrin et al., Expert Rev. Anticancer Ther. 4:857-864 (2004); Ntziachristos, Ann. Rev. Biomed. Eng. 8:1-33 (2006); Koo et al., Cell Oncol. 28:127-139 (2006); and Rao et al., Curr. Opin. Biotechnol. 18:17-25 (2007).

Optical imaging includes all methods from direct visualization without use of any device and use of devices such as various scopes, catheters and optical imaging equipment, for example computer based hardware for tomographic presentations. The imaging agents are useful with optical imaging modalities and measurement techniques including, but not limited to: endoscopy; fluorescence endoscopy; luminescence imaging; time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

An imaging system useful in the practice of the invention typically includes three basic components: (1) an appropriate light source for inducing excitation of the imaging agent, (2) a system for separating or distinguishing emissions from light used for fluorophore excitation, and (3) a detection system. The detection system can be hand-held or incorporated into other useful imaging devices, such as intraoperative microscopes. Exemplary detection systems include an endoscope, catheter, tomographic system, hand-held imaging system, or an intraoperative microscope.

Preferably, the light source provides monochromatic (or substantially monochromatic) light. The light source can be a suitably filtered white light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al., Proc. Natl. Acad. Sci. USA 91:4887-4891, 1994; Ntziachristos et al., Proc. Natl. Acad. Sci. USA 97:2767-2772, 2000; and Alexander, J. Clin. Laser Med. Surg. 9:416-418, 1991. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light/signal detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et al., J. Photochem. Photobiol. B 52:131-135, 1999), ovarian cancer (Major et al., Gynecol. Oncol. 66:122-132, 1997), colon and rectum (Mycek et al., Gastrointest. Endosc. 48:390-394, 1998; and Stepp et al., Endoscopy 30:379-386, 1998), bile ducts (Izuishi et al., Hepatogastroenterology 46:804-807, 1999), stomach (Abe et al., Endoscopy 32:281-286, 2000), bladder (Kriegmair et al., Urol. Int. 63:27-31, 1999; and Riedl et al., J. Endourol. 13:755-759, 1999), lung (Hirsch et al., Clin Cancer Res 7:5-220, 2001), brain (Ward, J. Laser Appl. 10:224-228, 1998), esophagus, and head and neck regions can be employed in the practice of the present invention.

Other types of light gathering components are catheter-based devices, including fiber optics devices. Such devices are particularly suitable for intravascular imaging. See, e.g., Tearney et al., Science 276:2037-2039, 1997; and Circulation 94:3013, 1996.

Still other imaging technologies, including phased array technology (Boas et al., Proc. Natl. Acad. Sci. USA 91:4887-4891, 1994; Chance, Ann. NY Acad. Sci. 838:29-45, 1998), optical tomography (Cheng et al., Optics Express 3:118-123, 1998; and Siegel et al., Optics Express 4:287-298, 1999), intravital microscopy (Dellian et al., Br. J. Cancer 82:1513-1518, 2000; Monsky et al., Cancer Res. 59:4129-4135, 1999; and Fukumura et al., Cell 94:715-725, 1998), confocal imaging (Korlach et al., Proc. Natl. Acad. Sci. USA 96:8461-8466, 1999; Rajadhyaksha et al., J. Invest. Dermatol. 104: 946-952, 1995; and Gonzalez et al., J. Med. 30:337-356, 1999) and fluorescence molecular tomography (FMT) (Nziachristos et al., Nature Medicine 8:757-760, 2002; U.S. Pat. No. 6,615,063, PCT WO 03/102558, and PCT WO 03/079015) can be used with the imaging agents of the invention. Similarly, the imaging agents can be used in a variety of imaging systems, for example, (1) the IVIS® Imaging Systems: 100 Series, 200 Series (Xenogen, Alameda, Calif.), (2) SPECTRUM and LUMINA (Xenogen, Alameda, Calif.), (3) the SoftScan® or the eXplore Optix™ (GE Healthcare, United Kingdom), (4) Maestro™ and Nuance™-2 Systems (CRi, Woburn, Mass.), (5) Image Station In-Vivo FX from Carestream Molecular Imaging, Rochester, N.Y. (formerly Kodak Molecular Imaging Systems), (6) OV100, IV100 (Olympus Corporation, Japan), (7) Cellvizio Mauna Kea Technologies, France), (8)] Nano-SPECT/CT or HiSPECT (Bioscan, Washington, D.C.), (9) CTLM® or LILA™ (Imaging Diagnostic Systems, Plantation, Fla.), (10) DYNOT™ (NIRx Medical Technologies, Glen Head, N.Y.), and (11) NightOWL Imaging Systems by Berthold Technologies, Germany.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

For agents that have magnetic properties, MRI imaging well known in the art can also be applied in the practice of the invention. For a review of MRI techniques see Westbrook, Handbook of MRI Technique, 2$^{nd}$ Edition, 1999, Blackwell Science. It is possible that images obtained, for example, by optical imaging and by magnetic resonance imaging can be co-registered or fused with one another to provide additional information about the item being imaged. Furthermore, multi-modality imaging systems (i.e., combined optical and MR imaging systems) can be used to create combined optical MR images.

In addition, the compositions and methods of the present invention can be used for other imaging compositions and methods. For example, the agents of the present invention can be imaged by other imaging modalities, such as, X-ray, computed tomography (CT), MR imaging, ultrasound, positron emission tomography (PET), and single photon computerized tomography (SPECT).

In addition, the compositions and methods of the present invention can be used in combination with other imaging compositions and methods. For example, the agents of the present invention can be imaged by optical imaging protocols either alone or in combination with other traditional imaging modalities, such as, X-ray, computed tomography (CT), MR imaging, ultrasound, positron emission tomography (PET), and single photon computerized tomography (SPECT). For instance, the compositions and methods of the present invention can be used in combination with CT or MRI to obtain both anatomical and molecular information simultaneously, for example, by co-registration of with an image generated by another imaging modality. The compositions and methods of the present invention can also be used in combination with X-ray, CT, PET, ultrasound, SPECT and other optical and MR contrast agents or alternatively, the agents of the present invention may also include imaging agents, such as iodine, gadolinium atoms and radioactive isotopes, which can be detected using CT, PET, SPECT, and MR imaging modalities in combination with optical imaging. The imaging agents can be linked to or incorporated in the agents.

(i) In Vivo Imaging Methods

With respect to optical in vivo imaging, such a method comprises (a) administering to a subject one or more of the carbonic anhydrase targeting agents described herein, (b) allowing sufficient time to permit the agent to distribute with the subject, and (c) detecting a signal emitted by the carbonic anhydrase targeting agent. The signal emitted by the agent can be used to construct an image, for example, a tomographic image. The foregoing steps can be repeated at predetermined time intervals thereby to permit evaluation of the emitted signals of the carbonic anhydrase targeting agents in the subject over time.

In another in vivo imaging method, the method comprises (a) administering to a subject one or more of the carbonic anhydrase targeting agents described herein that contains a fluorochrome; (b) allowing sufficient time to permit the carbonic anhydrase targeting agent to distribute within the subject; (c) exposing the subject to light of a wavelength absorbable by the fluorochrome, and (d) detecting a signal emitted by the carbonic anhydrase targeting agent. The foregoing steps can be repeated at predetermined time intervals thereby to permit evaluation of the emitted signals of the carbonic anhydrase targeting agents in the subject over time. The illuminating and/or detecting steps (steps (c) and (d), respectively) can be performed using an endoscope, catheter, tomographic system, planar system, hand-held imaging system, goggles, or an intraoperative microscope.

Before or during these steps, a detection system can be positioned around or in the vicinity of a subject (for example, an animal or a human) to detect signals emitted from the subject. The emitted signals can be processed to construct an image, for example, a tomographic image. In addition, the processed signals can be displayed as images either alone or as fused (combined) images.

In addition, it is possible to practice an in vivo imaging method that selectively detects and images one, two or more molecular imaging probes, including the carbonic anhydrase targeting agents simultaneously. In such an approach, for example, in step (a) noted above, two or more imaging probes whose signal properties are distinguishable from one another are administered to the subject, either at the same time or sequentially, wherein at least one of the molecular imaging probes is a carbonic anhydrase agent. The use of multiple probes permits the recording of multiple biological processes, functions or targets.

The subject may be a vertebrate, for example, a mammal, for example, a human. The subject may also be a non-vertebrate (for example, *C. elegans, drosophila*, or another model research organism, etc.) used in laboratory research.

Information provided by such in vivo imaging approaches, for example, the presence, absence, or level of emitted signal can be used to detect and/or monitor a disease in the subject. Exemplary diseases include, without limitation, autoimmune disease, bone disease, cancer, cardiovascular disease, environmental disease, dermatological disease, immunologic disease, inherited disease, infectious disease, metabolic disease, neurodegenerative disease, ophthalmic disease, and respiratory disease. In addition, in vivo imaging can be used to assess the effect of a compound or therapy by using the imaging agents, wherein the subject is imaged prior to and after treatment with the compound or therapy, and the corresponding signal/images are compared.

The carbonic anhydrase targeting agents also can be used in in vivo imaging method where cells labeled with the carbonic anhydrase targeting agent are administered to the recipient. The cells can be labeled with the carbonic anhydrase targeting agents either in vivo or ex vivo. In the ex vivo approach, cells can be derived directly from a subject or from another source (e.g., from another subject, cell culture, etc.). The carbonic anhydrase targeting agents can be mixed with the cells to effectively label the cells and the resulting labeled cells administered to the subject into a subject in step (a). Steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

It is understood that the formulation of the carbonic anhydrase targeting agents, the choice of mode of administration, the dosages of carbonic anhydrase targeting agents administered to the subject, and the timing between administration of the carbonic anhydrase targeting agents and imaging is within the level of skill in the art.

The foregoing methods can be used to determine a number of indicia, including tracking the localization of the carbonic anhydrase targeting agent in the subject over time or assessing changes or alterations in the metabolism and/or excretion of the carbonic anhydrase targeting agent in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The methods and compositions of the invention can be used to help a physician or surgeon to identify and characterize areas of disease, such as cancers and specifically hypoxic tumors, or other hypoxic tissues, to distinguish diseased and/or hypoxic tissues from normal tissues, such as detecting specific regions of hypoxia within a tumor or other tissues that are difficult to detect using ordinary imaging techniques, and to further assess said tissues as candidates for particular treatment regimens, or gauge the prognosis such as likelihood of metastasis.

The methods and compositions of the invention can also be used in the detection, characterization and/or determination of the localization of a disease, including early disease, the severity of a disease or a disease-associated condition, the staging of a disease, and/or monitoring a disease. The presence, absence, or level of an emitted signal can be indicative of a disease state.

The methods and compositions of the invention can also be used to monitor and/or guide various therapeutic interventions, such as surgical procedures, and monitoring drug therapy, including cell based therapies. The methods described herein can also be used to assess therapeutic efficacy of various treatment regimens, including but not limited to those designed to reduce tumor acidosis and metastasis or various radiotherapeutics. The methods of the invention can also be used in prognosis of a disease or disease condition.

With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, and bone), cardiovascular disease (for example, atherosclerosis and inflammatory conditions of blood vessels, ischemia, stroke, thrombosis, and disseminated intravascular coagulation), dermatologic disease (for example, Kaposi's Sarcoma, psoriasis, and allergic dermatitis), ophthalmic disease (for example, macular degeneration, and diabetic retinopathy), infectious disease (for example, bacterial, viral, fungal and parasitic infections, including Acquired Immunodeficiency Syndrome, Malaria, Chagas Disease, and Schistosomiasis), immunologic disease (for example, an autoimmune disorder, lymphoma, multiple sclerosis, rheumatoid arthritis, diabetes mellitus, lupus erythematosis, myasthenia gravis, and Graves disease), central nervous system disease (for example, a neurodegenerative disease, such as Parkinson's disease or Alzheimer's disease, Huntington's Disease, amyotrophic lateral sclerosis, and prion disease), inherited diseases, metabolic diseases, environmental diseases (for example, lead, mercury and radioactive poisoning, and skin cancer), bone-related disease (for example, osteoporosis, primary and metastatic bone tumors, and osteoarthritis), neurodegenerative disease, and surgery-related complications (such as graft rejection, organ rejection, alterations in wound healing, fibrosis or other complications related to surgical implants).

The methods and compositions described herein can, therefore, be used, for example, to detect and/or quantify the presence and/or localization of carbonic anhydrase in a subject, including humans, for instance in tumor cells, and to detect and/or quantify the presence and/or localization of hypoxic tissue, including the presence of hypoxic regions within a tumor. The methods and compositions described herein can also be used to detect and/or quantify carbonic anhydrase IX associated with diseases, disorders and conditions, including but not limited to preneoplastic/neoplastic disease including areas at risk for acute occlusion (i.e., vulnerable plaques) in coronary and peripheral arteries, regions of expanding aneurysms, unstable plaque in carotid arteries, and ischemic areas. The methods and compositions of the invention can also be used in identification and evaluation of cell death, injury, apoptosis, necrosis, and hypoxia. The methods and compositions can also be used for drug delivery and to monitor drug delivery, especially when drugs or drug-like molecules are chemically attached to the fluorescent probes. Exemplary drug molecules include chemotherapeutic and cytostatic agents and photodynamic agents including but not limited to Photofrin, Lutrin, Antrin, aminolevulinic acid, hypericin, benzoporphyrin derivative, and porphyrins.

In addition, the methods and compositions described herein can be used to image hypoxia (oxygen deficiency) in a subject. The method comprises administering to a subject (for example, a human or animal) an amount of one or more of the carbonic targeting agents described herein sufficient to facilitate hypoxia imaging. After sufficient time to permit the agent to distribute within the animal or distribute within the area to be imaged, the presence and/or amount of the agent is determined. The presence and/or amount of the agent can then be used to create an image, for example, a tomographic image, representative of oxygen depletion within the tissues of the subject.

(ii) In Vitro Imaging Methods

With respect to in vitro imaging, the imaging agents can be used in a variety of in vitro assays. For example, an exemplary in vitro imaging method comprises: (a) contacting a sample, for example, a biological sample, with one or more of the carbonic anhydrase targeting agents described herein; (b) allowing the agent(s) to interact with a biological target in the sample; (c) optionally, removing unbound agent; and (d) detecting a signal emitted from the agent thereby to determine whether the agent has been activated by or bound to the biological target. When the carbonic anhydrase targeting agent comprises a fluorochrome, step (d) further comprises illuminating the sample with light of a wavelength absorbable by the fluorochrome to produce the emitted signal.

After an agent has been designed, synthesized, and optionally formulated, it can be tested in vitro by one skilled in the art to assess its biological and performance characteristics. For instance, different types of cells grown in culture can be used to assess the biological and performance characteristics of the agent. Cellular uptake, binding or cellular localization of the agent can be assessed using techniques known in the art, including, for example, fluorescent microscopy, FACS analysis, immunohistochemistry, immunoprecipitation, in situ hybridization and Forster resonance energy transfer (FRET) or fluorescence resonance energy transfer. By way of example, the agents can be contacted with a sample for a period of time and then washed to remove any free agents. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the agents. Other detection methods including, but not limited to flow cytometry, immunoassays, hybridization assays, and microarray analysis can also be used.

(b) Therapeutic Applications

Certain of the carbonic anhydrase targeting agents described herein, for example, agents containing a radiolabel and drug molecule, can be used to ameliorate a symptom of, or treat, a particular disease or disorder. The method comprises (a) administering an amount of one or more the agents described herein sufficient to impart a therapeutic effect in the subject; and (b) permitting sufficient time for the agent to distribute within the subject or otherwise localize in a region of the subject to be treated and then, (c) depending on the therapeutic agent, optionally activating the agent to impart a therapeutic effect. For example, when the therapeutic agent is a radiolabel, no subsequent activation is required. However, when the therapeutic agent is a photoreactive agent, for example, a dye used in photodynamic therapy, the agent may be activated by exposing the agent to light having a wavelength that activates the agent. As a result, the agents can be used to treat a condition of interest, for example, a cancer, immune disorder, inflammatory disorder, vascular disorder and the like. Furthermore the agents can be used to inhibit acidosis in a hypoxic tumor, or other region of interest in the subject, or reduce tumor cell proliferation from hypoxic regions.

The invention will now be illustrated by means of the following examples, which are given for the purpose of illustration only and without any intention to limit the scope of the present invention.

Examples

The compounds of the present invention can be synthesized from readily available starting materials following standard methods and procedures. The following non limiting examples demonstrate the synthesis of exemplary fluorescent carbonic anhydrase agents. Representative materials and methods that may be used in preparing the materials of the invention are described further below. Unless otherwise stated, all chemicals and solvents (reagent grade) are used as commercially obtained without further purification. Synthesized compounds are characterized by HPLC on a 2695 system using either a Phenomenex Phenyl-hexyl column (3μ, 100×4.6 mm) or C18 column (5μ, 250×4.6 mm) with a flow rate of 0.5 to 1.0 mL/min. A linear gradient of A (25 mM ammonium formate, +5% methanol) and B (acetonitrile) was used. Typically, the gradient started at 0-20% of B and changed to 25-90% of B over 10 to 20 min. Chromatograms were monitored using a 2998 photodiode array detector and ZQ2000 MS mass detector. Preparative HPLC was performed on a Varian system using a Phenomenex C18 column (250×21 mm) at 20 mL/min using similar gradient as the analytical run.

Example 1: Synthesis of exemplary compound 3-(2-((1E,3E,5E)-5-(1,1-dimethyl-6,8-disulfo-3-(3-sulfopropyl)-1H-benzo[e]indol-2(3H)-ylidene)penta-1,3-dien-1-yl)-1,1-dimethyl-6-(N-methyl-N-(4-oxo-4-((4-sulfamoylbenzyl)amino)butyl)sulfamoyl)-1H-benzo[e]indol-3-ium-3-yl)propane-1-sulfonate [B1]

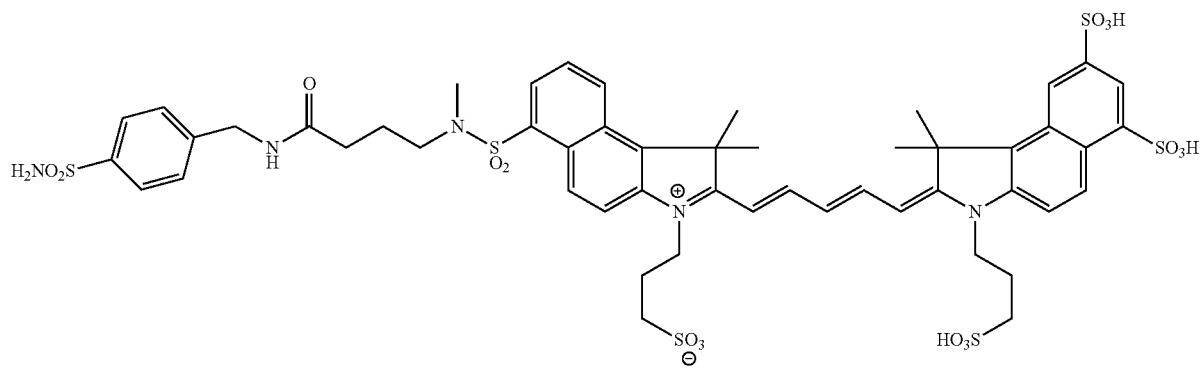

4-Aminomethylbenzenesulfonamide (2.7 mg, 12 μmol) and the succinimidyl ester of fluorochrome F1 (10 μmol) and 5.5 μL N-methylmorpholine (50 μmol) were combined in 130 μL of anhydrous DMF in a sealed vial and rotated at 25° C. for 1 hour. The crude product was precipitated by addition of 1.5 mL of ethyl acetate, centrifuged, decanted and dried under vacuum. The product was purified by HPLC and the mass confirmed by LCMS, calculated for [M+H]$^+$ 1206.2, found 1206.2.

Example 2: Synthesis of exemplary compound 3-ethyl-2-((1E,3Z,5E)-5-(3-ethyl-1,1-dimethyl-6,8-disulfo-1H-benzo[e]indol-2(3H)-ylidene)-3-(5-((4-sulfamoylbenzyl)carbamoyl)pyridin-2-yl)penta-1,3-dien-1-yl)-1,1-dimethyl-8-sulfo-1H-benzo[e]indol-3-ium-6-sulfonate [B6]

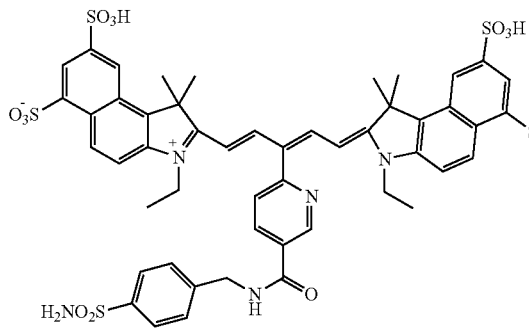

4-Aminomethylbenzenesulfonamide (3.2 mg, 14 µmol), the succinimidyl ester of fluorochrome F6 (12 µmol), 6.5 µL N-methylmorpholine (60 µmol), dimethylaminopropyl ethyl carbodiimide (2.0 mg, 10.5 µmol), and hydroxybenzotriazole (2.0 mg, 15 µmol) were combined in 150 µL of anhydrous DMF in a sealed vial and rotated at 25° C. for 3 hours. The crude product was precipitated by addition of 1.5 mL of ethyl acetate, centrifuged, decanted and dried under vacuum. The product was purified by HPLC and the mass confirmed by LCMS, calculated for [M+H]+, 1120.3, found 1120.3.

Example 3: Synthesis of exemplary compound 2-((1E,3Z,5E)-5-(1,1-dimethyl-6,8-disulfo-3-(3-sulfopropyl)-1H-benzo[e]indol-2(3H)-ylidene)-3-(5-((4-sulfamoylbenzyl)carbamoyl)pyridin-2-yl)penta-1,3-dien-1-yl)-1,1-dimethyl-8-sulfo-3-(3-sulfopropyl)-1H-benzo[e]indol-3-ium-6-sulfonate [B5]

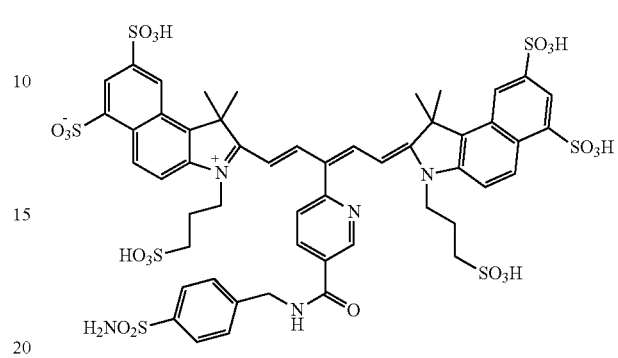

4-aminomethylbenzenesulfonamide (3.5 mg, 16 µmol), the succinimidyl ester of fluorochrome F5 (13 µmol) and 7.2 µL N-methylmorpholine (65 µmol), were combined in 110 µL of anhydrous DMF in a sealed vial and rotated at 25° C. for 1 hour. The crude product was precipitated by addition of 1.5 mL of ethyl acetate, centrifuged, decanted and dried under vacuum. The product was purified by HPLC and the mass confirmed by LCMS, calculated for [M+H]+ 1308.1, found 1308.3.

Example 4: Synthesis of exemplary compound 3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-((4-sulfamoylbenzyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate [B3]

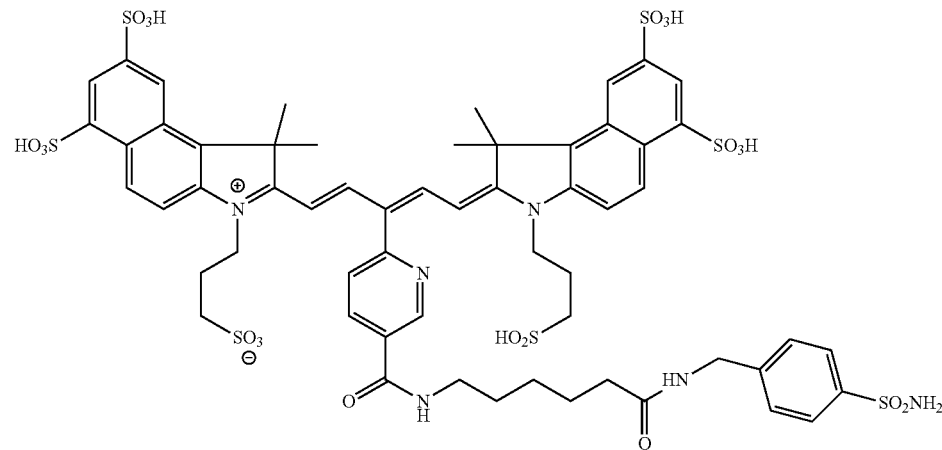

4-Aminomethylbenzenesulfonamide (3.0 mg, 13 µmol), the succinimidyl ester of fluorochrome F3 (11 µmol) and 6.2 µL N-methylmorpholine (55 µmol), were combined in 105 µL of anhydrous DMF in a sealed vial and rotated at 25° C. for 1 hour. The crude product was precipitated by addition of 1.5 mL of ethyl acetate, centrifuged, decanted and dried under vacuum. The product was purified by HPLC and the mass confirmed by LCMS, calculated for [M+2H]$^{2+}$711.1, found 711.5.

Example 5: Synthesis of exemplary compound 3-(2-((1E,3Z,5E)-5-(1,1-dimethyl-6,8-disulfo-3-(3-sulfopropyl)-1H-benzo[e]indol-2(3H)-ylidene)-3-(5-((3-oxo-1-(4-sulfamoylphenyl)-6,9,12,15,18,21,24,27,30,33,36,39,42,45,48,51,54,57,60,63,66,69,72,75-tetracosaoxa-2-azaheptaheptacontan-77-yl)carbamoyl)pyridin-2-yl)penta-1,3-dien-1-yl)-1,1-dimethyl-6,8-disulfo-1H-benzo[e]indol-3-ium-3-yl)propane-1-sulfonate [B12]

4-aminoethylbenzenesulfonamide (3.7 mg, 16 μmol), the succinimidyl ester of fluorochrome F5 (13 μmol) and 7.2 μL N-methylmorpholine (65 μmol), are combined in 110 μL of anhydrous DMF in a sealed vial and rotated at 25° C. for 1 hour. The crude product is precipitated by addition of 1.5 mL of ethyl acetate, centrifuged, decanted and dried under vacuum. The product is purified by HPLC and the mass confirmed by LCMS.

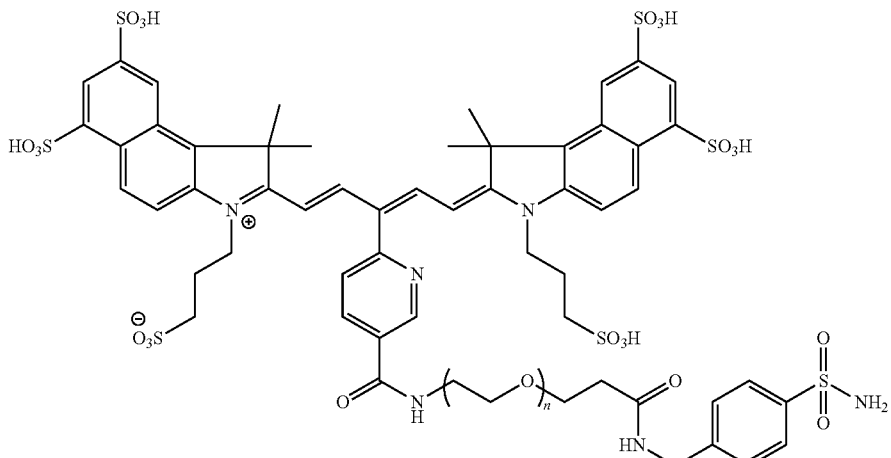

n = 24

4-Aminomethylbenzenesulfonamide (3.0 mg, 13 μmol), the succinimidyl ester of fluorochrome F12 (n=24) (11 μmol) and 6.2 μL N-methylmorpholine (55 μmol), were combined in 105 μL of anhydrous DMF in a sealed vial and rotated at 25° C. for 1 hour. The crude product was precipitated by addition of 1.5 mL of ethyl acetate, centrifuged, decanted and dried under vacuum. The product was purified by HPLC and the mass confirmed by LCMS, calculated for $[M+2H+3NH_3]^{2+}$ 1244.4, found 1244.5.

Example 6: Synthesis of exemplary compound 2-((1E,3Z,5E)-5-(1,1-dimethyl-6,8-disulfo-3-(3-sulfopropyl)-1H-benzo[e]indol-2(3H)-ylidene)-3-(5-((4-sulfamoylbenzyl)carbamoyl)pyridin-2-yl)penta-1,3-dien-1-yl)-1,1-dimethyl-8-sulfo-3-(3-sulfopropyl)-1H-benzo[e]indol-3-ium-6-sulfonate [C5]

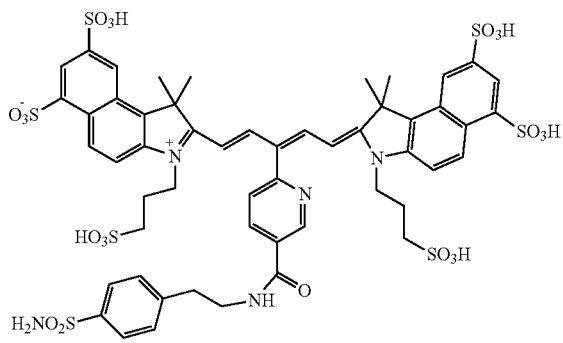

Example 7: Synthesis of Intermediate Compound 4-(aminomethyl)-N-(5-sulfamoyl-1,3,4-thiadiazol-2-yl)benzamide [A0]

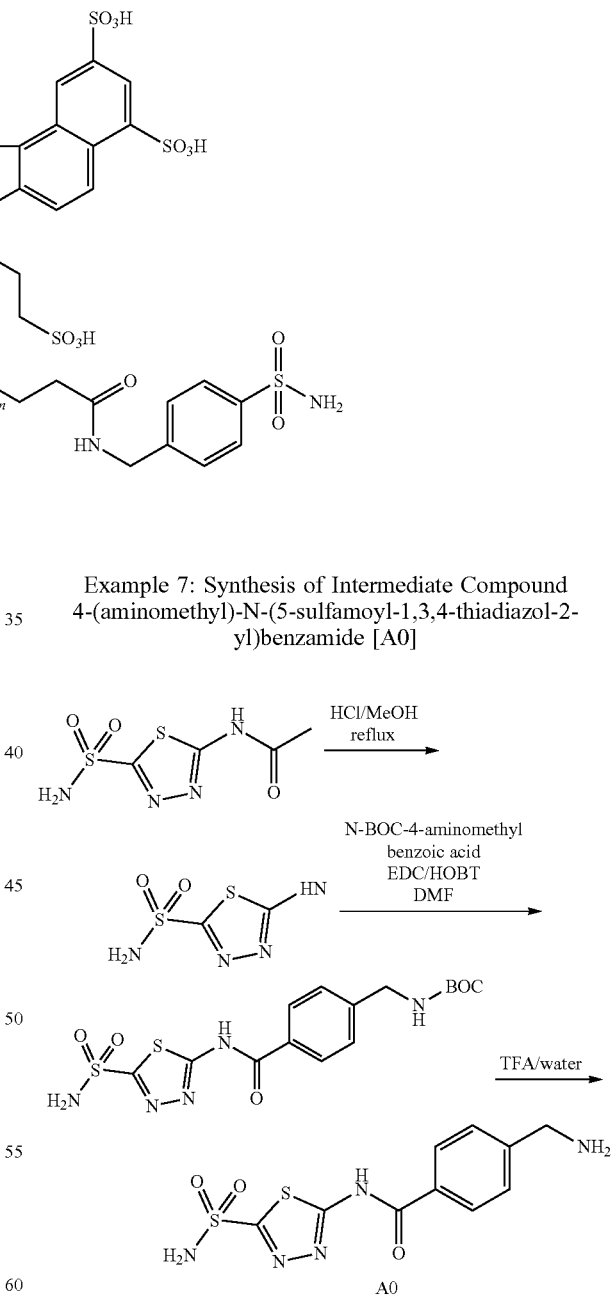

Part A: Acetazolamide (1 g, 4.5 μmol) was dissolved 10 mL of methanol and 1.5 mL of concentrated hydrochloric acid and refluxed for 4 h. The solution was cooled to 0° C. in and neutralized by addition of 0.5 mL of 1 M HEPES buffer, pH 7.0 followed by 1 M NaOH until a pH of 7. Methanol was removed under vacuum then cooled to 4° C.

and pure 5-amino-1,3,4-thiadiazole-2-sulfonamide was allowed to crystalize out of solution.

Part B: 5-Amino-1,3,4-thiadiazole-2-sulfonamide, (100 mg, 560 μmol) N-BOC-4-aminomethyl benzoic acid (140 mg, 560 μmol), dimethylaminopropyl ethyl carbodiimide (117 mg, 610 μmol) and hydroxybenzotriazole (84 mg, 610 μmol) were combined in 600 μL of anhydrous DMF in a sealed reaction tube and rotated at room temperature for 48 h. The crude solution was diluted with 1 mL of water resulting in precipitation of the product followed by slow addition of 1 M NaOH until a pH of 8.5 was achieved (~1.5 mL) resulting in a clear solution. The solution was purified by prep HPLC and the purified product deprotected in 600 μL of 95% TFA/water for 15 minutes then dried under vacuum to yield 150 mg (85%) of 4-(aminomethyl)-N-(5-sulfamoyl-1,3,4-thiadiazol-2-yl)benzamide A0.

Example 8: Synthesis of exemplary compound 3-(2-((1E,3E,5E)-5-(1,1-dimethyl-6,8-disulfo-3-(3-sulfopropyl)-1H-benzo[e]indol-2(3H)-ylidene)penta-1,3-dien-1-yl)-1,1-dimethyl-6-(N-methyl-N-(4-oxo-4-((4-((5-sulfamoyl-1,3,4-thiadiazol-2-yl)carbamoyl)benzyl)amino)butyl)sulfamoyl)-1H-benzo[e]indol-3-ium-3-yl)propane-1-sulfonate [A1]

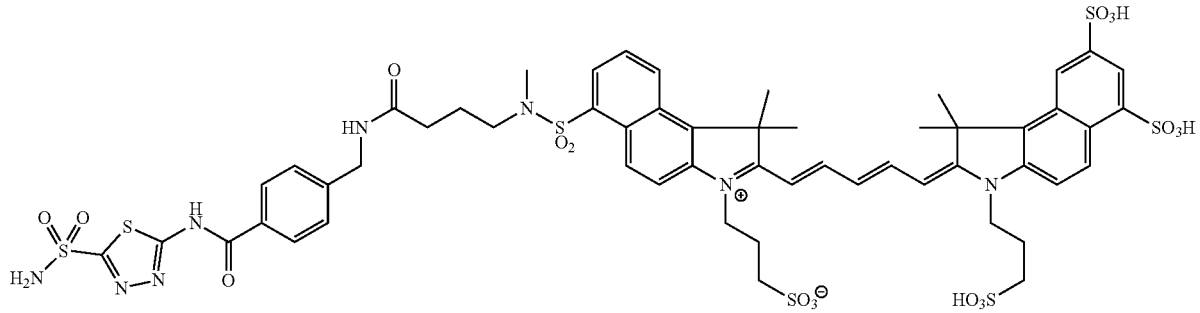

4-(Aminomethyl)-N-(5-sulfamoyl-1,3,4-thiadiazol-2-yl)benzamide (5 mg, 16 μmol), the succinimidyl ester of fluorochrome F1 (16 μmol) and N-methylmorpholine (10 μL) were combined in 100 μL of anhydrous DMF in a sealed vial and rotated at 37° C. for 1 h. The crude product was precipitated by addition of 1.5 mL of ethyl acetate, centrifuged, decanted and dried under vacuum. The product was purified by HPLC and the mass confirmed by LCMS, calculated for [M+H]+ 1333.2; found 1333.1.

Example 9: Synthesis of exemplary compound 3-(2-((1E,3Z,5E)-5-(1,1-dimethyl-6,8-disulfo-3-(3-sulfopropyl)-1H-benzo[e]indol-2(3H)-ylidene)-3-(5-((4-((5-sulfamoyl-1,3,4-thiadiazol-2-yl)carbamoyl)benzyl)carbamoyl)pyridin-2-yl)penta-1,3-dien-1-yl)-1,1-dimethyl-6,8-disulfo-1H-benzo[e]indol-3-ium-3-yl)propane-1-sulfonate [A5]

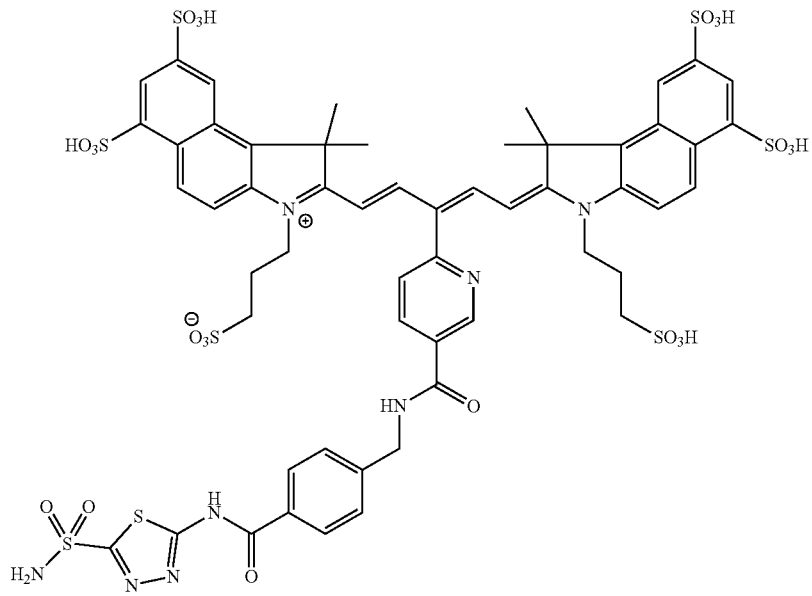

4-(Aminomethyl)-N-(5-sulfamoyl-1,3,4-thiadiazol-2-yl) benzamide (5 mg, 16 μmol), the succinimidyl ester of fluorochrome F5 (16 μmol) and N-methylmorpholine (10 μL) were combined in 100 μL of anhydrous DMF in a sealed vial and rotated at 37° C. for 1 h. The crude product was precipitated by addition of 1.5 mL of ethyl acetate, centrifuged, decanted and dried under vacuum. The product was purified by HPLC and the mass confirmed by LCMS, calculated for [M+H]+ 1435.1; found 1435.1.

Example 10: Synthesis of exemplary compound 3-ethyl-2-01E,3Z,5E)-5-(3-ethyl-1,1-dimethyl-6,8-disulfo-1H-benzo[e]indol-2(3H)-ylidene)-3-(5-((4-((5-sulfamoyl-1,3,4-thiadiazol-2-yl)carbamoyl)benzyl)carbamoyl)pyridin-2-yl)penta-1,3-dien-1-yl)-1,1-dimethyl-8-sulfo-1H-benzo[e]indol-3-ium-6-sulfonate [A6]

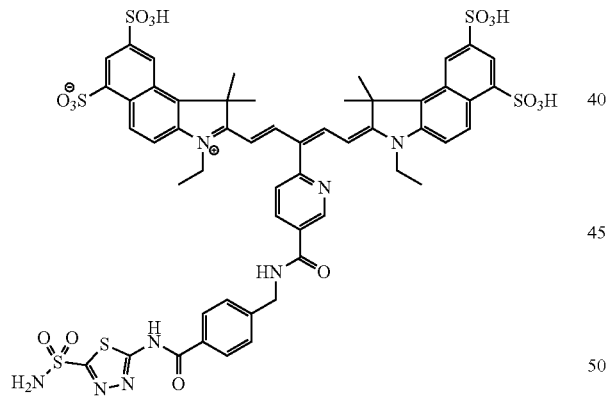

4-(Aminomethyl)-N-(5-sulfamoyl-1,3,4-thiadiazol-2-yl) benzamide (5 mg, 16 μmol), the succinimidyl ester of fluorochrome F6 (16 μmol) and N-methylmorpholine (10 μL) were combined in 100 μL of anhydrous DMF in a sealed vial and rotated at 37° C. for 1 h. The crude product was precipitated by addition of 1.5 mL of ethyl acetate, centrifuged, decanted and dried under vacuum. The product was purified by HPLC and the mass confirmed by LCMS, calculated for [M+H]+ 1247.2; found 1247.3.

Example 11: Synthesis of exemplary compound 3-(2-((1E,3Z,5E)-5-(1,1-dimethyl-6,8-disulfo-3-(3-sulfopropyl)-1H-benzo[e]indol-2(3H)-ylidene)-3-(5-((6-oxo-6-((4-((5-sulfamoyl-1,3,4-thiadiazol-2-yl)carbamoyl)benzyl)amino)hexyl)carbamoyl)pyridin-2-yl)penta-1,3-dien-1-yl)-1,1-dimethyl-6,8-disulfo-1H-benzo[e]indol-3-ium-3-yl)propane-1-sulfonate [A3]

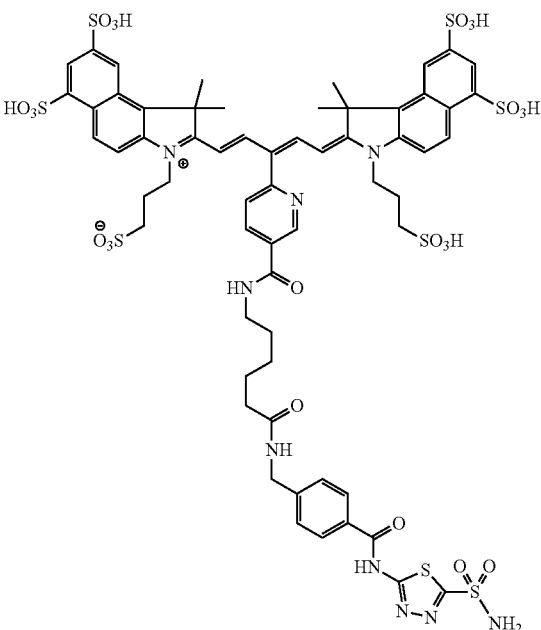

4-(Aminomethyl)-N-(5-sulfamoyl-1,3,4-thiadiazol-2-yl) benzamide (5 mg, 16 μmol), the succinimidyl ester of fluorochrome F3 (16 μmol) and N-methylmorpholine (10 μL) were combined in 100 μL of anhydrous DMF in a sealed vial and rotated at 37° C. for 1 h. The crude product was precipitated by addition of 1.5 mL of ethyl acetate, centrifuged, decanted and dried under vacuum. The product was purified by HPLC and the mass confirmed by LCMS, calculated for [M+2H]$^2$+774.6; found 775.0.

Example 12: Synthesis of exemplary compound 3-(2-(((1E,3Z,5E)-5-(1,1-dimethyl-6,8-disulfo-3-(3-sulfopropyl)-1H-benzo[e]indol-2(3H)-ylidene)-3-(5-((3-oxo-1-(4-((5-sulfamoyl-1,3,4-thiadiazol-2-yl)carbamoyl)phenyl)-6,9,12,15,18,21,24,27,30,33,36,39,42,45,48,51,54,57,60,63,66,69,72,75-tetracosaoxa-2-azaheptaheptacontan-77-yl)carbamoyl)pyridin-2-yl)penta-1,3-dien-1-yl)-1,1-dimethyl-6,8-disulfo-1H-benzo[e]indol-3-ium-3-yl)propane-1-sulfonate [A12]

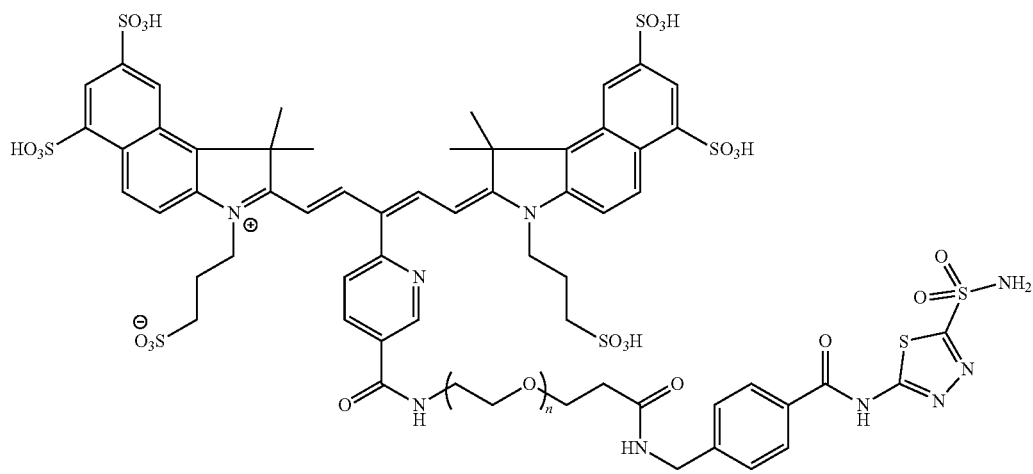

n = 24

4-(Aminomethyl)-N-(5-sulfamoyl-1,3,4-thiadiazol-2-yl)benzamide (5 mg, 16 μmol), the succinimidyl ester of fluorochrome F12 (n=24) (16 μmol) and N-methylmorpholine (10 μL) were combined in 100 μL of anhydrous DMF in a sealed vial and rotated at 37° C. for 1 h. The crude product was precipitated by addition of 1.5 mL of ethyl acetate, centrifuged, decanted and dried under vacuum. The product was purified by HPLC and the mass confirmed by LCMS, $[M+3H]^{3+}$ calculated 854.9, found 855.4.

Example 13: Synthesis of Intermediate Compound 3-amino-N-(5-sulfamoyl-1,3,4-thiadiazol-2-yl)propanamide [C0]

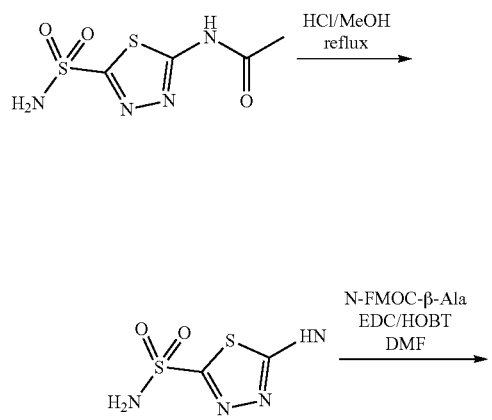

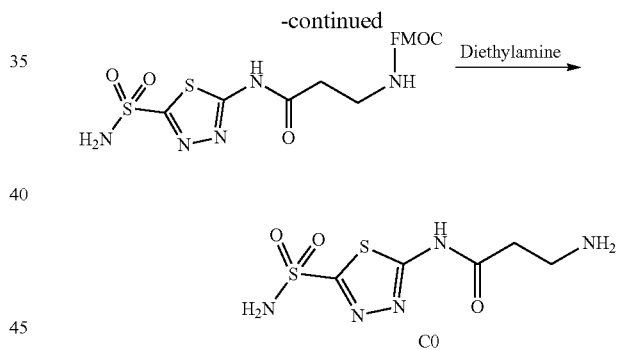

Part A: Acetazolamide (1 g, 4.5 μmol) was dissolved 10 mL of methanol and 1.5 mL of concentrated hydrochloric acid and refluxed for 4 h. The solution was cooled to 0° C. in and neutralized by addition of 0.5 mL of 1 M HEPES buffer, pH 7.0 followed by 1 M NaOH until a pH of 7. Methanol was removed under vacuum then cooled to 4° C. and pure 5-amino-1,3,4-thiadiazole-2-sulfonamide was allowed to crystallize out of solution.

Part B: 5-amino-1,3,4-thiadiazole-2-sulfonamide (20 mg, 110 μmol) N-FMOC β-alanine (31 mg, 100 μmol), dimethylaminopropyl ethyl carbodiimide (EDC) (21 mg, 110 μmol) and hydroxybenzotriazole (HOBT) (15 mg, 110 μmol) were combined in 200 μL of anhydrous DMF in a sealed reaction tube and rotated at room temperature for 48 h. The crude product was purified by prep HPLC, then deprotected by dissolving in 125 μL of 20% diethylamine in DMF for 10 min followed by precipitation with ether to give 3-amino-N-(5-sulfamoyl-1,3,4-thiadiazol-2-yl)propanamide as a white solid.

Example 14: Synthesis of Exemplary Compound 3-(2-(((1E,3Z,5E)-5-(1,1-dimethyl-6,8-disulfo-3-(3-sulfopropyl)-1H-benzo[e]indol-2(3H)-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-1,1-dimethyl-6,8-disulfo-1H-benzo[e]indol-3-ium-3-yl)propane-1-sulfonate [C5]

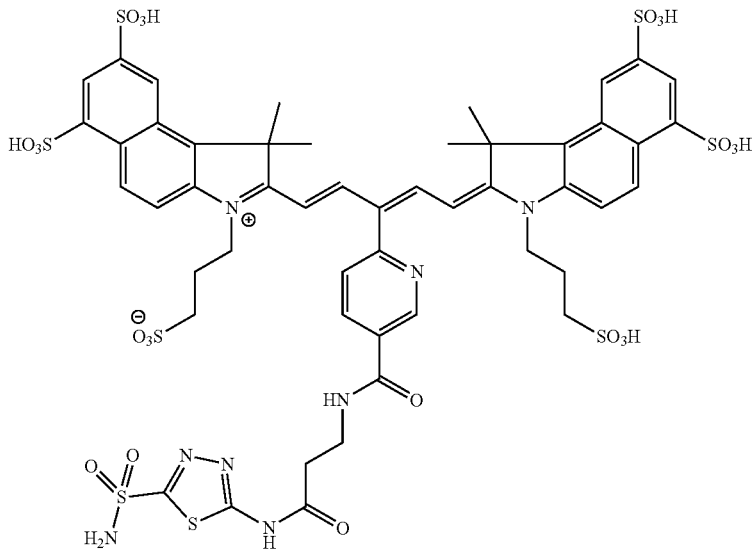

3-amino-N-(5-sulfamoyl-1,3,4-thiadiazol-2-yl)propanamide (5 mg, 20 μmol) was combined with the succinimidyl ester of fluorochrome F5 (15 μmol) and 10 μL of N-methylmorpholine in 200 μL of anhydrous DMF in a sealed reaction tube and rotated at 37° C. for 2 h. The crude product was precipitated by addition of 1.5 mL of ethyl acetate, then purified by prep HPLC and the mass confirmed by LCMS, calculated for [M+H]+ 1373.1, found 1373.2.

Example 15: Synthesis of Exemplary Compound 3-(5-(bis(2-sulfoethyl)carbamoyl)-2-((1E,3Z,5E)-5-(5-(bis(2-sulfoethyl)carbamoyl)-3,3-dimethyl-1-(3-sulfopropyl)indolin-2-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-3,3-dimethyl-3H-indol-1-ium-1-yl)propane-1-sulfonate [C11]

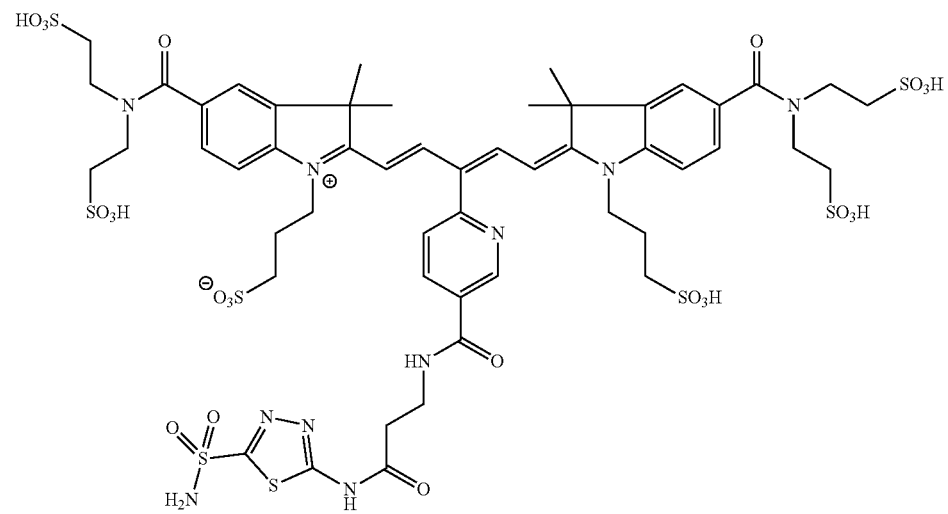

3-amino-N-(5-sulfamoyl-1,3,4-thiadiazol-2-yl)propanamide (5 mg, 20 µmol) is combined with the succinimidyl ester of fluorochrome F11 (15 µmol) and 10 µL of N-methylmorpholine in 200 µL of anhydrous DMF in a sealed reaction tube and rotated at 37° C. for 2 h. The crude product is precipitated by addition of 1.5 mL of ethyl acetate, then purified by prep HPLC and the mass confirmed by LCMS.

Example 16: Synthesis of Nonbinding Control Compound 3-(2-((1E,3Z,5E)-3-(5-((6-(benzylamino)-6-oxohexyl)carbamoyl)pyridin-2-yl)-5-(1,1-dimethyl-6,8-disulfo-3-(3-sulfopropyl)-1H-benzo[e]indol-2(3H)-ylidene)penta-1,3-dien-1-yl)-1,1-dimethyl-6,8-disulfo-1H-benzo[e]indol-3-ium-3-yl)propane-1-sulfonate [D3]

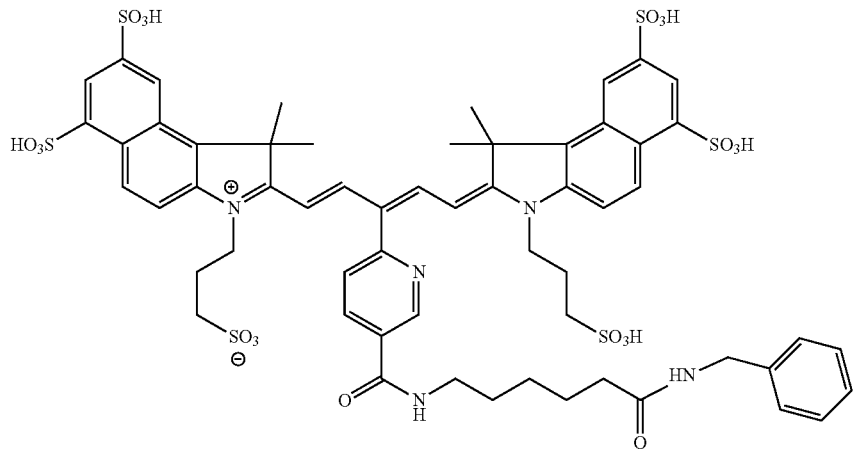

Benzylamine (1.4 mg, 13 µmol), the succinimidyl ester of fluorochrome F3 (11 µmol) and 6.2 µL N-methylmorpholine (55 µmol), were combined in 105 µL of anhydrous DMF in a sealed vial and rotated at 25° C. for 1 hour. The crude product was precipitated by addition of 1.5 mL of ethyl acetate, centrifuged, decanted and dried under vacuum. The product was purified by HPLC and the mass confirmed by LCMS: Calculated for [M+H]+ 1342.2, found 1342.1.

Example 17: Imaging of Tumors In Vivo Using CA Agents

Figure 1B:
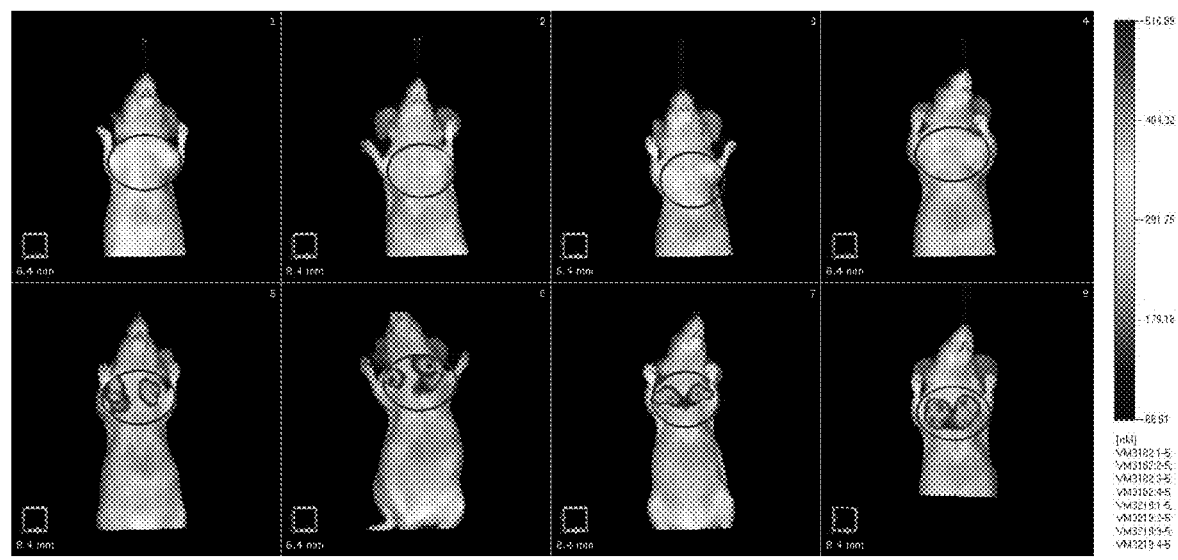

This example shows that the compounds of the invention can be used to image tumors in vivo. In this experiment, NU/NU mice 6-8 weeks old (Charles River Laboratory, Wilmington, Mass.) were injected subcutaneously (s.c.) with about 2×10$^6$ HeLa cells bilaterally in each mammary fat pad. When tumors reached an approximate size of 3×3 mm, mice were injected intravenously (i.v.) with 2 nmoles of carbonic anhydrase agent C5 or nonbinding control agent D3 (5 mice/probe+2 mice/no probe as control) in 100 µL volume via tail vein. Imaging was conducted at 24 hrs post-injection using a Fluorescence Molecular Tomography system (VisEn Medical, Bedford, Mass.) that is commercially available. Examples of images using are depicted in FIG. 1, which shows that the tumors can be imaged effectively by both planar reflectance (1A) imaging and tomographically (1B) in vivo with agent C5 while the nonbinding control agent D3 shows little or no tumor signal by either imaging mode.

Example 18: Affinity of CA Agents to Carbonic Anhydrase In Vitro

This example shows that the compounds of the invention have high affinity for carbonic anhydrases and are selective for carbonic anhydrase IX over CA II, CA XII and CA XIV in vitro. Also shown is that the control compound D3 does not have high affinity to carbonic anhydrases. In this experiment, $K_i$ values were determined by measuring the rate of $CO_2$ hydration of the CA spectrophotometrically by a stopped flow method in the presence of varying concentrations of the CA agents. The results are summarized in Table 5.

TABLE 5

| Compound | $K_i$ (nM) | | | |
|---|---|---|---|---|
| | CA II | CA IX | CA XII | CA XIV |
| B6 (Example 2) | 502 | 9.9 | 40 | 69 |
| A1 (Example 8) | 288 | 8.4 | 57 | 77 |
| A5 (Example 9) | 271 | 7.9 | 43 | 45 |
| A3 (Example 11) | 9.8 | 7.6 | 36 | 57 |
| A6 (Example 10) | 27.1 | 7.7 | 40 | 84 |
| D3 (Example 16) | >100000 | >100000 | >100000 | >100000 |

Table 5 depicts the $K_i$ values for each experiment, which demonstrate that the CA agents exhibit stronger affinity for carbonic anhydrase IX compared to CA II, CA XII and CA XIV while no specific binding is detected for the control compound D3.

Example 19: Carbonic Anhydrase Dependent Binding of CA Agents to HeLa Cells

This example shows the affinity of the carbonic anhydrase agents described herein for CA IX. Cell binding assays using HeLa cells cultured under both hypoxic conditions (1% 02)

were performed. Hela cells (28,000 cells/cm$^2$) were cultured in 6 well culture plates for 24 h under normoxic (air) or hypoxic (1% 02) conditions. Incubation with a fluorescent anti CA IX Ab (R&D systems) was performed in one well as a positive control followed by incubation for 1 h at 37° C. Carbonic anhydrase agents A5 and A3 (1 µM) or nonbinding control agent D3 were added to individual wells followed by incubation for 30 min. Cells were rinsed three times with PBS then scraped with 2 mL, transferred to 5 mL tubes and then spun for 10 min at 1000 rpm to discard the PBS. The cells were then re-suspend the cells in 400 µL PBS and analyzed by fluorescence microscopy and flow cytometry. For fluorescence microscopy, nuclei were co-stained with DAPI. For the competition study, cells were incubated with acetazolamide (Az) (100 µM) for 2 hour before incubation with agents.

Figure 2:
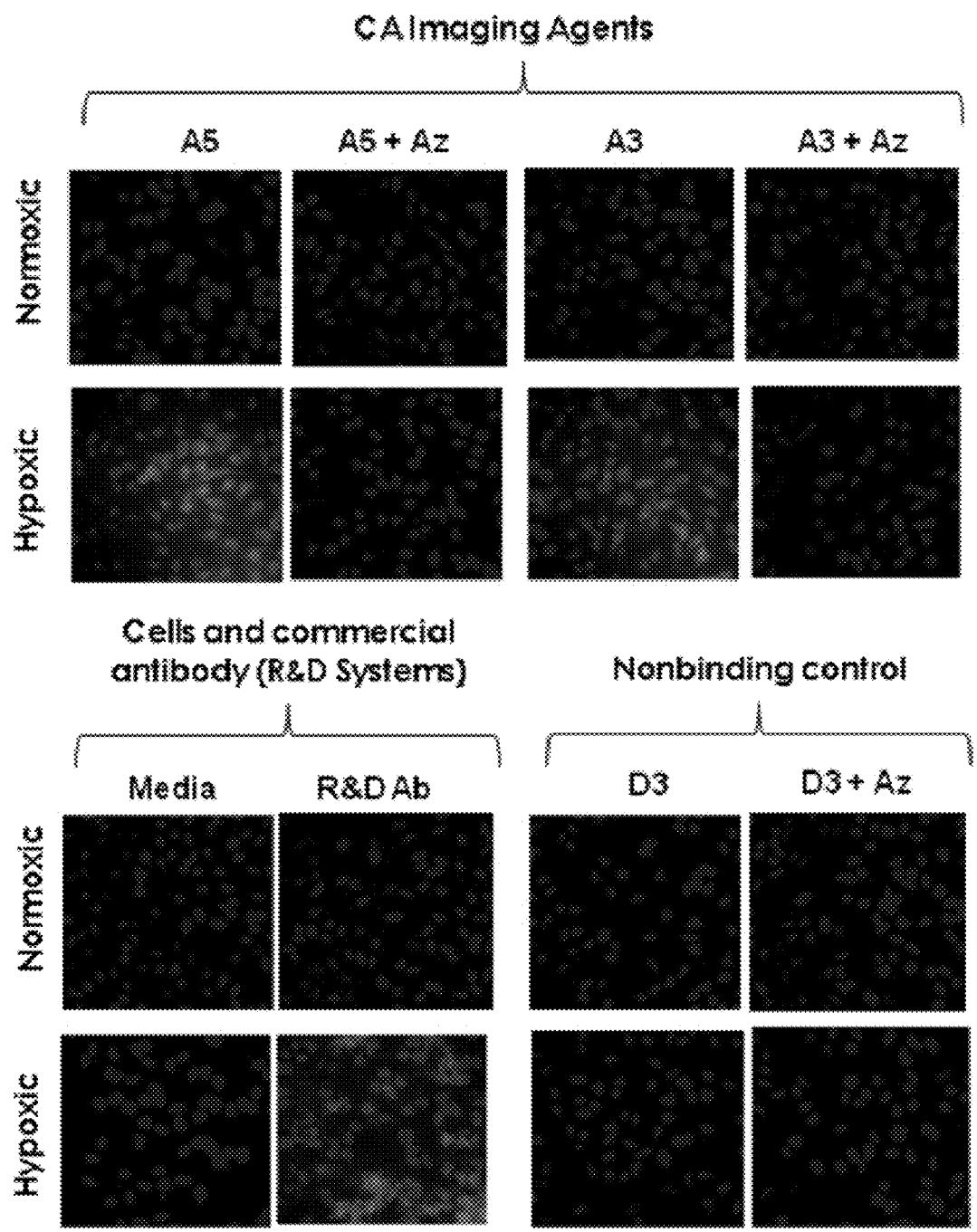
FIG. 2 depicts microscopy images of hypoxic and normoxic HeLa cells incubated with exemplary agents A5 and A3 with and without preincubation of the cells with acetazolamide. Also shown is media as a negative control, a fluorescent, commercial CA IX antibody as a positive control, and the nonbinding control agent D3.
Figure 3:
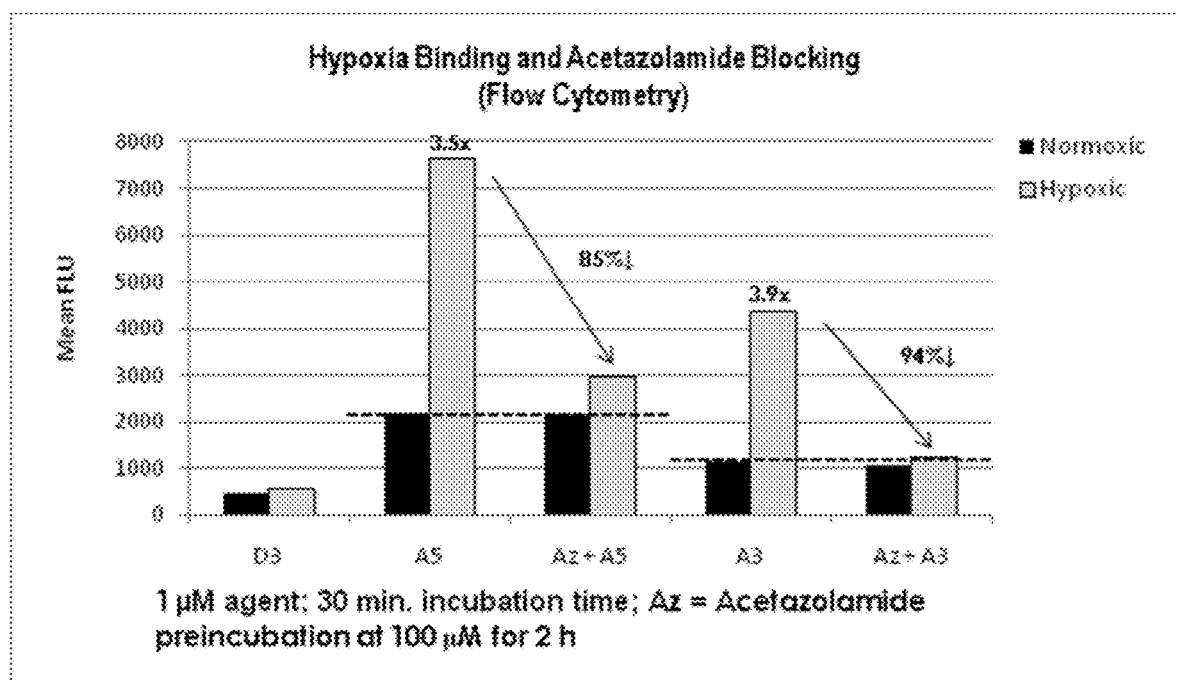
FIG. 3 depicts quantification of HeLa cell fluorescent signal under normoxic and hypoxic conditions upon incubation with nonbinding control compound D3 and exemplary agents A5 and A3, with and without acetazolamide blocking.

FIG. 2 shows that compounds A5 and A3 bound to CA IX receptors on the surface of the hypoxic cells but not normoxic cells and the binding can be blocked with an excess of the CA inhibitor acetazolamide. FIG. 2 also shows that the commercial fluorescent CA IX antibody binds only to hypoxic HeLa cells confirming upregulation and expression of CA IX in these cells, and that the nonbinding control agent D3 doesn't bind to either normoxic or hypoxic cells. These results demonstrate that compounds A5 and A3 bind to hypoxic cells in a carbonic anhydrase-dependent manner. FIG. 3 shows flow cytometry results confirming increased binding of the CA agents A5 and A3 but not nonbinding control compound D3 to hypoxic cells and blocking of the signal with acetazolamide.

Example 20: Biodistribution of I.V. Administered Compound C5 in Mice

This example shows the biodistribution of compound C5 in HeLa tumor bearing mice 24 h post i.v. injection.

Figure 4:
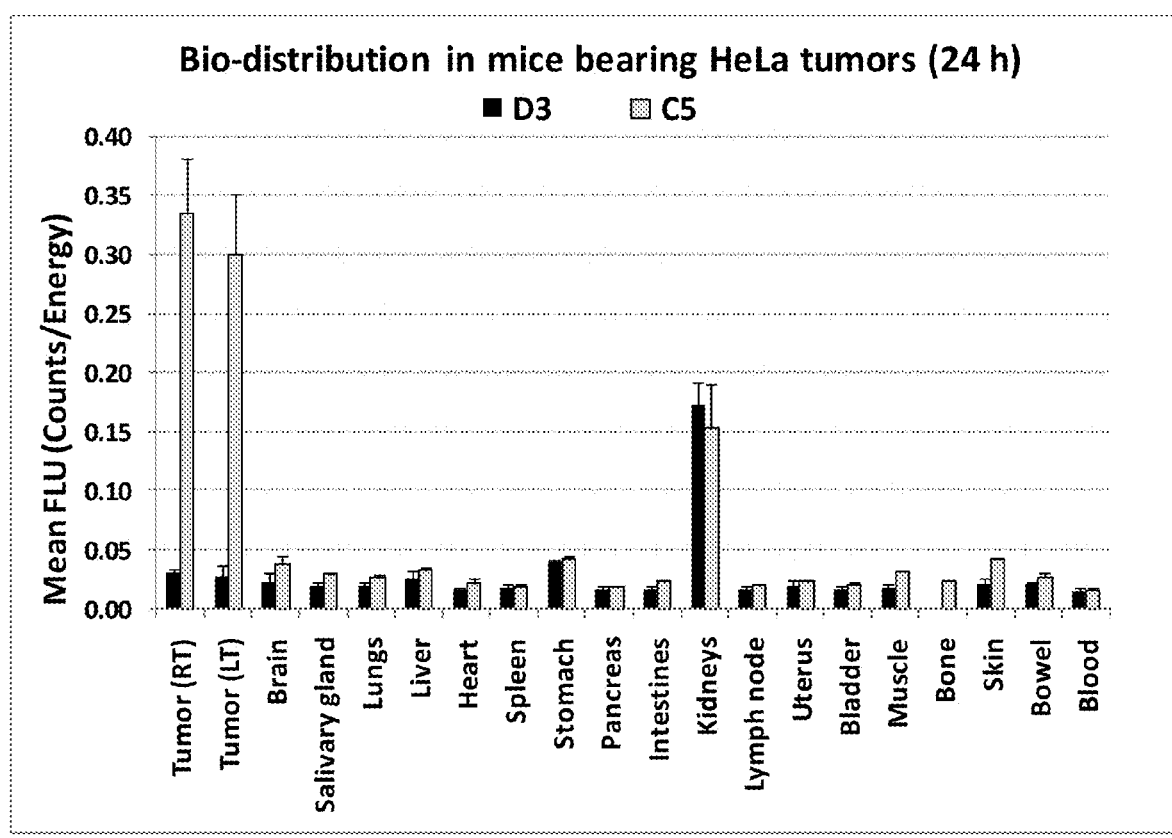
FIG. 4 depicts the biodistribution of nonbinding control agent D3 and exemplary agent C5 24 hours post injection in tumor bearing mice.

Female NU/NU mice 6-8 weeks old (Charles River Laboratory, Wilmington, Mass.) were injected subcutaneously (s.c.) with HeLa cells (5×10$^6$) in the first mammary fat pads. Once tumors reached the desired volume (measured with calipers using the formula volume mm$^3$=(length×width$^2$)/2), mice were injected i.v. with compound C5 (2 nmoles) or nonbinding control D3. Mice were sacrificed by carbon dioxide asphyxiation 24 hr later and certain tissues removed, rinsed with saline, blotted dry, and the imaged on a VisEn FMT 2500 using the reflectance mode. Regions of interest (ROIs) were drawn around each organ using the FMT Software and the mean fluorescence (reported as counts/energy) determined for each organ and normalized to the mean fluorescence in tumors taken to be 100%. The results are summarized in FIG. 4, which shows that CA imaging agent C5 fluorescence is very low in most tissues with the high concentrations found in tumors, and lower concentrations accumulated in the kidneys while the nonbinding control D3 shows fluorescence accumulation only in the kidneys.

Example 21: Effect of Carbonic Anhydrase Inhibitor Acetazolamide Treatment on Carbonic Anhydrase Signal in HeLa Tumor-Bearing Mice This example demonstrates the effects of carbonic anhydrase inhibitor treatment on carbonic anhydrase HeLa tumor-bearing mice.

Figure 5A:
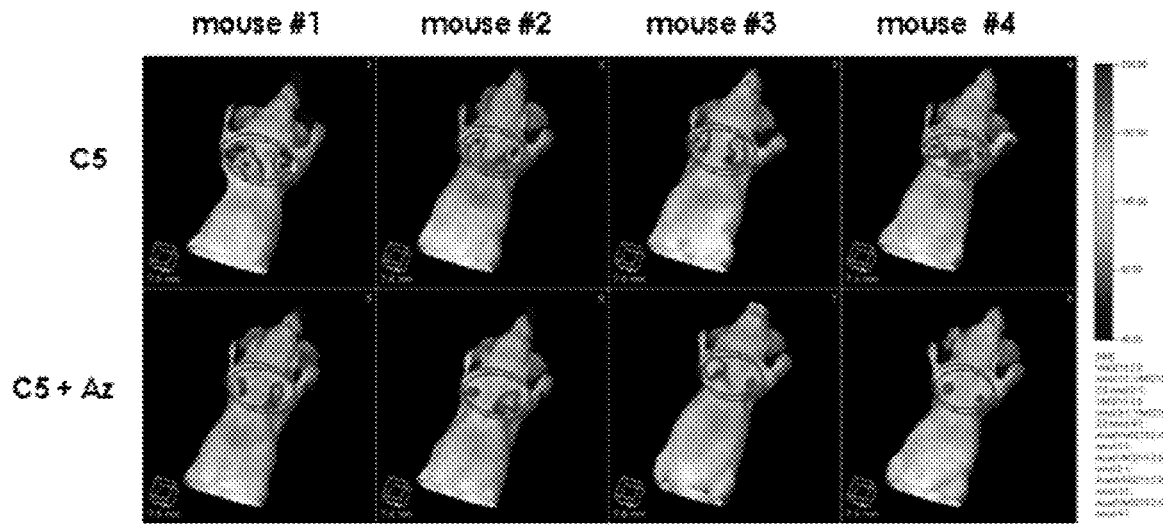
FIGS. 5A-B depict tomographic images (FIG. 5A) and total tumor fluorescence as quantified by FMT (FIG. 5B) in HeLa tumor bearing mice with and without pretreatment with i.v. acetazolamide.

HeLa tumor-bearing mice were randomized once their tumors reached the desired volume and injected i.v. with either C5 (2 nmoles). For competition studies, mice were injected with the acetazolamide (10 mg/kg) followed 60 minutes later by compound C5 (2 nmoles). Imaging was performed 24 hours after administration of the agents using the FMT 2500. As depicted in FIG. 5A, the acetazolamide treated mice had reduced signal of the exemplary agent C5 compared to untreated animals.

Figure 5B:
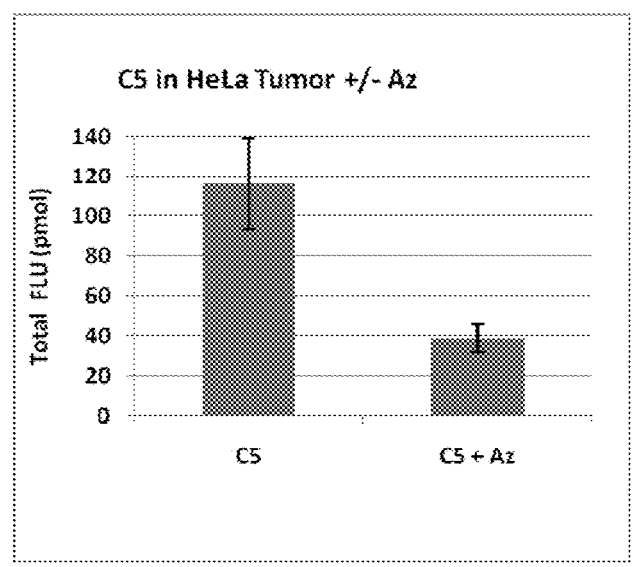

As depicted in FIG. 5B, CA agent C5 showed significant accumulation in tumors in vivo, (116 pmol as quantified by FMT) while the acetazolamide treated animals had approximately 66% less signal (39 pmol as quantified by FMT) demonstrating carbonic anhydrase specificity of the in vivo tumor signal of the CA imaging agents described herein.

Figure 6A:
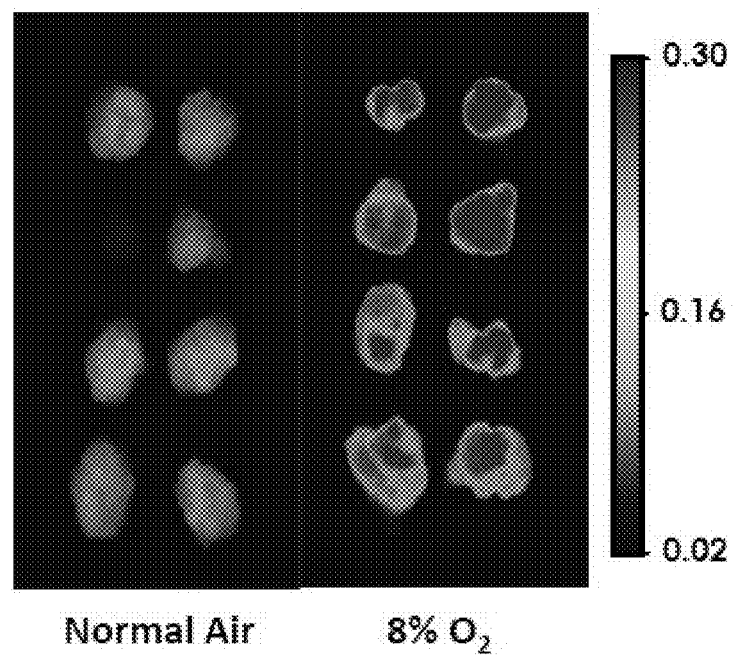
FIGS. 6A-B depict fluorescence images of excised HeLa tumors from mice treated with exemplary agent C5 and placed in normal air or 8% oxygen (FIG. 6A). Quantitative analysis of the imaged tumors indicates a greater uptake of the exemplary agent C5 in tumors from mice under hypoxic conditions (FIG. 6B).
Figure 6B:
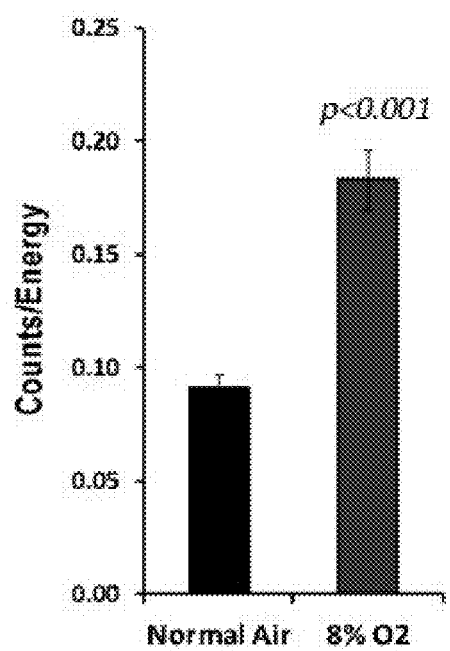

Example 22: Detection of In Vivo Induction of Hypoxia with Fluorescent Carbonic Anhydrase Binding Compound in Mice with HeLa Tumors Female nu/nu mice at 4-5 weeks old, obtained from (Harlan Laboratory, Indianapolis, Ind.) were injected subcutaneously (s.c.) with HeLa cells (1.5×10$^6$ cells/site) in the mammary fat pads. Once tumors reached the desired volume of 600-700 mm$^3$ (measured with calipers using the formula volume mm$^3$=length×width$^2$/2), mice were grouped randomly (n=4-5 mice/group) for with some exposed to controlled hypoxic environmental conditions (8% oxygen) in a chamber with monitored oxygen levels. Control mice with matched tumor volumes were maintained under normal housing conditions. C5, (2 nmol) was injected intravenously to all mice at 24 hours after the initiation of the experiment. Hypoxic mice were placed back into the hypoxic chamber after the injection, and tumors were excised and imaged by fluorescence reflectance imaging (FRI) 24 hours following injection. FIG. 6 shows fluorescence images of the excised tumors from mice that were placed in normal air (left) and 8% 02 (right). Quantitative analysis of the images is shown in the graph indicating significantly greater uptake of C5 in tumors from mice under hypoxic atmosphere.

Figure 7:
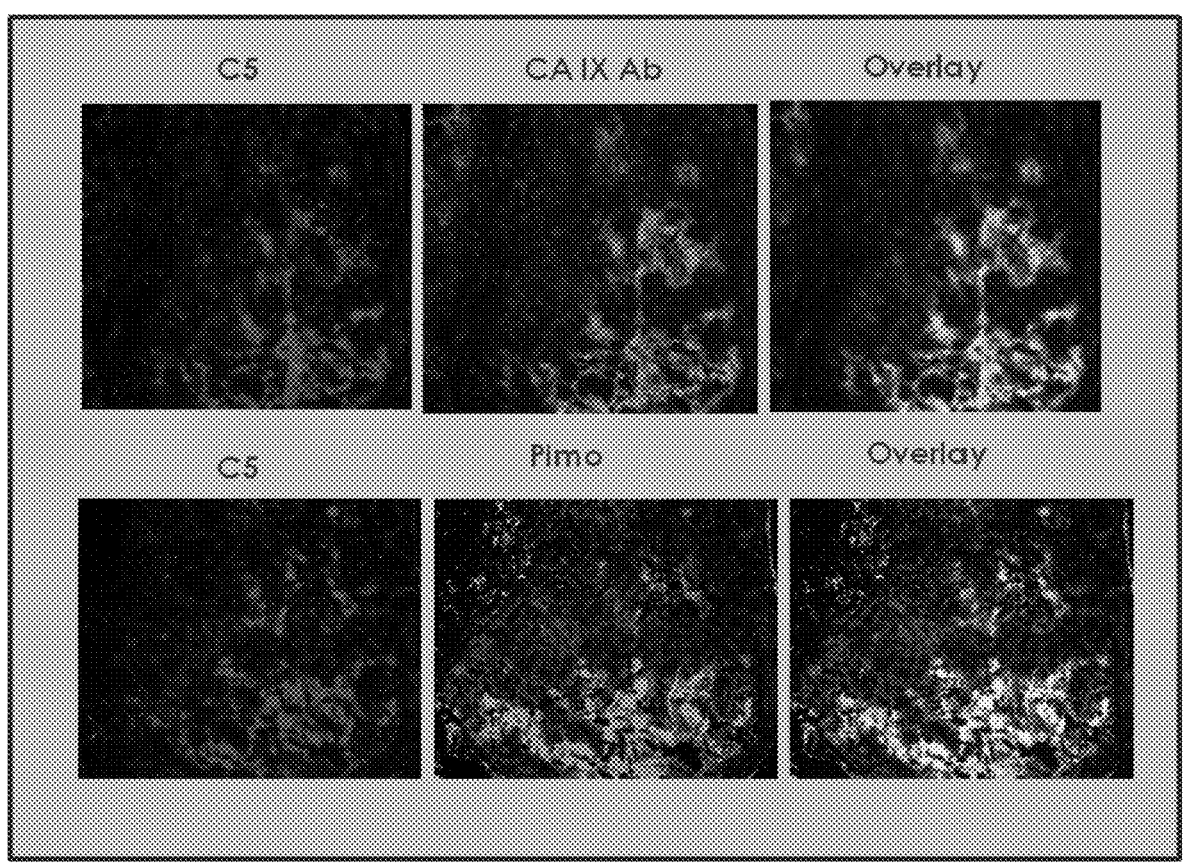
FIG. 7 depicts the distribution of the fluorescent carbonic anhydrase binding compounds in tumor tissue by fluorescence microscopy. In separate tumor sections, the exemplary agent C5 co-localizes with both CA IX antibody and the hypoxia marker pimonidazole (pimo).

Example 23: Distribution of Fluorescent Carbonic Anhydrase Binding Compound in Tumor Tissue by Fluorescence Microscopy FIG. 7 shows the distribution of C5 fluorescence signal in HeLa tumor bearing mice as determined by fluorescence microscopy of tumor tissue sections co-stained with anti CA IX antibody or pimonidazole (a hypoxia marker). Tumor bearing mice injected with C5 were then injected intravenously with pimonidazole (80 mg/kg), a marker of hypoxic tissue, and Hoechst 33342 (25 mg/kg), which stains highly perfused tissue, one hour and five minutes before sacrifice, respectively (38). Tumors, kidneys and muscle tissues were collected and imaged by FRI. The tissues were then embedded, frozen in OCT (Optimal Cutting Temperature compound), and stored at −80° C. until they were sectioned for fluorescence microscopy and immunostaining. Sections of 8 µm thickness were prepared and air dried for 10 min. Sections were imaged for Hoechst (blue) in combination with C5 (red). After acquiring images, the sections were fixed in ice-cold acetone for 20 min and incubated in SuperBlock (37515, Thermo Scientific) for 30 min. The tissue sections were then stained with detection antibodies diluted with blocking solution for 1 hour; CA IX expression was detected with fluorescein-conjugated Anti-Human CA IX monoclonal antibody (FAB2188F, R&D System) diluted 1:10 and pimonidazole binding was detected by FITC-conjugated murine anti-pimonidazole monoclonal antibody (provided in the Hypoxyprobe plus kit) diluted 1:25 to a adjacent section. The sections were imaged again in blue (Hoechst) and green (pimonidazole and CA IX) fluorescence. Finally, the sections were stained with H&E according to standard protocol. Images were taken by Carl Zeiss Axiovert fluorescence microscope. All images were taken at 25× magnification (2.5× objective) with identical exposure times. The tumor tissue distribution of C5 co-localizes with both CA IX antibody and the hypoxia marker pimonidazole and is located away from well perfused areas indicated by the Hoechst stain.

INCORPORATION BY REFERENCE

All publications, patents, and patent applications cited herein are hereby expressly incorporated by reference in their entirety and for all purposes to the same extent as if each was so individually denoted. Further carbonic anhydrase imaging agents are described in U.S. Pat. No. 7,833,737; and International Application Publication Nos. WO2006/137092, WO2008/124703, WO 2010/147666, and WO2010/065906, all of which are incorporated herein by reference in their entirety.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A carbonic anhydrase targeting agent represented by formula (I), or a salt thereof:

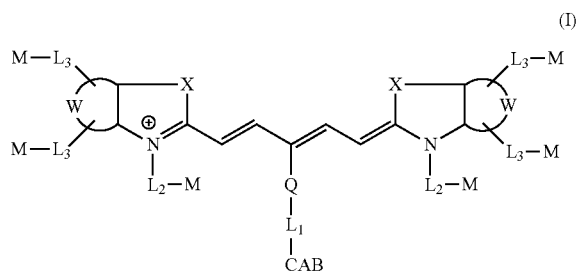

(I)

wherein:
CAB is a carbonic anhydrase binding moiety comprising a sulfonamide and an aliphatic, aromatic or heteroaromatic moiety;
Q is a substituted or unsubstituted aryl, substituted or unsubstituted heteroaryl, $C_1$-$C_{18}$ alkyl, alkenyl, alkynyl, alkoxy, or thioalkyl group; or Q is absent;
Li, $L_2$, and $L_3$ each is independently for each occurrence a bond or a linker moiety;
W is a benzo-condensed ring;
X is, independently for each occurrence, $C(CH_2Y_1)(CH_2Y_2)$, O, S, or Se;
Yi and $Y_2$ are independently hydrogen or a $C_1$-$C_{20}$ aliphatic group, each of which is optionally substituted with $L_3$-M;
M is independently for each occurrence a substituent selected from the group consisting of hydrogen, alcohol, sulfonic acid, sulfonate, polysulfonate, cysteic acid, sulfonamide, sulfoxide, sulfone, carboxylate, ketone, phosphonate, phosphate; iminodiacetate, ethylenediamine tetra-acetic acid, diethylenetriamine pentaacetic acid, tetra-azacyclododecane tetra-acetic acid, an amino acid or polyamino acid, oligo- or polyethylene glycol, amine, quaternary ammonium ion, a sugar, glucosamine, galactosamine, mannosamine, polyethylene glycol (PEG), alkoxy polyethylene glycol, a branched polypropylene glycol, polypropylene glycol, a graft copolymer of poly-lysine and methoxypolyethyleneglycol, a peptide, a lipid, a fatty acid, palmitate, phospholipid, a phospholipid-PEG conjugate, a carbohydrate, an iron oxide nanoparticle, naphthylalanine, phenylalanine, 3,3-diphenylpropylamine, taurine, a phosphonate, a phosphate, a carboxylate, and a polycarboxylate.

2. A carbonic anhydrase targeting agent represented by formula (II), or a salt thereof:

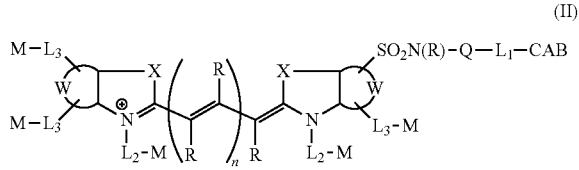

(II)

wherein:
CAB is a carbonic anhydrase binding moiety comprising a sulfonamide and an aliphatic, aromatic or heteroaromatic moiety;
Q is a substituted or unsubstituted aryl, substituted or unsubstituted heteroaryl, $C_1$-$C_{18}$ alkyl, alkenyl, alkynyl, alkoxy, or thioalkyl group; or Q is absent;
Li, $L_2$, and $L_3$ each is independently for each occurrence a bond or a linker moiety;
R is, independently for each occurrence, hydrogen, substituted or unsubstituted aryl, substituted or unsubstituted heteroaryl, $C_1$-$C_{18}$ alkyl, alkenyl, alkynyl, alkoxy, or thioalkyl group, each of which is optionally substituted with $L_3$-M;
n is 1, 2, or 3;
W is a benzo-condensed ring;
X is, independently for each occurrence, $C(CH_2Y_1)(CH_2Y_2)$, O, S, or Se;
Yi and $Y_2$ are independently hydrogen or a $C_1$-$C_{20}$ aliphatic group, each of which is optionally substituted with $L_3$-M; and
M is independently for each occurrence a substituent selected from the group consisting of hydrogen, alcohol, sulfonic acid, sulfonate, polysulfonate, cysteic acid, sulfonamide, sulfoxide, sulfone, carboxylate, ketone, phosphonate, phosphate; iminodiacetate, ethylenediamine tetra-acetic acid, diethylenetriamine pentaacetic acid, tetra-azacyclododecane tetra-acetic acid, an amino acid or polyamino acid, oligo- or polyethylene glycol, amine, quaternary ammonium ion, a sugar, glucosamine, galactosamine, mannosamine, polyethylene glycol (PEG), alkoxy polyethylene glycol, a branched polypropylene glycol, polypropylene glycol, a graft copolymer of poly-lysine and methoxypolyethyleneglycol, a peptide, a lipid, a fatty acid, palmitate, phospholipid, a phospholipid-PEG conjugate, a carbohydrate, an iron oxide nanoparticle, naphthylalanine, phenylalanine, 3,3-diphenylpropylamine, taurine, a phosphonate, a phosphate, a carboxylate, and a polycarboxylate.

3. The agent of claim 1, wherein the agent is fluorescent in the far-red or near-infrared.

4. The agent of claim 1, wherein Q is unsubstituted heteroaryl.

5. The agent of claim 1, wherein Q is alkyl.

6. The agent of claim 1, wherein each of $L_1$, $L_2$, and $L_3$ independently is —NH—$(CH_2)_n$—C(=O)— where n=1-8, or a diradical of a moiety selected from the group consisting of glycine, alanine, β-alanine, 4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, a diamine-amino acid, lysine, ornithine, diaminobutyric acid, diaminopropionic acid, succinic acid, glutaric acid, suberic acid, adipic acid, amide, triazole, urea, and thiourea.

7. The agent of claim 1, wherein $L_1$ is one of the following:
(a) —C(O)N(R$^1$)-alkyl-C(O)N(R$^1$)-ψ;
(b) —C(O)N(R$^1$)-alkyl-ψ;
(c) —C(O)N(R$^1$)—[C$_{2-3}$ alkyl-O]$_z$—C$_{1-3}$alkyl-C(O)N(R$^1$)-ψ;
(d) —C(O)N(R$^1$)-alkyl-aryl-C(O)N(R$^1$)-ψ;
(e) —C(O)N(R$^1$)-alkyl-C(O)N(R$^1$)—C$_{1-3}$alkyl-aryl-C(O)N(R$^1$)-ψ; or
(f) —C(O)N(R$^1$)— [C$_{2-3}$ alkyl-O]$_z$—C$_{1-3}$alkyl-C(O)N(R$^1$)-alkyl-aryl-C(O)N(R$^1$)-ψ;
wherein z is an integer from about 3 to about 35,
R$^1$ is independently for each occurrence hydrogen or alkyl, and ψ is a bond to CAB.

8. The agent of claim 1, wherein $L_2$ is $C_{1-5}$ alkyl.

9. The agent of claim 1, wherein $L_3$ is a bond.

10. The agent of claim 1, wherein X is $C(CH_3)_2$.

11. The agent of claim 1, wherein M is independently for each occurrence a sulfonate or —$SO_3H$.

12. The agent of claim 1, wherein M is independently for each occurrence a substituent selected from the group consisting of a carboxylate, phosphonate, phosphate, and iminodiacetate.

13. The agent of claim 1, wherein M is a sulfonate.

14. The agent of claim 1, wherein CAB is -aryl-$SO_2NH_2$, -heterocyclyl-$SO_2NH_2$, -aryl-C(O)N(R')-heteroaryl-$SO_2NH_2$, -heteroaryl-C(O)N(R')-heteroaryl-$SO_2NH_2$, —C(O)N(R')-heteroaryl-heteroaryl-$SO_2NH_2$, or —C(O)N(R')-aryl-heteroaryl-$SO_2NH_2$, wherein R' is independently for each occurrence hydrogen or $C_{1-6}$ alkyl; each aryl and heteroaryl are optionally substituted with 1 or 2 substituents independently selected from the group consisting of alkyl and halogen, and each heterocyclyl is optionally substituted with 1, 2, or 3 substituents independently selected from the group consisting of alkyl, halogen, amino, and oxo.

15. The agent of claim 1, wherein CAB is

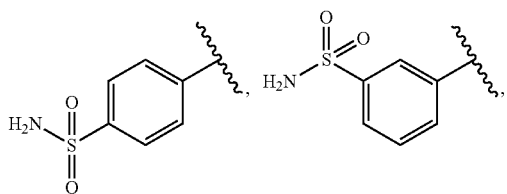

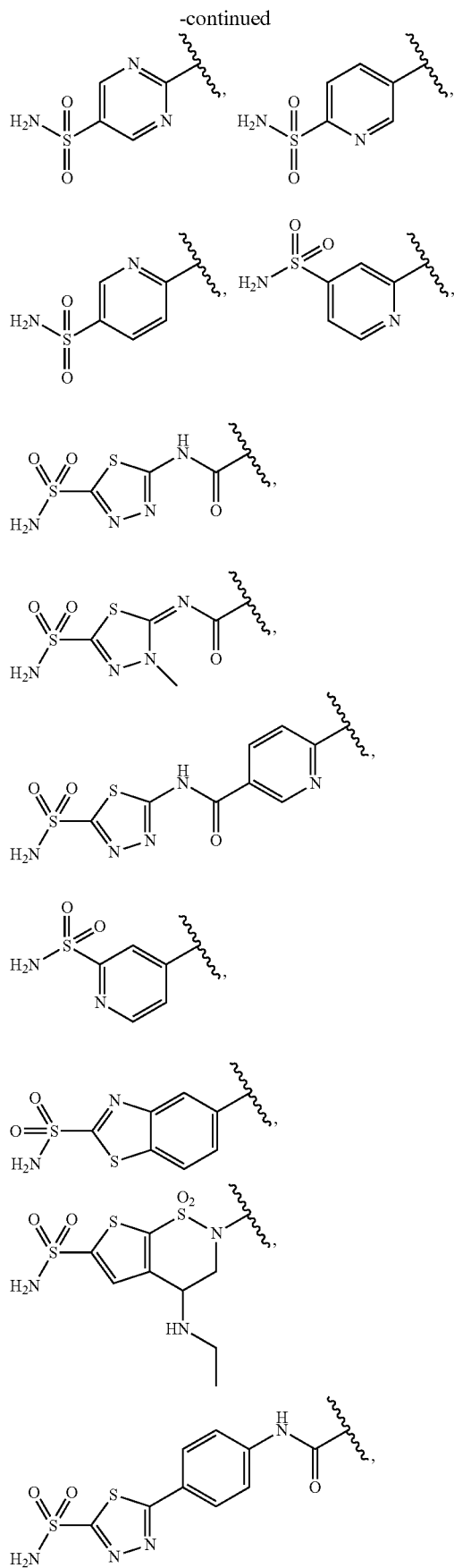

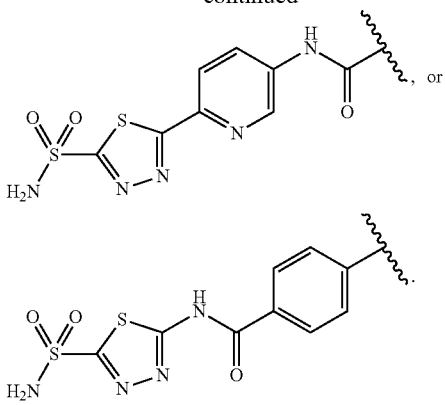

16. The agent of claim 1, wherein the carbonic anhydrase targeting agent is
3-(2-(((1E,3Z,5E)-5-(3,3-dimethyl-5-sulfo-1-(3-sulfopropyl)indolin-2-ylidene)-3-(5-(((3-oxo-3-((5-sulfamoyl-1,3,4-thiadiazol-2-yl)amino)propyl)carbamoyl)pyridin-2-yl)penta-1,3-dien-1-yl)-3,3-dimethyl-5-sulfo-3H-indol-1-ium-1-yl)propane-1-sulfonate;
or a pharmaceutically acceptable salt thereof.

17. A pharmaceutical composition suitable for administration to a subject, comprising the agent of claim 1 and a pharmaceutically acceptable excipient.

18. The agent of claim 2, wherein the agent is fluorescent in the far-red or near-infrared.

19. The agent of claim 2, wherein Q is unsubstituted heteroaryl.

20. The agent of claim 2, wherein Q is alkyl.

21. The agent of claim 2, wherein each of Li, $L_2$, and $L_3$ independently is —NH—$(CH_2)_n$—C(=O)— where n=1-8, or a diradical of a moiety selected from the group consisting of glycine, alanine, β-alanine, 4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, a diamine-amino acid, lysine, ornithine, diaminobutyric acid, diaminopropionic acid, succinic acid, glutaric acid, suberic acid, adipic acid, amide, triazole, urea, and thiourea.

22. The agent of claim 2, wherein Li is one of the following:
(a) —C(O)N($R^1$)-alkyl-C(O)N($R^1$)-ψ;
(b) —C(O)N($R^1$)-alkyl-ψ;
(c) —C(O)N($R^1$)—[$C_{2-3}$ alkyl-O]$_z$—$C_{1-3}$alkyl-C(O)N($R^1$)-ψ;
(d) —C(O)N($R^1$)-alkyl-aryl-C(O)N($R^1$)-ψ;
(e) —C(O)N($R^1$)-alkyl-C(O)N($R^1$)—$C_{1-3}$alkyl-aryl-C(O)N($R^1$)-ψ; or
(f) —C(O)N($R^1$)— [$C_{2-3}$ alkyl-O]$_z$—$C_{1-3}$alkyl-C(O)N($R^1$)-alkyl-aryl-C(O)N($R^1$)-ψ;
wherein z is an integer from about 3 to about 35,
$R^1$ is independently for each occurrence hydrogen or alkyl, and
ψ is a bond to CAB.

23. The agent of claim 2, wherein $L_2$ is $C_{1-5}$ alkyl.

24. The agent of claim 2, wherein $L_3$ is a bond.

25. The agent of claim 2, wherein X is $C(CH_3)_2$.

26. The agent of claim 2, wherein M is independently for each occurrence a sulfonate or —$SO_3H$.

27. The agent of claim 2, wherein M is independently for each occurrence a substituent selected from the group consisting of a carboxylate, phosphonate, phosphate, and iminodiacetate.

28. The agent of claim 2, wherein M is a sulfonate.

29. The agent of claim 2, wherein CAB is -aryl-$SO_2NH_2$, -heterocyclyl-$SO_2NH_2$, -aryl-C(O)N(R')-heteroaryl-$SO_2NH_2$, -heteroaryl-C(O)N(R')-heteroaryl-$SO_2NH_2$, —C(O)N(R')-heteroaryl-heteroaryl-$SO_2NH_2$, or —C(O)N(R')-aryl-heteroaryl-$SO_2NH_2$, wherein R' is independently for each occurrence hydrogen or $C_{1-6}$ alkyl; each aryl and heteroaryl are optionally substituted with 1 or 2 substituents independently selected from the group consisting of alkyl and halogen, and each heterocyclyl is optionally substituted with 1, 2, or 3 substituents independently selected from the group consisting of alkyl, halogen, amino, and oxo.

30. The agent of claim 2, wherein CAB is

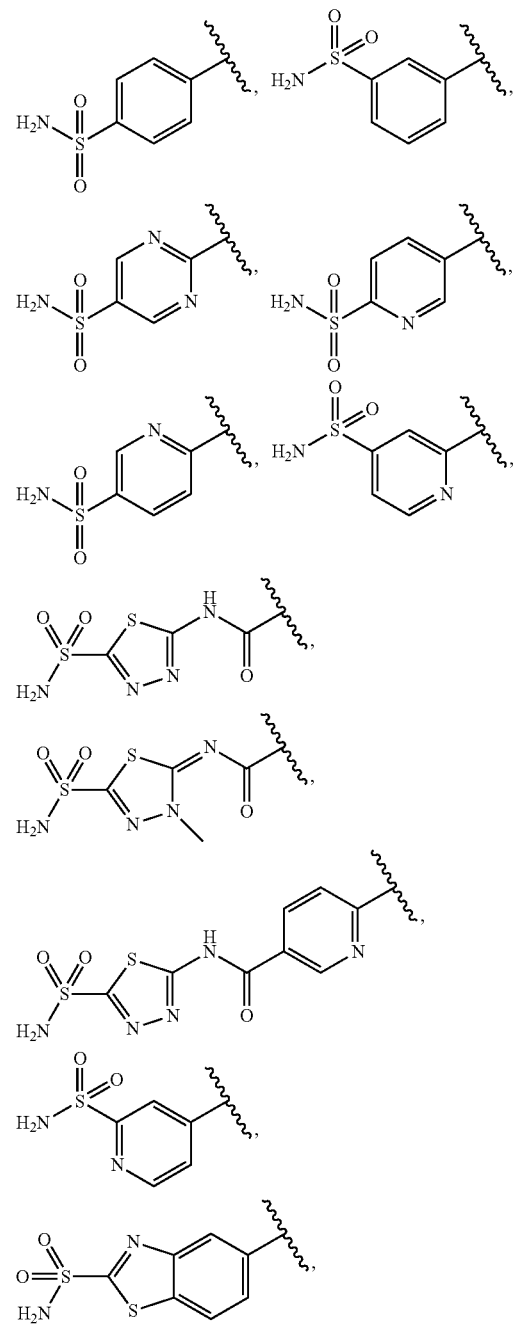

-continued

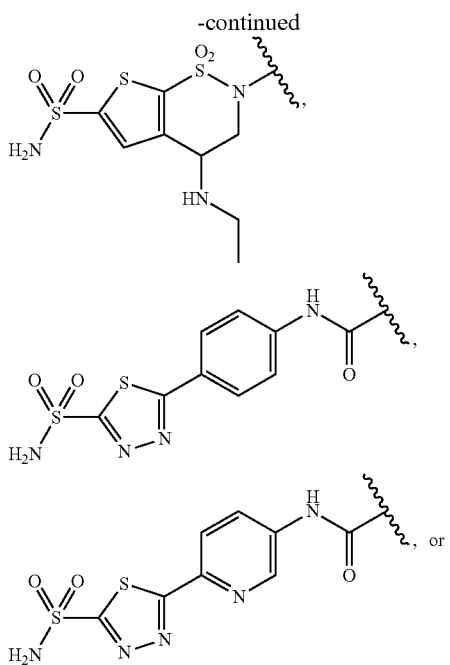

-continued

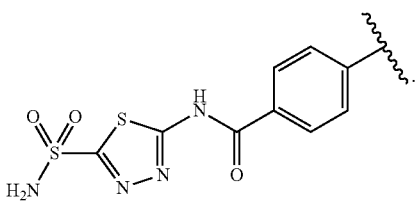

31. The agent of claim 2, wherein the carbonic anhydrase targeting agent is 3-(2-((1E,3Z,5E)-5-(3,3-dimethyl-5-sulfo-1-(3-sulfopropyl)indolin-2-ylidene)-3-(5-((3-oxo-3-((5-sulfamoyl-1,3,4-thiadiazol-2-yl)amino)propyl)carbamoyl)pyridin-2-yl)penta-1,3-dien-1-yl)-3,3-dimethyl-5-sulfo-3H-indol-1-ium-1-yl)propane-1-sulfonate;

or a pharmaceutically acceptable salt thereof.

32. A pharmaceutical composition suitable for administration to a subject, comprising the agent of claim 2 and a pharmaceutically acceptable excipient.

* * * * *

UNITED STATES PATENT AND TRADEMARK OFFICE
CERTIFICATE OF CORRECTION

PATENT NO. : 11,059,802 B2  
APPLICATION NO. : 16/286901  
DATED : July 13, 2021  
INVENTOR(S) : Groves et al.

Page 1 of 1

It is certified that error appears in the above-identified patent and that said Letters Patent is hereby corrected as shown below:

In the Claims

In Claim 1 at Column 123, Line 63, replace "Li, $L_2$, and $L_3$" with --$L_1$, $L_2$, and $L_3$--.

In Claim 1 at Column 124, Line 1, replace "Yi and $Y_2$" with --$Y_1$ and $Y_2$--.

In Claim 2 at Column 124, Line 42, replace "Li, $L_2$, and $L_3$" with --$L_1$, $L_2$, and $L_3$--.

In Claim 2 at Column 124, Line 53, replace "Yi and $Y_2$" with --$Y_1$ and $Y_2$--.

In Claim 6 at Column 125, Line 12, replace "each of Li, $L_2$, and $L_3$" with --each of $L_1$, $L_2$, and $L_3$--.

In Claim 21 at Column 127, Line 34, replace "each of Li, $L_2$, and $L_3$" with --each of $L_1$, $L_2$, and $L_3$--.

In Claim 22 at Column 127, Line 44, replace "Li is one of the" with --$L_1$ is one of the--.

Signed and Sealed this  
Sixteenth Day of November, 2021

Drew Hirshfeld  
*Performing the Functions and Duties of the*  
*Under Secretary of Commerce for Intellectual Property and*  
*Director of the United States Patent and Trademark Office*